(12) United States Patent
Yue et al.

(10) Patent No.: US 9,714,444 B2
(45) Date of Patent: Jul. 25, 2017

(54) SYSTEMS AND METHODS FOR MULTIPLE ANALYTE DETECTION

(71) Applicant: APPLIED BIOSYSTEMS, LLC, Carlsbad, CA (US)

(72) Inventors: Min Yue, Belmont, CA (US); David M. Liu, Los Altos, CA (US); Joy Roy, San Jose, CA (US); Yuh-Min Chiang, Sunnyvale, CA (US); Joon Mo Yang, Redwood City, CA (US); Dennis Lehto, Santa Clara, CA (US); Charles S. Vann, El Dorado Hills, CA (US); Nigel P. Beard, San Diego, CA (US); Ian A. Harding, San Mateo, CA (US); John R. Van Camp, San Ramon, CA (US); Alexander Dromaretsky, Davis, CA (US); Sergey V. Ermakov, Castro Valley, CA (US); Mark F. Oldham, Emerald Hills, CA (US); Maryam Shariati, Sunnyvale, CA (US); Umberto Ulmanella, Foster City, CA (US)

(73) Assignee: APPLIED BIOSYSTEMS, LLC, Carlsbad ( * ) Notice: Subject to any disclaimer, the term of this patent is extended or adjusted under 35 U.S.C. 154(b) by 173 days.

(21) Appl. No.: 14/093,933

(22) Filed: Dec. 2, 2013

(65) Prior Publication Data
US 2014/0162264 A1 Jun. 12, 2014

Related U.S. Application Data

(63) Continuation of application No. 12/789,363, filed on May 27, 2010, now Pat. No. 8,597,590, which is a
(Continued)

(51) Int. Cl.
*C12Q 1/68* (2006.01)
*B01L 3/00* (2006.01)
*G01N 35/02* (2006.01)

(52) U.S. Cl.
CPC ...... *C12Q 1/6806* (2013.01); *B01L 3/502707* (2013.01); *B01L 3/502723* (2013.01);
(Continued)

(58) Field of Classification Search
CPC ... B01J 2219/00317; B01J 2219/00722; B01L 2200/0684; B01L 2200/0689;
(Continued)

(56) References Cited

U.S. PATENT DOCUMENTS

| | | | | |
|---|---|---|---|---|
| 4,895,706 A | * | 1/1990 | Root | B01D 61/18 422/534 |
| 5,288,463 A | | 2/1994 | Chemelli | |

(Continued)

FOREIGN PATENT DOCUMENTS

CA 2714073 7/2003

*Primary Examiner* — Sally Merkling

(57) ABSTRACT

Systems and methods for multiple analyte detection include a system for distribution of a biological sample that includes a substrate, wherein the substrate includes a plurality of sample chambers, a sample introduction channel for each sample chamber, and a venting channel for each sample chamber. The system may further include a preloaded reagent contained in each sample chamber and configured for nucleic acid analysis of a biological sample that enters the substrate and a sealing instrument configured to be placed in contact with the substrate to seal each sample chamber so as to substantially prevent sample contained in each sample chamber from flowing out of each sample chamber. The substrate can be constructed of detection-compatible and assay-compatible materials.

23 Claims, 44 Drawing Sheets

Related U.S. Application Data continuation of application No. 11/380,327, filed on Apr. 26, 2006, now abandoned.

(60) Provisional application No. 60/674,750, filed on Apr. 26, 2005, provisional application No. 60/674,876, filed on Apr. 26, 2005, provisional application No. 60/696,157, filed on Jun. 30, 2005.

(52) U.S. Cl.
CPC ... *G01N 35/028* (2013.01); *B01J 2219/00317* (2013.01); *B01J 2219/00722* (2013.01); *B01L 3/50853* (2013.01); *B01L 2200/0684* (2013.01); *B01L 2200/0689* (2013.01); *B01L 2200/16* (2013.01); *B01L 2300/041* (2013.01); *B01L 2300/048* (2013.01); *B01L 2300/0636* (2013.01); *B01L 2300/087* (2013.01); *B01L 2300/0816* (2013.01); *B01L 2300/0829* (2013.01); *B01L 2300/0864* (2013.01); *B01L 2400/0481* (2013.01); *B01L 2400/0487* (2013.01); *B01L 2400/0655* (2013.01); *B01L 2400/0694* (2013.01); *Y10T 436/2575* (2015.01)

(58) Field of Classification Search
CPC ........... B01L 2200/16; B01L 2300/041; B01L 2300/048; B01L 2300/0636; B01L 2300/0816; B01L 2300/0829; B01L 2300/0864; B01L 2300/087
See application file for complete search history.

(56) References Cited

U.S. PATENT DOCUMENTS

| | | | |
|---|---|---|---|
| 5,589,350 A | | 12/1996 | Bochner |
| 5,800,785 A | | 9/1998 | Bochner |
| 5,939,312 A | | 8/1999 | Baier et al. |
| 5,948,673 A | | 9/1999 | Cottingham |
| 6,027,694 A | * | 2/2000 | Boulton ............... B01J 19/0046 422/553 |
| 6,124,138 A | | 9/2000 | Woudenberg et al. |
| 6,126,899 A | * | 10/2000 | Woudenberg ......... B01L 3/5027 422/50 |
| 6,268,219 B1 | | 7/2001 | McBride et al. |
| 6,326,211 B1 | | 12/2001 | Anderson et al. |
| 6,488,897 B2 | | 12/2002 | Dubrow et al. |
| 6,500,390 B1 | | 12/2002 | Boulton et al. |
| 6,514,750 B2 | | 2/2003 | Bordenkircher et al. |
| 6,601,613 B2 | | 8/2003 | McNeely et al. |
| 6,627,159 B1 | | 9/2003 | Bedingham et al. |
| 6,632,656 B1 | | 10/2003 | Thomas et al. |
| 6,637,463 B1 | | 10/2003 | Lei et al. |
| 6,696,286 B1 | | 2/2004 | Halverson et al. |
| 6,762,049 B2 | | 7/2004 | Zou et al. |
| 6,783,736 B1 | | 8/2004 | Taylor et al. |
| 6,814,935 B2 | | 11/2004 | Harms et al. |
| 6,825,047 B1 | | 11/2004 | Woudenberg et al. |
| 6,942,837 B2 | | 9/2005 | Frye et al. |
| 7,026,168 B2 | | 4/2006 | Bedingham et al. |
| 2003/0082551 A1 | | 5/2003 | Zarling et al. |
| 2004/0077074 A1 | | 4/2004 | Ackley et al. |
| 2004/0110275 A1 | | 6/2004 | Sandell |
| 2011/0020179 A1 | | 1/2011 | Yue et al. |

* cited by examiner

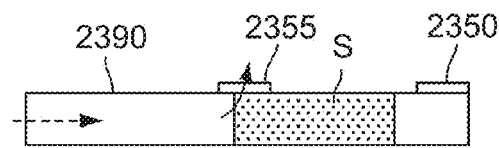
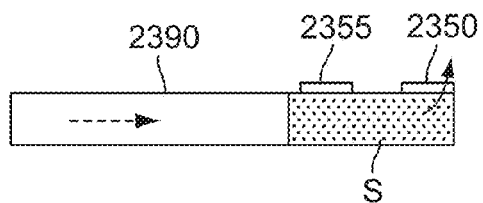
FIG. 23A  FIG. 23B
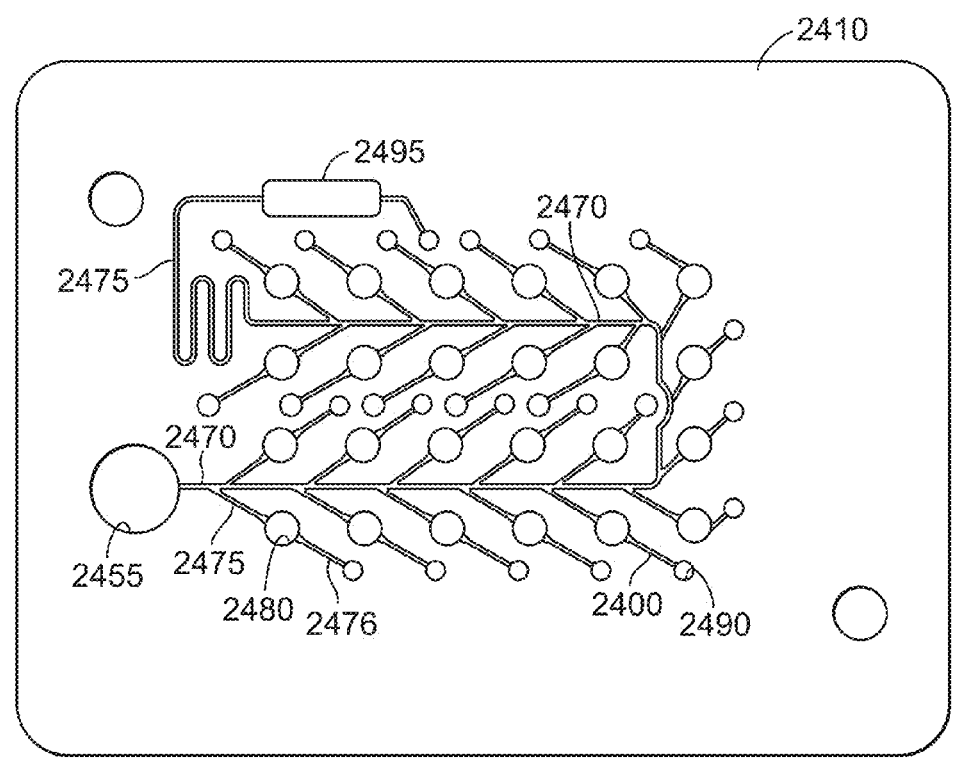
FIG. 24

FIG. 44
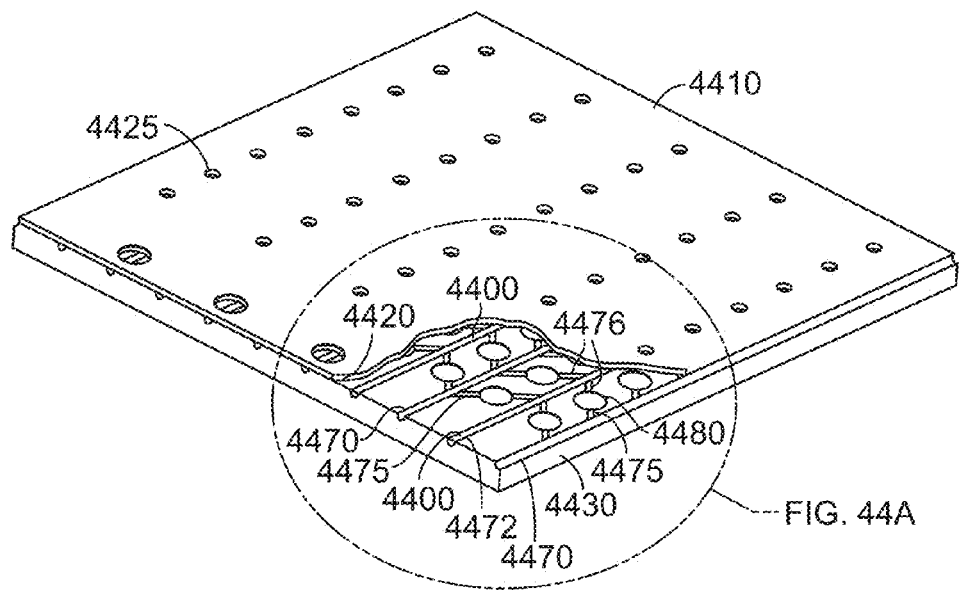
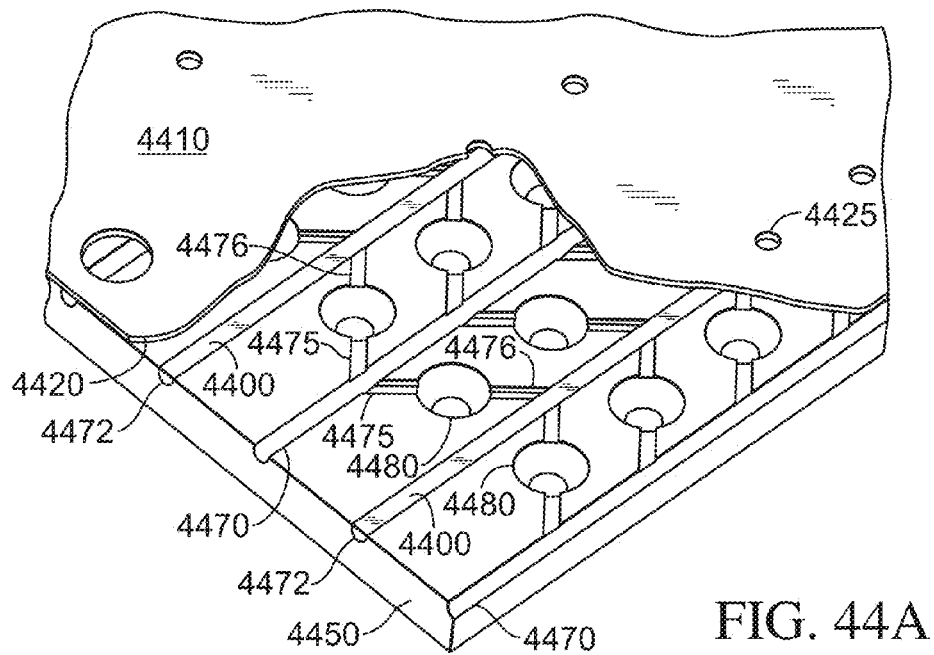
FIG. 44A

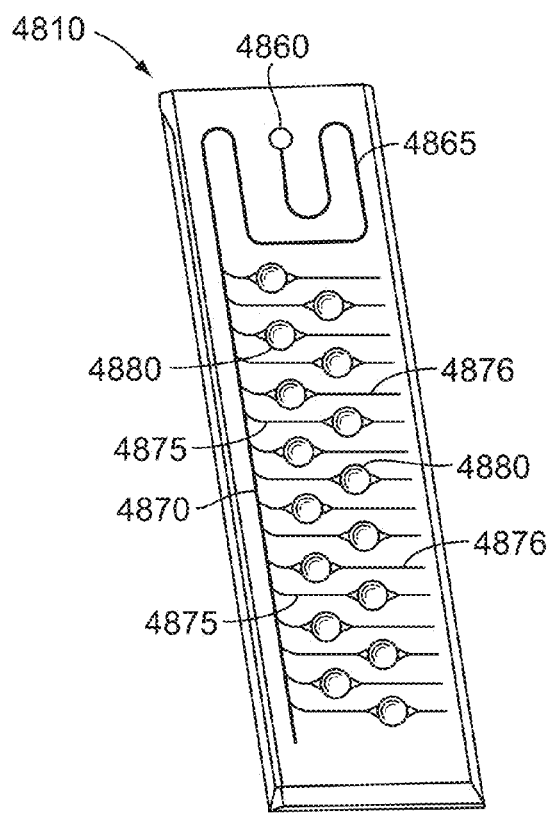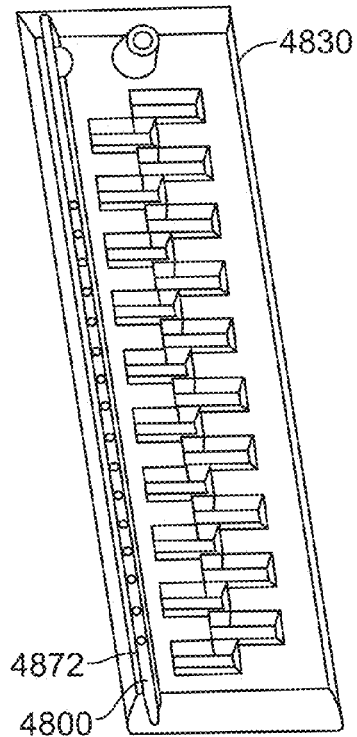
FIG. 48A   FIG. 48B
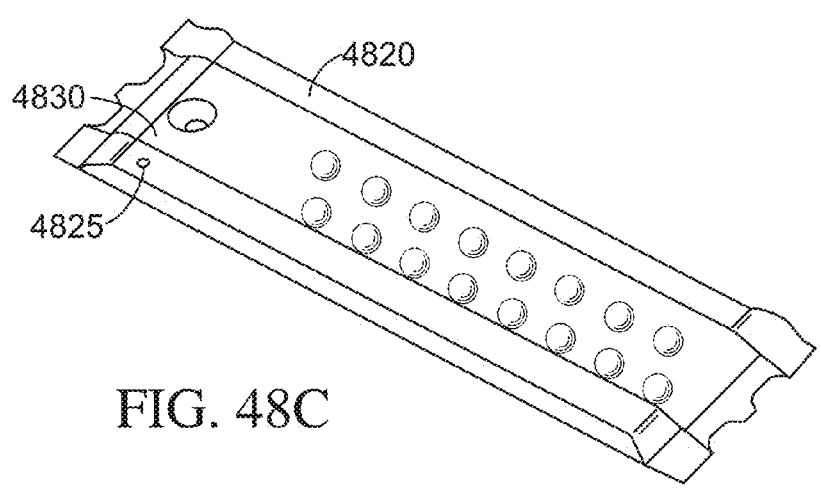
FIG. 48C

SYSTEMS AND METHODS FOR MULTIPLE ANALYTE DETECTION

CROSS-REFERENCE TO COPENDING APPLICATIONS

This application is a continuation of patent application Ser. No. 12/789,363 filed May 27, 2010, which is a continuation of patent application Ser. No. 11/380,327 filed Apr. 26, 2006, which claims the benefit of priority to U.S. Provisional Application No. 60/674,750 filed on Apr. 26, 2005, all of which are incorporated by reference in their entirety herein.

This application makes cross-reference to U.S. Provisional Application No. 60/674,876, entitled "System for Population Security and Epidemiological Analysis," concurrently filed with U.S. Provisional Application No. 60/674,750, and later filed 60/696,157 of the same title, all of which are also incorporated by reference herein in their entirety.

FIELD

The present teachings relate to systems and methods for multiple analyte detection.

BACKGROUND

Biochemical testing for research and diagnostic applications can require simultaneous assays including a large number of analytes in conjunction with one or a few samples and can include extended sample manipulation, multiple test substrates, multiple analytical instruments, and other steps. It is desirable to provide a method for analyzing one or a few biological samples using a single test device with a large number of analytes while requiring a small amount of sample. It is desirable to provide a device that is small in size while providing high-sensitivity detection for the analytes of interest with minimal sample manipulation. It is desirable to provide a method of loading the sample(s) into chambers on the substrate and individually sealing each chamber. It is further desirable to provide a mechanism for venting of the substrate during filling, while also avoiding and/or minimizing leakage of fluid (e.g., biological sample and/or reagents) from the test device.

SUMMARY

In various embodiments, the present teachings can provide a system for distribution of a biological sample including a substrate with a plurality of sample chambers, a sample introduction channel for each sample chamber, and a venting channel for each sample chamber, wherein the substrate is constructed of detection-compatible and assay-compatible materials, and a sealing plate with sealing protrusions for sealing the sample introduction channels and the venting channels for each sample chamber.

In various embodiments, the present teachings can provide a method for distribution of a biological sample including providing an injection molded base, wherein the base includes a plurality of sample cavities, a sample introduction trench for each sample cavity, and a venting trench for each sample cavity, and wherein the base is constructed of detection-compatible and assay-compatible materials, providing a film to adhere to the base forming a substrate, wherein film includes a plurality of vents, and wherein the film forms a plurality of sample chambers from each sample cavity, a sample introduction channel for each sample introduction trench, and a venting channel for sample venting trench, providing the biological sample to the substrate, forcing the biological sample to the sample chambers through the sample introduction channels, providing a sealing plate comprising sealing protrusions for each sample chamber, heating the sealing plate, sealing the sample chambers by contacting the sealing protrusions with the sample introductory channels and the venting channels of each sample chamber.

In various embodiments, the present teachings may provide a system for distribution of a biological sample that includes a substrate, wherein the substrate includes a plurality of sample chambers, a sample introduction channel for each sample chamber, and a venting channel for each sample chamber. The system may further include a preloaded reagent contained in each sample chamber and configured for nucleic acid analysis of a biological sample that enters the substrate, and a sealing instrument configured to be placed in contact with the substrate to seal each sample chamber so as to substantially prevent sample contained in each sample chamber from flowing out of each sample chamber. The substrate can be constructed of detection-compatible and assay-compatible materials.

In still further various embodiments, a method for distribution of a biological sample may include providing a base, wherein the base includes a plurality of sample cavities containing a preloaded reagent therein, a sample introduction trench for each sample cavity, and a venting trench for each sample cavity, and wherein the base is constructed of detection-compatible and assay-compatible materials. The method also may include providing a film to adhere to the base to form a substrate, wherein the film and base form a plurality of sample chambers from each sample cavity, a sample introduction channel from each sample introduction trench, and a venting channel from each sample venting trench. The method may further include supplying the biological sample to the substrate, filling the sample chambers with the biological sample via the sample introduction channels, passing gas out of the substrate via at least one venting mechanism in the substrate, and sealing the sample chambers to substantially prevent sample in the sample chambers from flowing out of the sample chambers.

According to yet other embodiments, the present teachings may provide a system for distribution of a biological sample that includes means for distributing the sample to a plurality of sample chambers containing a preloaded reagent, means for venting each of the sample chambers, and means for sealing each of the sample chambers.

In various embodiments, the present teachings also can provide a device for testing a biological sample that includes a substrate defining a plurality of distribution portions configured to distribute biological sample throughout the substrate, the plurality of distribution portions comprising a plurality of sample chambers, a sample introduction channel for each sample chamber, and a venting channel for each sample chamber. The device also may include a substance disposed in at least one of the distribution portions, the substance being configured to seal each sample chamber so as to substantially prevent sample disposed in each sample chamber from flowing out of each sample chamber during testing of the biological sample.

Additional embodiments are set forth in part in the description that follows, and in part will be apparent from the description, or may be learned by practice of the various embodiments described herein.

BRIEF DESCRIPTION OF THE DRAWINGS

Various embodiments of the present teachings are exemplified in the accompanying drawings. The teachings are not limited to the embodiments depicted, and include equivalent structures and methods as set forth in the following description and known to those of ordinary skill in the art. In the drawings:

FIGS. 23A and 23B schematically illustrate cross-sectional views of exemplary steps of filling a feature of a substrate for biological analysis;

FIG. 24 illustrates a top view of yet another substrate for biological analysis according to various embodiments of the present teachings;

FIG. 44 is a perspective view of a substrate for biological analysis according to various embodiments of the present teachings;

FIG. 44A is a close-up of section 44A of the substrate of FIG. 44;

FIGS. 48A-48C are perspective views of yet another substrate for biological analysis according to various embodiments of the present teachings;

Figure 1:
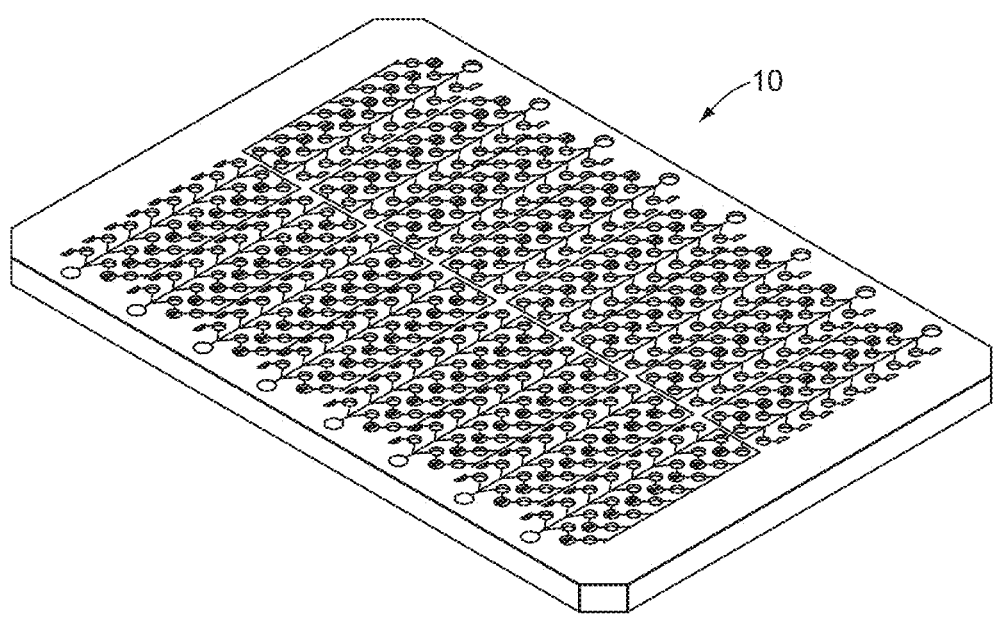
FIG. 1 illustrates a perspective view of a substrate base for biological analysis according to various embodiments of the present teachings.

It is to be understood that both the foregoing general description and the following detailed description are exemplary and explanatory only and are intended to provide a further explanation of the various embodiments of the present teachings.

DESCRIPTION OF VARIOUS EMBODIMENTS

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

The term "sample chamber" as used herein refers to any structure that provides containment to a sample. The chamber can have any shape including circular, rectangular, cylindrical, etc. Multi-chamber arrays can include 12, 16, 24, 36, 48, 96, 192, 384, 3072, 6144, or more sample chambers. The term "channel" as used herein refers to any structure that is smaller than a chamber. A channel can have any shape. It can be straight or curved, as necessary, with cross-sections that are shallow, deep, square, rectangular, concave, or V-shaped, or any other appropriate configuration. A "distribution portion" of a substrate may refer to any portion of the substrate configured to contain, flow, receive, or otherwise hold sample and/or gas in the substrate. Examples of distribution portions include main fluid supply channels, venting channels, venting chambers, sample chambers, sample introduction channels, overfill chambers, and virtually any other channels and/or chambers of the substrate.

The term "biological sample" as used herein refers to any biological or chemical substance, typically in an aqueous solution with luminescent dye that can produce emission light in relation to nucleic acid present in the solution. The biological sample can include one or more nucleic acid sequence(s) to be incorporated as a reactant in a polymerase chain reaction (PCR) and other reactions such as ligase chain reactions, antibody binding reactions, oligonucleotide ligations assay, hybridization assays, and invader assays (e.g., for an isotherm reaction). The biological sample can include one or more nucleic acid sequences to be identified for DNA sequencing.

The term "luminescent dye" as used herein may refer to fluorescent or phosphorescent dyes that can be excited by excitation light or chemiluminscent dyes that can be excited chemically. As used herein, "luminescent dye" may also include the use of energy transfer pairs (intramolecular or intermolecular). For example, excitation of one energy transfer pair member and emission of the other member may expand the range of emission wavelengths for multiplexing. Quenchers selected should be suitable for both members of the energy transfer pair. Luminescent dyes can be used to provide different colors depending on the dyes used. Several dyes will be apparent to one skilled in the art of dye chemistry, including, for example, intercalating dyes. One or more colors can be collected for each dye to provide identification of the dye or dyes detected. The dye can be a dye-labeled fragment of nucleotides. The dye can be a marker triggered by a fragment of nucleotides. The dye can provide identification of a nucleic acid sequence in the biological sample by association, for example, bonding to or reacting with a detectable marker, for example, a respective dye and quencher pair. The respective identifiable component can be positively identified by the luminescence of the dye. The dye can be normally quenched, and then can become unquenched in the presence of a particular nucleic acid sequence in the biological sample. The fluorescent dyes can be selected to exhibit respective and, for example, different, excitation and emission wavelength ranges. The luminescent dye can be measured to quantitate the amount of nucleic acid sequences in the biological sample. The luminescent dye can be detected in real-time to provide information about the identifiable nucleic acid sequences throughout the reaction. Examples of fluorescent dyes with desirable excitation and emission wavelengths can include 5-FAM™, TET™, and VIC™. The term "luminescence" as used herein refers to low-temperature emission of light including fluorescence, phosphorescence, electroluminescence, and chemiluminescence.

In various embodiments, sample chambers can be dimensioned to hold from 0.0001 µL to 10 µL of sample per chamber, or between 0.001 µL and 2 µL. Conveniently, the volume of each detection chamber is between 0.001 µL and 1 µL. For example, a chamber having a volume of 0.2 µL may have dimensions of 1 mm×1 mm×0.2 mm, where the last dimension is the chamber's depth. As a further example, a chamber may have a substantially cylindrical shape having a diameter of about 1.96 mm and a depth of about 0.5 mm and a volume of about 1.35 µL.

In various embodiments, the sample introduction channels can be dimensioned to facilitate rapid delivery of sample to the sample chambers, while occupying as little volume as possible. For example, cross-sectional dimensions for the channels can range from 0.5 µm to 250 µm for both the width and depth. In some embodiments, the channel path lengths to the sample chambers can be minimized to reduce the total channel volume. For example, the network can be substantially planar, i.e., the sample introduction channels and sample chambers in the substrate intersect a common plane.

"Venting mechanisms" as used herein may refer to any mechanism configured and arranged to permit gas to escape therethrough and leave the substrate. Venting mechanisms may be the last structure the gas passes through prior to leaving the substrate or be a structure that passes the escaping gas therethrough to another structure that is the last structure before the gas escapes the substrate. According to various embodiments, venting mechanisms may permit the passage of gas while substantially preventing the passage of liquid. Also, venting mechanisms may be used in combination with one another to permit gas to escape the substrate. Examples of venting mechanisms include, but are not limited to, gas-permeable or porous membranes, vent through holes either in a film layer, a base or both, porous fibers, and hydrophobic liquid stops.

In various embodiments, there are a variety of means for distributing the biological sample to the plurality of sample chambers. All of these include applying a force. The force can be a pulling force or a pushing force, depending on whether it provides a negative (pulling) or positive (pushing) force relative to the direction of fluid flow. Examples of forces and how the force is enacted upon the biological sample include spinning the substrate to provide centrifugal force to push the liquid, sizing the sample introductory channels to provide capillary force to pull the liquid, aspirating the sample through the vents to pull the liquid, evacuating the sample chamber to pull the liquid, and/or providing pressure, such as by pumping, compressing, plunging, etc. to push the liquid. In each of these configurations, the venting channels and vents can be used to accommodate the displaced venting gas, whether air or other gas such as nitrogen, that is pushed out by the sample or the venting channels and vents can be used to evacuate the gas in the sample chambers to create a vacuum for the sample or aspirate sample itself.

In various embodiments, the substrate that defines the sample-distribution network can be constructed from any solid material that is suitable for conducting analyte detection. Materials that can be used will include various plastic polymers and copolymers, such as polypropylenes, polystyrenes, polyimides, COP, COC, and polycarbonates. Inorganic materials such as glass and silicon are also useful. Silicon is especially advantageous in view of its high thermal conductivity, which facilitates rapid heating and cooling of the substrate if necessary. The substrate can be formed from a single material or from a plurality of materials. Examples of this are described at U.S. Pat. No. 6,126,899.

In various embodiments, the sample-distribution network including cavities and trenches, for example, formed in a substrate base portion, can be formed by any suitable method known in the art. For plastic materials, injection molding can be suitable to form sample cavities and connecting channels having a desired pattern. For silicon, standard etching, RIE, DRIE, and wet-etching techniques from the semiconductor industry can be used as known in the art of photo-lithography.

In various embodiments, the substrate can be prepared from two or more laminated layers. The term "detection-compatible material" as used herein refers to the optical detection with a substrate that includes one or more layers which provide an optical transparency for each sample chamber. By way of example, the optical transparency may permit detection of a luminescent dye. Silica-based glasses, quartz, polycarbonate, or an optically transparent plastic layer may be used, for example. Selection of the particular detection-compatible material depends in part on the optical properties of the material and the detection mechanism. For example, in luminescent dye-based assays, the material should have low fluorescence emission at the wavelength(s) being measured. The detection-compatible material should also exhibit minimal light absorption for the signal wavelengths of interest. However, in some cases, for example, to minimize cross-talk, it may be desirable to provide a substrate material that has relatively high absorption. Examples of such materials are described at U.S. Pub. No. 2005/0226779A1.

In various embodiments, other layers in the substrate can be formed using the same or different materials. The term "assay-compatible material" as used herein refers to the interaction of assay reagents and assay conditions (heat, pressure, pH, etc.) with the substrate material (hydrophobic, hydrophilic, inert, etc.). For example, the layer or layers, such as a film defining the sample chambers can be formed predominantly from a material that has high heat conductivity, such as silicon, a heat-conducting metal, or carbon fill in plastic. The silicon surfaces that contact the sample can be coated with an oxidation layer or other suitable coating, to render the surface more inert and make it an assay-compatible material. Similarly, where a heat-conducting metal is used in the substrate, the metal can be coated with an assay-compatible material, such as a plastic polymer, to prevent corrosion of the metal and to separate the metal surface from contact with the sample. The suitability of a particular surface should be verified for the selected assay as known by the conditions and reagents used in the assay.

In various embodiments, for optical detection, the opacity or transparency of the substrate material defining the sample chambers, for example, the base, can have an effect on the permissible detector geometries used for signal detection. For the following discussion, references to the "upper wall" of a detection chamber may refer to the chamber surface or wall through which the optical signal is detected, and references to the "lower wall" of a chamber may refer to the chamber surface or wall that is opposite the upper wall. For example, the upper wall can be formed by the base or the film, and the lower wall by the other, respectively.

In various embodiments, in fluorescence detection the substrate material defining the lower wall of the sample chambers can be optically opaque, and the sample chambers can be illuminated and optically scanned through the same surface (i.e., the top surfaces of the chambers which are optically transparent). Thus, for fluorescence detection, the opaque lower wall material can exhibit low reflectance properties so that reflection of the illuminating light back toward the detector can be minimized. Opacity also may prevent collection of background signals from a thermal cycler block or other instrumentation used to test the substrates. In other cases, the substrate lower wall of the sample chambers may be reflective so that more fluorescent signal is collected.

In various embodiments, in fluorescence detection the substrate material defining the upper wall of the sample chambers can be optically clear, the chambers can be illuminated with excitation light through the sides of the chambers (in the plane defined collectively by the sample chambers in the substrate), or more typically, diagonally from above (e.g., at a 45 degree angle), and emitted light is collected from above the chambers (i.e., through the upper walls, in a direction perpendicular to the plane defined by the detection chambers). The upper wall material can exhibit low dispersion of the illuminating light in order to limit Rayleigh scattering.

In various embodiments, in fluorescence detection the substrate material defining the entirety of the substrate can be optically clear, or at least the upper and lower walls of the chambers can be optically clear, the chambers can be illuminated through either wall (upper or lower), and the emitted or transmitted light is measured through either wall as appropriate. Illumination of the chambers from other directions can also be possible as already discussed above.

In various embodiments, in chemiluminescence detection, where light of a distinctive wavelength is typically generated without illumination of the sample by an outside light source, the absorptive and reflective properties of the substrate can be less important, provided that the substrate provides at least one optically transparent window for detecting the signal.

In various embodiments, the substrate can be designed to provide a vacuum-tight environment within the sample-distribution network for sample loading, and also to provide sample chambers having carefully defined reaction volumes. It is desirable to ensure that the network and associate sample chambers do not leak. Accordingly, lamination of substrate layers to one another can be accomplished so as to ensure that all chambers and channels are well sealed.

In various embodiments, the substrate layers can be sealably bonded in a number of ways. A suitable bonding substance, such as a glue or epoxy-type resin, can be applied to one or both opposing surfaces that will be bonded together. The bonding substance may be applied to the entirety of either surface, so that the bonding substance (after curing) can come into contact with the sample chambers and the distribution network. In this case, the bonding substance is selected to be compatible with the sample and detection reagents used in the assay. Alternatively, the bonding substance can be applied around the distribution network and detection chambers so that contact with the sample can be minimal or avoided entirely. The bonding substance may also be provided as part of an adhesive-backed tape or membrane, which is then brought into contact with the opposing surface. In yet another approach, the sealable bonding is accomplished using an adhesive gasket layer, which is placed between the two substrate layers. In any of these approaches, bonding may be accomplished by any suitable method, including pressure-sealing, ultrasonic welding, and heat curing, for example.

In various embodiments, a pressure-sensitive adhesive (PSA) can be used in constructing the substrate. PSA films which can be applied to a surface and adhered to that surface are obtained by applying pressure to the film. Normally, pressure is applied throughout the whole film, so that the whole film can adhere to the surface. PSA films can have threshold pressure in order to activate the adhesion. The threshold pressure can be very low. By applying pressure to some selected regions, the bonding can be limited to those regions only, thus allowing obtaining a bonding pattern. This way channels and chambers can be defined. The elastic properties of the film can then be used to pressure-drive a fluid through the unbonded regions, since the film would deform under the liquid pressure, thus opening up a channel. Eventually, the channel could be sealed by applying pressure on the portion of the film defining the channel. PSA films can be either hydrophobic or hydrophilic. PSA films can have hydrophobic and hydrophilic areas on the same film to provide areas of different wetting characteristics, properly patterned, to provide, for example fluid flow in sample introduction channels and gas venting in venting channels. Thus, by providing differing regions of hydrophobicity and hydrophilicity of the films, control over fluid flow through a device may be achieved. In various embodiments, PSA films that are hydrophilic can have the hydrophilic properties deteriorate in a matter of days. The lack of stability (hydrophilic film turning into hydrophobic) can provide controllable, irreversible or reversible, changes (upon temperature change, heat addition, UV exposure, or just time delay after curing) in the wetting nature of the film. In various embodiments, PSA films can have different porosities and permeabilities to a gas. A highly permeable PSA film can be more advantageous than a low-permeability one for instance to vent the sample chambers. Further, a PSA film whose permeability/porosity can be modified in a reversible fashion with temperature change, and/or in an irreversible fashion by heat addition or UV exposure can be used for sample distribution and then sealed for sample processing. In various embodiments, PSA films can be hydrophilic, provide solvent resistance, maintain the adhesion characteristics at a high temperature (95-100 degree Celsius), and can be optically clear with low auto-fluorescence. In various embodiments, PSA films can be thermally expandable to swell at desired locations and close off channels.

In various embodiments, the substrate of the present teaching can be adapted to allow rapid heating and cooling of the sample chambers to facilitate reaction of the sample with the analyte-detection reagents, including luminescent dyes. In one embodiment, the substrate can be heated or cooled using an external temperature-controller. The temperature-controller is adapted to heat/cool one or more surfaces of the substrate, or can be adapted to selectively heat the sample chambers themselves. To facilitate heating or cooling with this embodiment, the substrate can be formed of a material that has high thermal conductivity, such as copper, aluminum, or silicon. Alternatively, bases can be formed from a material having moderate or low thermal conductivity, while the film can be formed form a conductive material such that the temperature of the sample chambers can be conveniently controlled by heating or cooling the substrate through the film, regardless of the thermal conductivity of the base. For example, the film can be formed of an adhesive copper-backed tape.

In various embodiments, the sample chambers of the substrate can be pre-loaded with detection reagents that are specific for the selected analytes of interest. By way of example, such reagents may be deposited in the sample chambers in liquid form and dried (e.g., lyophilized). For example, reagents for nucleic acid analysis of a biological sample may be preloaded in the substrate, for example, in the sample chambers. In such embodiments, the substrate may then be loaded with sample when biological testing is desired to be performed by supplying sample to the substrate containing the pre-loaded reagent(s). The detection reagents can be designed to produce an optically detectable signal via any of the optical methods known in the field of detection. It will be appreciated that although the reagents in each detection chamber can contain substances specific for the analyte(s) to be detected in the particular chamber, other reagents for production of the optical signal for detection can be added to the sample prior to loading, or may be placed at locations elsewhere in the network for mixing with the sample. Examples of such reactions are described in U.S. Pub. No. 2005/0260640A1. Whether particular assay components are included in the detection chambers or elsewhere will depend on the nature of the particular assay, and on whether a given component is stable to drying. Pre-loaded reagents added in the detection chambers during manufacture of the substrate can enhance assay uniformity and minimize the assay steps conducted by the end-user.

In various embodiments, the analyte to be detected may be any substance whose presence, absence, or amount is desirable to be determined. The detection means can include any reagent or combination of reagents suitable to detect or measure the analyte(s) of interest. It will be appreciated that more than one analyte can be tested for in a single detection chamber, if desired.

In one embodiment, the analytes are selected-sequence polynucleotides, such as DNA or cDNA, RNA, and the analyte-specific reagents include sequence-selective reagents for detecting the polynucleotides. The sequence-selective reagents include at least one binding polymer that is effective to selectively bind to a target polynucleotide having a defined sequence. The binding polymer can be a conventional polynucleotide, such as DNA or RNA, or any suitable analog thereof, which has the requisite sequence selectivity. Other examples of binding polymers known generally as peptide nucleic acids may also be used. The binding polymers can be designed for sequence specific binding to a single-stranded target molecule through Watson-Crick base pairing, or sequence-specific binding to a double-stranded target polynucleotide through Hoogstein binding sites in the major groove of duplex nucleic acid. A variety of other suitable polynucleotide analogs are also known in the art of nucleic acid amplification. The binding polymers for detecting polynucleotides are typically 10-30 nucleotides in length, with the exact length depending on the requirements of the assay, although longer or shorter lengths are also contemplated.

The present teachings can find utility in a wide variety of amplification methods, such as PCR, Reverse Transcription PCR (RT-PCR), Ligation Chain Reaction (LCR), Nucleic Acid Sequence Based Amplification (NASBA), self-sustained sequence replication (3SR), strand displacement activation (SDA), Q (3replicase) system, isothermal amplification methods, and other known amplification method or combinations thereof. Additionally, the present teachings can find utility for use in a wide variety of analytical techniques, such as ELISA; DNA and RNA hybridizations; antibody titer determinations; gene expression; recombinant DNA techniques; hormone and receptor binding analysis; and other known analytical techniques.

In one embodiment, the analyte-specific reagents include an oligonucleotide primer pair suitable for amplifying, by polymerase chain reaction, a target polynucleotide region of the selected analyte that is flanked by 3'-sequences complementary to the primer pair. In practicing this embodiment, the primer pair is reacted with the target polynucleotide under hybridization conditions which favor annealing of the primers to complementary regions of opposite strands in the target. The reaction mixture is then thermal cycled through several, and typically about 20-40, rounds of primer extension, denaturation, and primer/target sequence annealing, according to well-known polymerase chain reaction (PCR) methods. Typically, both primers for each primer pair are pre-loaded in each of the respective sample chambers. The primer also may be loaded along with the standard nucleotide triphosphates, or analogs thereof, for primer extension (e.g., ATP, CTP, GTP, and TTP), and any other appropriate reagents, such as $MgCl_2$ or $MnCl_2$. A thermally stable DNA polymerase, such as Taq, Vent, or the like, may also be pre-loaded in the chambers, or may be mixed with the sample prior to sample loading. Other reagents may be included in the detection chambers or elsewhere as appropriate. Alternatively, the detection chambers may be loaded with one primer from each primer pair, and the other primer (e.g., a primer common to all of sample chambers) can be provided in the sample or elsewhere. If the target polynucleotides are single-stranded, such as single-stranded DNA, cDNA, or RNA, the sample is preferably pre-treated with a DNA- or RNA-polymerase prior to sample loading, to form double-stranded polynucleotides for subsequent amplification. Also, a reverse transcription enzyme may be used to pretreat RNA to cDNA. This pre-treatment can be provided in the cartridge.

In various embodiments, the presence and/or amount of target polynucleotide in a sample chamber, as indicated by successful amplification, is detected by any suitable means. For example, amplified sequences can be detected in double-stranded form by including an intercalating or crosslinking dye, such as ethidium bromide, acridine orange, or an oxazole derivative, such as, Cyber Green, for example, which exhibits a fluorescence increase or decrease upon binding to double-stranded nucleic acids. The level of amplification can also be measured by fluorescence detection using a fluorescently labeled oligonucleotide. In this embodiment, the detection reagents include a sequence-selective primer pair as in the more general PCR method above, and in addition, a sequence-selective oligonucleotide (FQ-oligo) containing a fluorescer-quencher pair. The primers in the primer pair are complementary to 3' regions in opposing strands of the target analyte segment which flank the region which is to be amplified. The FQ-oligo is selected to be capable of hybridizing selectively to the analyte segment in a region downstream of one of the primers and is located within the region to be amplified. The fluorescer-quencher pair can include a fluorescent dye and a quencher which are spaced from each other on the oligonucleotide so that the quencher is able to significantly quench light emitted by the fluorescer S at a selected wavelength, while the quencher and fluorescer are both bound to the oligonucleotide. The FQ-oligo can include a 3'-phosphate or other blocking group to prevent terminal extension of the 3' end of the oligo. The fluorescer and quencher dyes may be selected from any dye combination having the proper overlap of emission (for the fluorescer) and absorptive (for the quencher) wavelengths while also permitting enzymatic cleavage of the FQ-oligo by the polymerase when the oligo is hybridized to the target. Suitable dyes, such as rhodamine and fluorscein derivatives, and methods of attaching them, are well known in the art of nucleic acid amplification.

In another embodiment, the detection reagents include first and second oligonucleotides effective to bind selectively to adjacent, contiguous regions of a target sequence in the selected analyte, and which can be ligated covalently by a ligase enzyme or by chemical means as known in the art of oligonucleotide ligation assay, (OLA). In this approach, the two oligonucleotides (oligos) can be reacted with the target polynucleotide under conditions effective to ensure specific hybridization of the oligonucleotides to their target sequences. When the oligonucleotides have base-paired with their target sequences, such that confronting end subunits in the oligos are base-paired with immediately contiguous bases in the target, the two oligos can be joined by ligation, e.g., by treatment with ligase. After the ligation step, the detection wells are heated to dissociate unligated probes, and the presence of a ligated, target-bound probe is detected by reaction with an intercalating dye or by other means. The oligos for OLA may also be designed so as to bring together a fluorescer-quencher pair, as discussed above, leading to a decrease in a fluorescence signal when the analyte sequence is present. In the above OLA ligation method, the concentration of a target region from an analyte polynucleotide can be increased, if necessary, by amplification with repeated hybridization and ligation steps. Simple additive amplification can be achieved using the analyte polynucleotide as a target and repeating denaturation, annealing, and ligation steps until a desired concentration of the ligated product is achieved.

In another embodiment, the ligated product formed by hybridization and ligation can be amplified by ligase chain reaction (LCR). In this approach, two sets of sequence-specific oligos are employed for each target region of a double-stranded nucleic acid. One probe set includes first and second oligonucleotides designed for sequence-specific binding to adjacent, contiguous regions of a target sequence in a first strand in the target. The second pair of oligonucleotides is effective to bind (hybridize) to adjacent, contiguous regions of the target sequence on the opposite strand in the target. With continued cycles of denaturation, reannealing and ligation in the presence of the two complementary oligo sets, the target sequence is amplified exponentially, allowing small amounts of target to be detected and/or amplified.

In various embodiments, it will be appreciated that since the selected analytes in the sample can be tested for under substantially uniform temperature and pressure conditions within the substrate, the detection reagents in the various sample chambers should have substantially the same reaction kinetics. This can be accomplished using oligonucleotides and primers having similar or identical melting curves, which can be determined by empirical or experimental methods as are known in the art. In another embodiment, the analyte is an antigen, and the analyte-specific reagents in each detection chamber include an antibody specific for a selected analyte-antigen. Detection may be by fluorescence detection, agglutination, or other homogeneous assay format. As used herein, "antibody" is intended to refer to a monoclonal or polyclonal antibody, an Fc portion of an antibody, or any other kind of binding partner having an equivalent function. For fluorescence detection, the antibody may be labeled with a fluorescent compound such that specific binding of the antibody to the analyte is effective to produce a detectable increase or decrease in the compound's fluorescence, to produce a detectable signal (non-competitive format). In an alternative embodiment (competitive format), the detection means includes (i) an unlabeled, analyte-specific antibody, and (ii) a fluorescer-labeled ligand which is effective to compete with the analyte for specifically binding to the antibody. Binding of the ligand to the antibody is effective to increase or decrease the fluorescence signal of the attached fluorephore. Accordingly, the measured signal can depend on the amount of ligand that is displaced by analyte from the sample. In a related embodiment, when the analyte is an antibody, the analyte-specific detection reagents include an antigen for reacting with a selected analyte antibody which may be present in the sample. The reagents can be adapted for a competitive or non-competitive type format, analogous to the formats discussed above. Alternatively, the analyte-specific reagents can include a mono- or polyvalent antigen having one or more copies of an epitope which is specifically bound by the antibody-analyte, to promote an agglutination reaction which provides the detection signal.

In various embodiments, the selected analytes can be enzymes, and the detection reagents include enzyme substrate molecules which are designed to react with specific analyte enzymes in the sample, based on the substrate specificities of the enzymes. Accordingly, detection chambers in the device may each contain a different substrate or substrate combination, for which the analyte enzyme(s) may be specific. This embodiment is useful for detecting or measuring one or more enzymes which may be present in the sample, or for probing the substrate specificity of a selected enzyme. Examples of detection reagents include chromogenic substrates such as NAD/NADH, FAD/FADH, and various other reducing dyes, for example, useful for assaying hydrogenases, oxidases, and enzymes that generate products which can be assayed by hydrogenases and oxidases. For esterase or hydrolase (e.g., glycosidase) detection, chromogenic moieties such as nitrophenol may be used, for example.

In various embodiments, the analytes are drug candidates, and the detection reagents include a suitable drug target or an equivalent thereof, to test for binding of the drug candidate to the target. It will be appreciated that this concept can be generalized to encompass screening for substances that interact with or bind to one or more selected target substances. For example, the assay device can be used to test for agonists or antagonists of a selected receptor protein, such as the acetylcholine receptor. In a further embodiment, the assay device can be used to screen for substrates, activators, or inhibitors of one or more selected enzymes. The assay may also be adapted to measure dose-response curves for analytes binding to selected targets. The assays also may be immunoassays.

Reference will now be made to various exemplary embodiments, examples of which are illustrated in the accompanying drawings. Wherever possible, the same reference numbers are used in the drawings and the description to refer to the same or like parts.

Figure 2A:
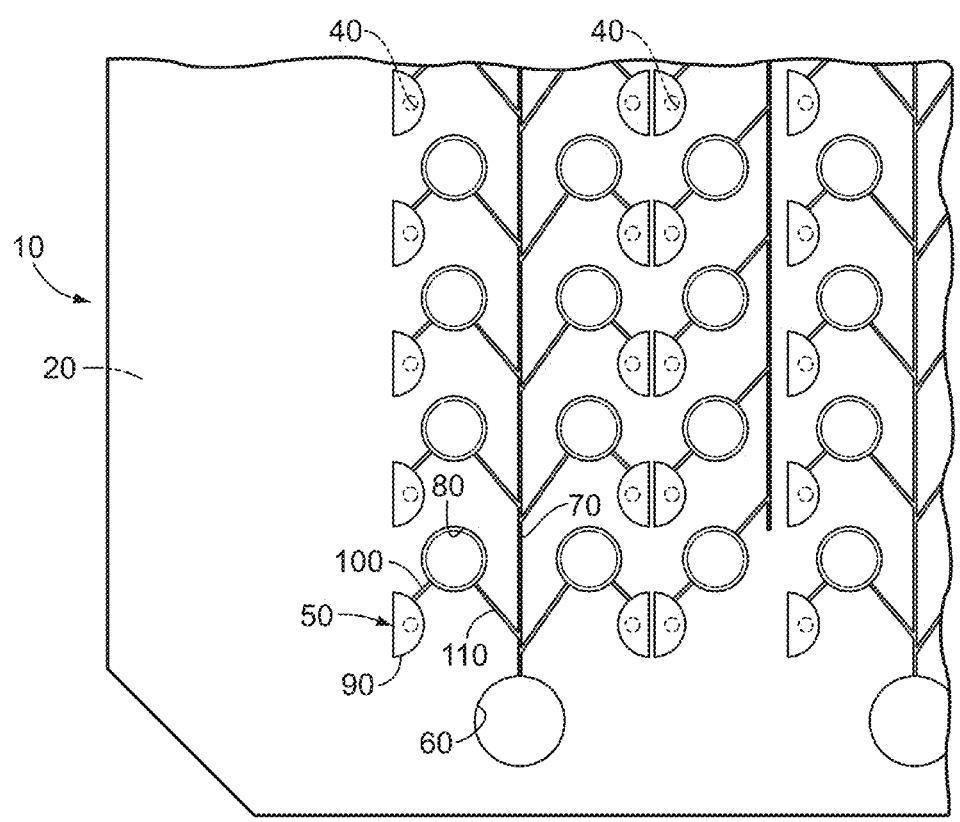
FIG. 2A illustrates a top view of a substrate for biological analysis according to various embodiments of the present teachings
Figure 2B:
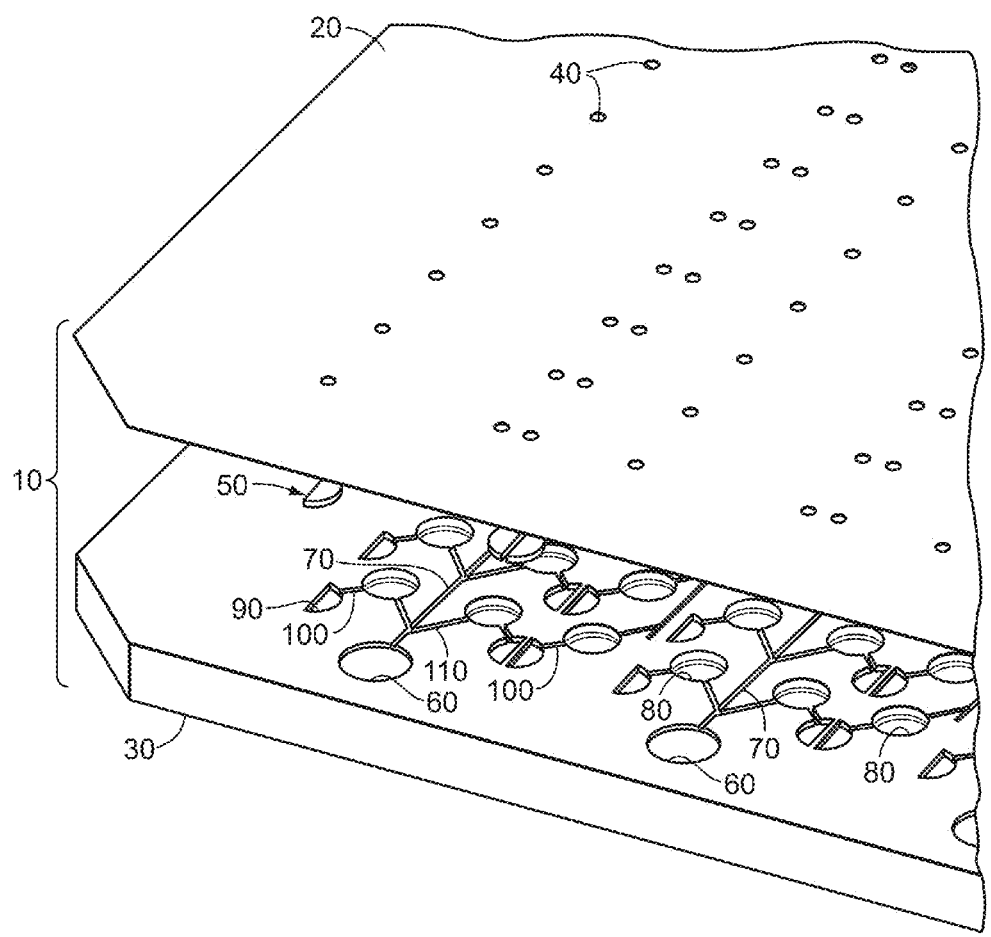
FIG. 2B illustrates an exploded perspective view of a substrate for biological analysis according to various embodiments of the present teachings.

In various embodiments, as illustrated in FIG. 1, the substrate 10 has an array of features providing parallel processing of several samples. The substrate can have dimensions, for example, 127.0 millimeters by 85.7 millimeters providing 384 sample chambers. FIG. 2A illustrates a portion of substrate 10 showing the features. The top view is through the film 20 shown in ghost lines. FIG. 2B illustrates the exploded view showing film 20 with vents 40 aligning with base 30 and gas-permeable membranes 50.

Sample chambers 80 form a regularly spaced array. Sample introduced in sample ports 60 flows to main channels 70 and from there to sample introduction channels 110 into sample chambers 80. Each sample chamber 80 is connected to venting channel 100 which joins venting chamber 90 with sample chamber 80. Venting chamber 90 contains gas-permeable membranes 50 and aligns with vents 40. The membrane typically has a burst pressure of greater than 6 psi. In various embodiments, the film 20 can be a PSA film with laser or mechanically punched vent 40. A membrane layer can be bound to the PSA film 20 and dye cut portions of the membrane layer can be removed leaving gas-permeable membranes 50. The base 30 can be injection molded or etched. The PSA film 20 with gas-permeable membranes 50 attached can then be aligned with the base 30 and laminated together. In various embodiments, the substrate can be mated with a plate providing a plurality of contacts to provide uniform pressure across the substrate where the contacts do not provide substantial thermal transfer between the substrate and the plate relative to the thermal transfer at the surface of the substrate opposite to the plate. The plate can have through holes to permit light to pass from the sample chambers to a detector for detection. The plate is described in U.S. Pat. Pub. No. 2001/0029794.

Examples of suitable membranes include gas-permeable membranes and/or porous membranes. For example, suitable porous membranes may include Gortex® and other similar materials known in the art of micro-porous membranes. Suitable gas permeable membranes may include, for example, PDMS membranes. The membrane materials also can be liquid impermeable to prevent a sponging effect of the liquid that can reduce the volume in the sample chamber. Some examples of suitable porous membrane materials are described in U.S. Pat. No. 5,589,350 and some examples of suitable gas-permeable membrane materials are described in U.S. Pat. Pub. No. 2005/0164373 Titled "Diffusion-Aided Loading System for Microfluidic Devices," the entire disclosures of both of which are incorporated by reference herein.

Figure 3A:
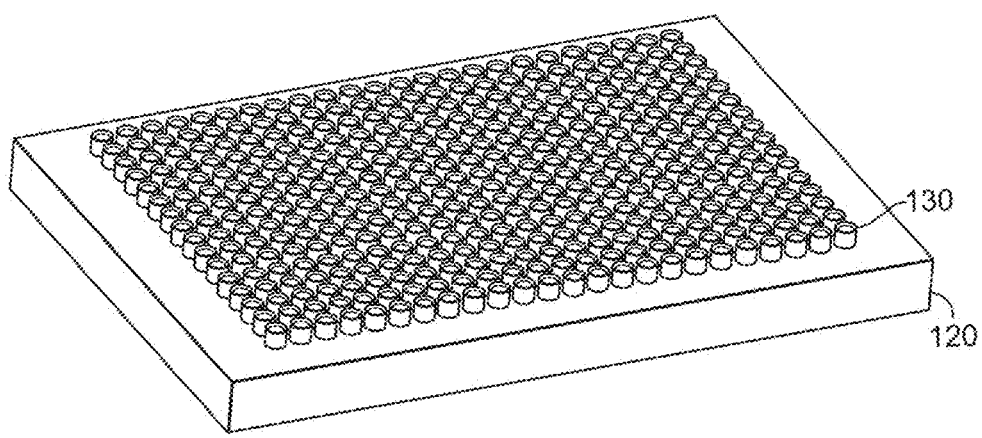
FIGS. 3A-3B illustrate a perspective view with magnified section of a sealing plate according to various embodiments of the present teachings.
Figure 3B:
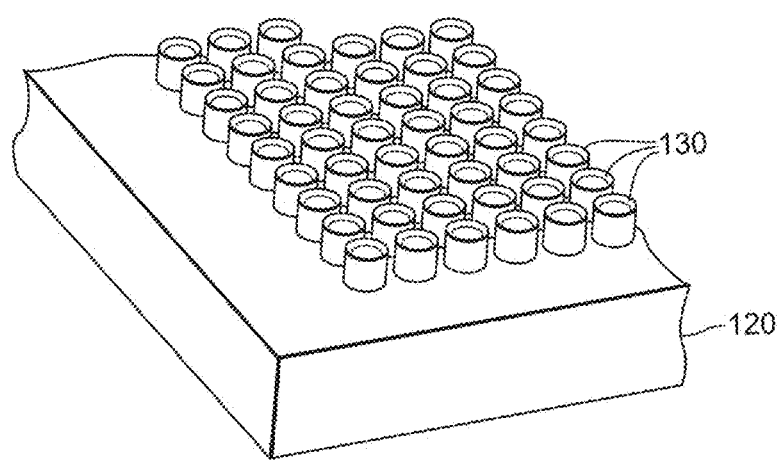
Figure 4:
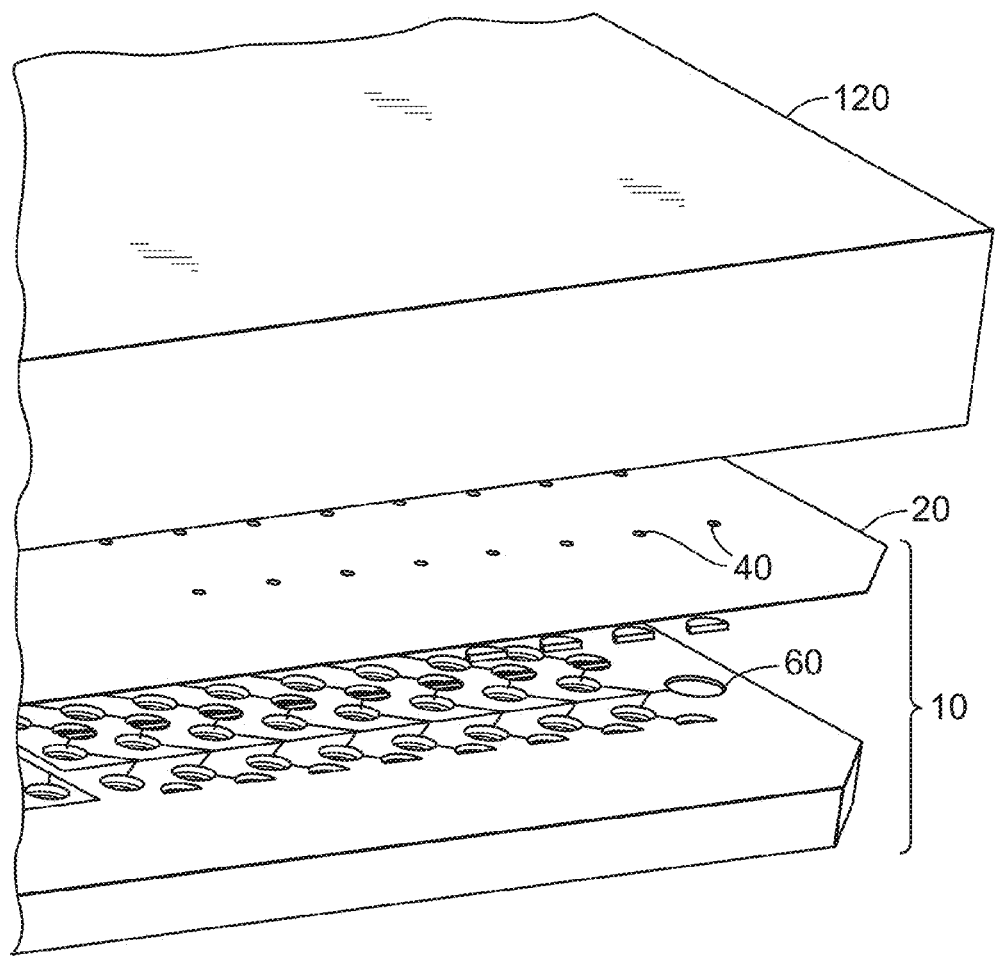
FIG. 4 illustrates an exploded perspective view of a substrate for biological analysis with a sealing plate according to various embodiments of the present teachings.
Figure 5:
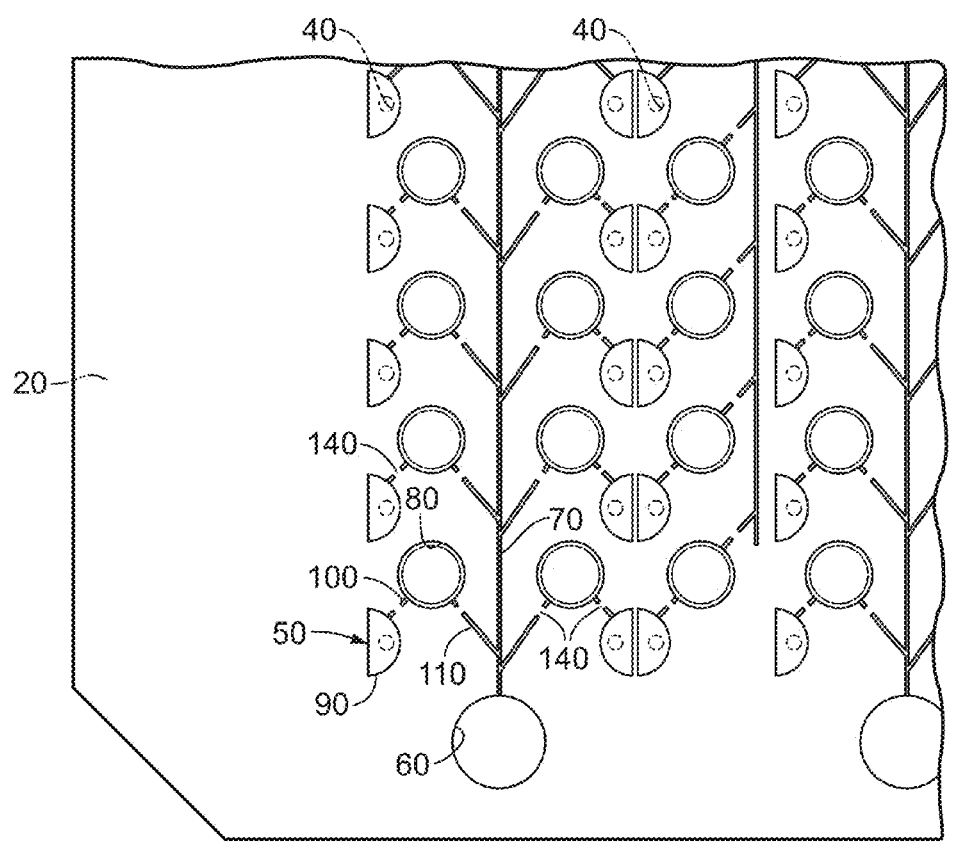
FIG. 5 illustrates top view of a substrate for biological analysis according to various embodiments of the present teachings.
Figure 6:
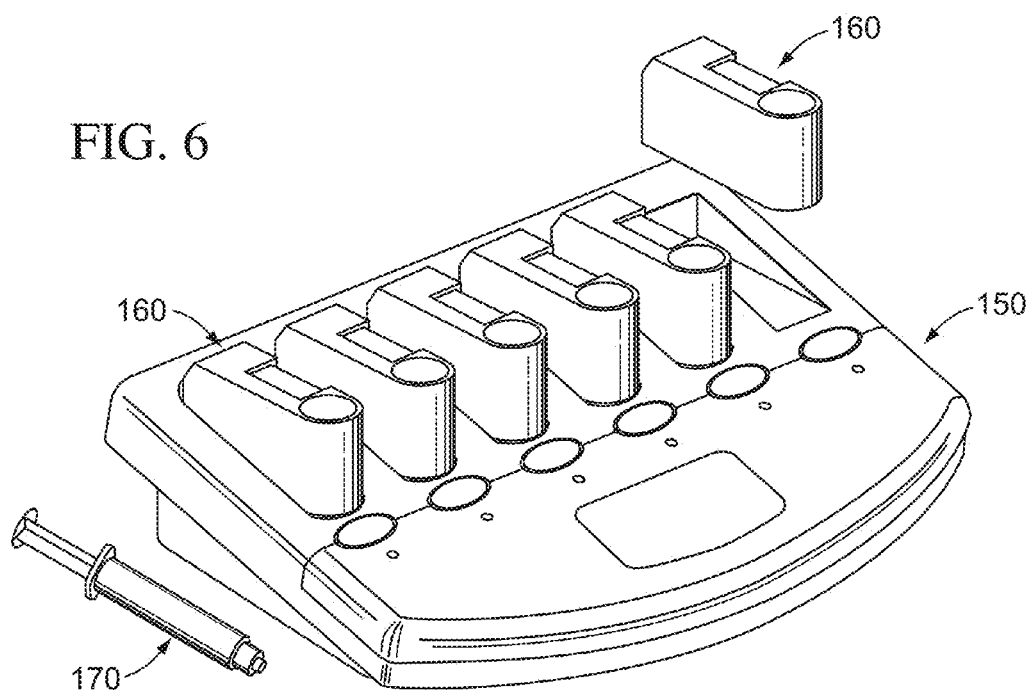
FIG. 6 illustrates a perspective view of an instrument for biological sample preparation including six fluidic cartridges according to various embodiments of the present teachings.

In various embodiments, as illustrated in FIGS. 3A-3B, the sealing plate 120 has a plurality of sealing protrusions 130 such that each protrusion can align with a sample chamber. The sealing plate 120 can be a thermal transfer die to isolate each of the sample chambers. The sealing protrusions can have dimensions of about, for example, 2.5 millimeters. FIG. 4 illustrates the alignment with substrate 10. Sealing plate 120 seals sample introduction channels 110 and venting channels 100 as shown in FIG. 5 by gaps 140.

Figure 3C:
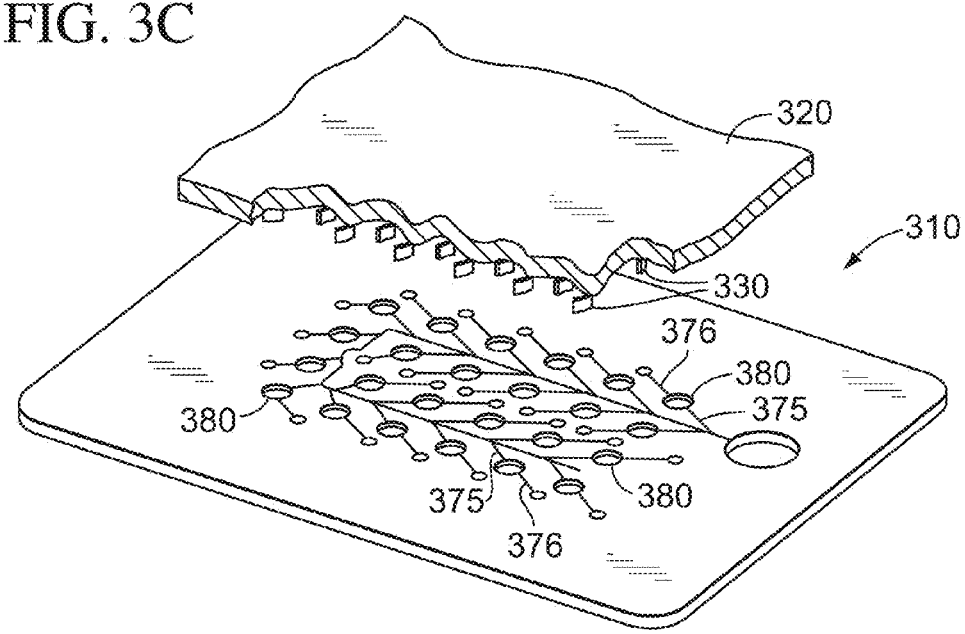
FIG. 3C is a partial perspective view of another sealing plate and substrate according to various embodiments of the present teachings.
Figure 3D:
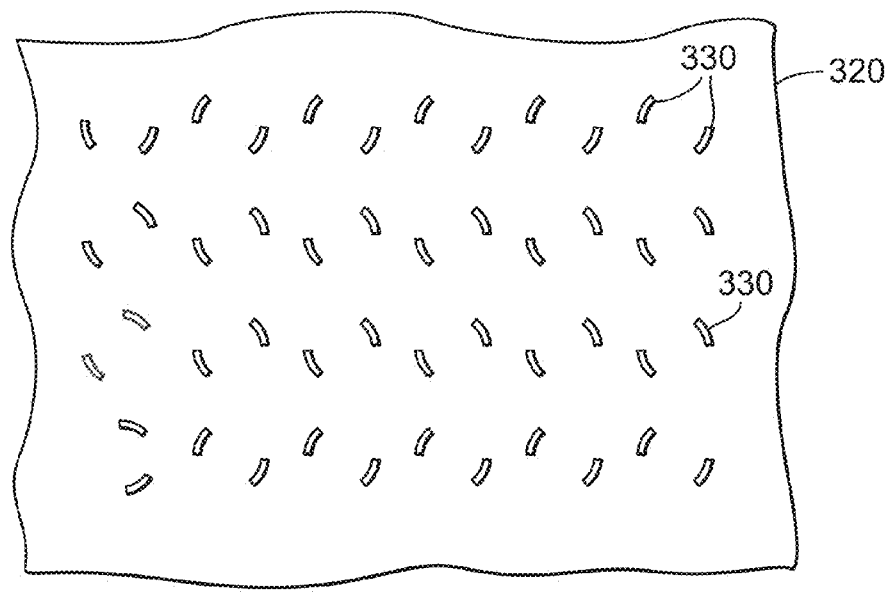
FIG. 3D is a partial view of the sealing plate of FIG. 3C from the protrusion side of the plate.

FIGS. 3C and 3D show another sealing plate according to exemplary embodiments of the teachings herein. FIG. 3C shows an isometric perspective view of the sealing plate 320 in alignment for sealing a substrate 310. FIG. 3D shows a view of the surface of the sealing plate 320 having the protrusions 330 thereon. The sealing plate 320 has a plurality of sealing protrusions 330 in the form of substantially arc-shaped pins. The sealing protrusions 330 are configured and arranged on the plate 320 such that when the plate 320 is aligned with the substrate 310, the protrusions 330 intersect the sample introduction and outlet (venting) channels 375 and 376 to seal the sample chambers 380. Rather than encircling the entire sample chambers 380, the sealing protrusions 330 extend just enough to contact the area of the substrate 310 around the sample chambers 380 in the regions of the channels 375 and 376 to perform the sealing function. Because the protrusions 330 contact relatively small, focused regions of the substrate 310 during sealing, less force on the sealing plate 320 may be required.

Figure 29:
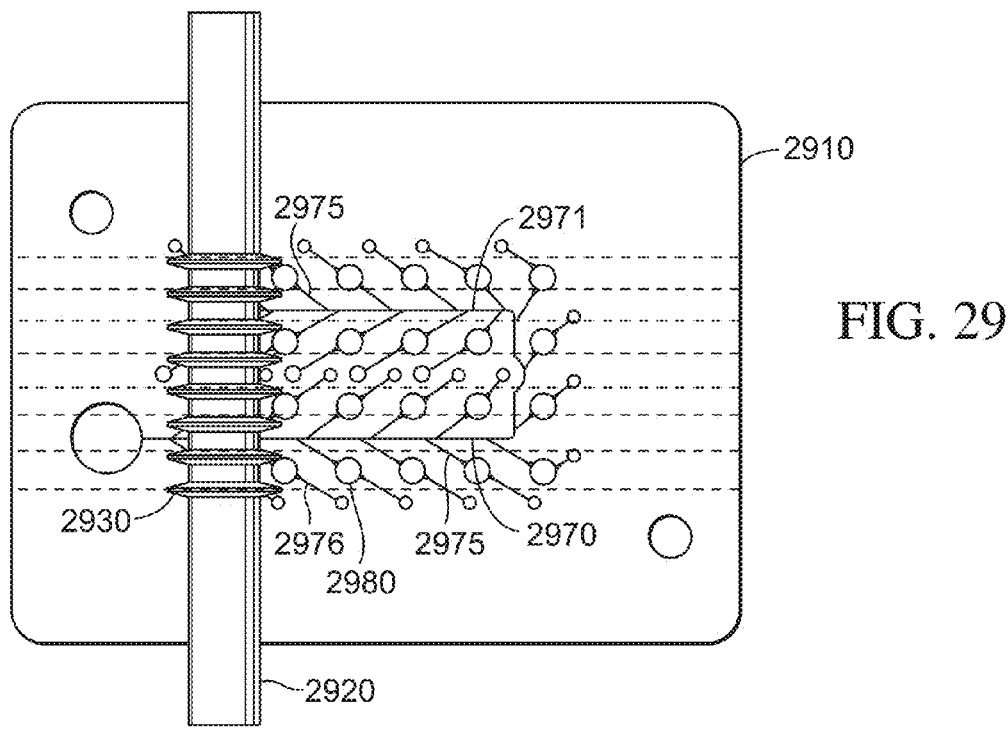
FIGS. 29 and 30 are top and perspective views of a sealing roller for sealing a substrate according to various embodiments of the present teachings.
Figure 30:
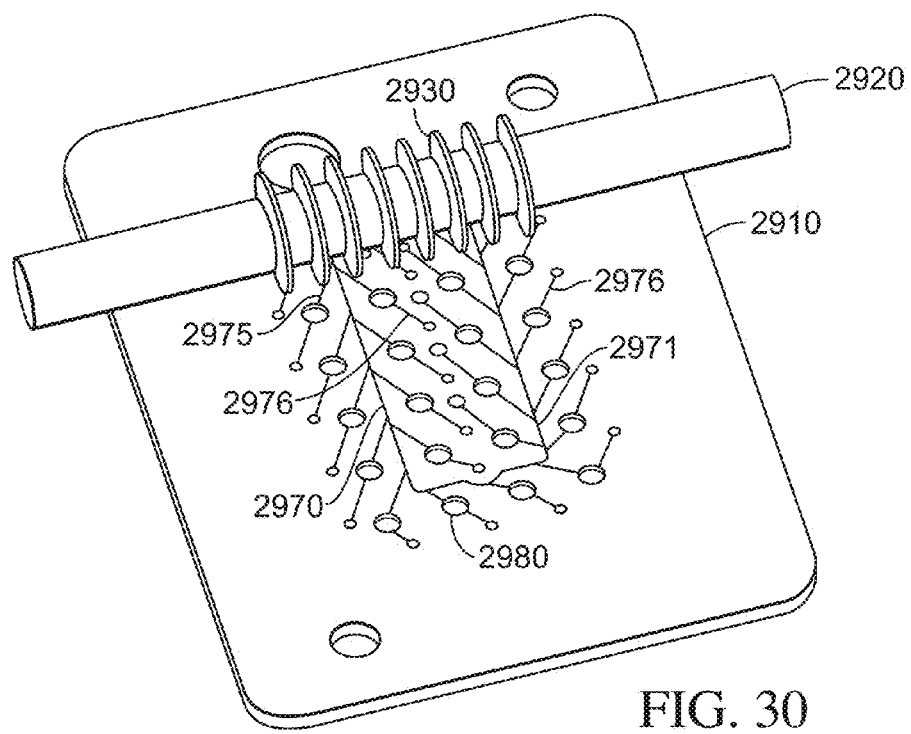

FIGS. 29 and 30 depict an exemplary embodiment of another instrument that may be useful for sealing the sample chambers 2980 of a substrate 2910 (e.g., staking the substrate) and may be used instead of a sealing plate like that shown in FIGS. 3A-3B. The sealing instrument embodiment of FIGS. 29 and 30 includes a roller 2920 provided with a plurality of sealing protrusions in the form of circumferential disks 2930 spaced from each other along the longitudinal axis of the roller 2920. Sealing of the substrate chambers 2980, for example, in a manner similar to that shown in FIG. 5 by the gaps 140, may occur by rolling the disks 2930 across the substrate 2910 using a sufficient force. For example, the force may be enough to force an adhesive (e.g., a PSA) into the inlet and outlet channels 2975 and 2976 and/or otherwise deform the channels 2975 and 2976 at the locations that the disks 2930 cross over the channels 2975 and 2976 to prevent flow communication between the channels 2975, 2976 and the sample chambers 2980.

The number and positioning (spacing) of the disks 2930 may be selected such that the roller 2920 may pass over the substrate 2910 once to isolate all of the sample chambers 2980, sealing both inlet and outlet channels 2975 and 2976 simultaneously. The number and positioning of the disks 2930 may thus depend on a variety of factors, including but not limited to, for example, the number of sample chambers, the arrangement of the sample chambers, and the arrangement of the inlet channels and outlet channels. According to various exemplary embodiments, the number of disks may be reduced by staking the shared main fluid channels 2970 and 2971 between two lines of chambers 2980 in the embodiment of FIGS. 29 and 30 instead of the inlet channels 2975 of each of the chambers 2980. In various embodiments, it may be desirable to provide a main fluid channel (or main fluid channels) with a zig-zag configuration so that it can be intersected and sealed (staked) multiple times, for example, with one pass of the roller 2920 over the substrate 2910. Further, in the case of shared outlet (e.g., venting) channels between adjacent rows of chambers, the number of disks also may be reduced.

Figure 31:
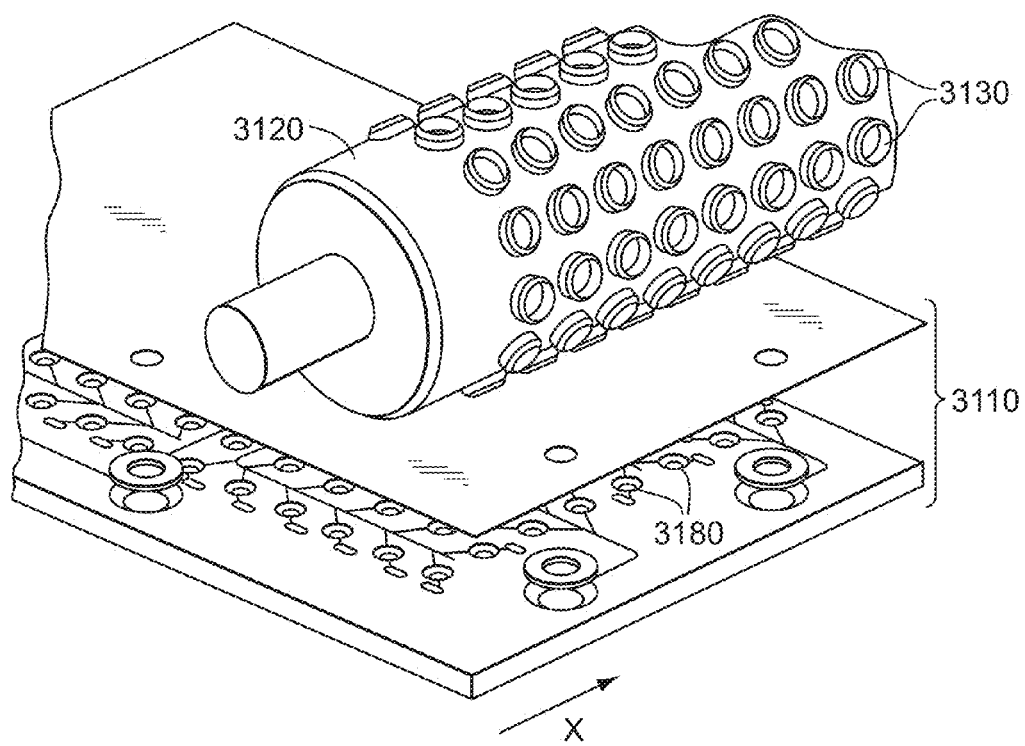
FIG. 31 is a perspective view of another sealing roller according to various embodiments of the present teachings.

With reference now to FIG. 31, another exemplary embodiment of a sealing instrument in the form of a roller 3120 is depicted. In the embodiment of FIG. 31, the roller 3120 includes a plurality of sealing protrusions in the form of circular pins 3130 provided around the outer circumference of the roller 3120. The pins 3120 may be aligned over a row of chambers 3180 in a substrate 3110 and seal the chambers 3180 in a manner similar to that depicted by the gaps 140 in FIG. 5. However, rather than sealing all of the chambers 3180 of the substrate 3110 at the same time, like the sealing plate of FIGS. 3A and 3B, a few chambers 3180 get sealed as the roller 3120 passes over the substrate 3110. This requires less force to seal the chambers, since not all of the chambers 3180 are sealed at once. Although each chamber 3180 in a row of chambers 3180 (e.g., x-direction in FIG. 31) may be sealed simultaneously, it is also envisioned that the roller 3120 may be moved such that less than all chambers in a row are sealed at the same time as the roller 3120 passes over the substrate 3110. For example, the roller 3120 of FIG. 31 may be aligned over a portion of the substrate 3110 (e.g., shifted in the x direction shown in FIG. 31) so as to seal only some chambers 3180 in each row sealed with a pass of the roller 3120. The roller may then be shifted again over another portion of the substrate 3110 and passed over the substrate 3110 again to seal the remaining chambers 3180 in each row.

It should be understood that the protrusions provided on the rollers in the embodiments of FIGS. 29-31 may have a variety of different sizes, shapes, and arrangements and those of ordinary skill would understand how to make rollers with sealing protrusions of other configurations and arrangements to perform desired sealing of the sample chambers of a substrate. By way of example and not limitation, it is envisioned that the sealing protrusions 3130 of FIG. 31 may be replaced with the sealing protrusions 330 of FIG. 3C, with the arrangement of the protrusions 330 on the roller being selected so as to seal the sample introduction and venting channels from flow communication with the sample chambers of a substrate.

In the exemplary embodiments of FIGS. 3A-3D and 29-31, the force on the sealing plates 120 and 320 and rollers 2920 and 3120 required to effect sealing of the substrate 10, 310, and 2910 and 3110 may be relatively low, for example, due to the relatively small contact area between the roller and the substrate during sealing. Further, to reduce the force applied to achieve sealing, plural plates 120 and 320 or rollers 2910 and 3110 may be used, with less sealing protrusions provided on each of the plural rollers or plates. In such a case, the positioning and/or shape of the protrusions on each of the plural rollers or plates used to perform complete sealing of all of the chambers of the substrate may be selected so as to achieve sealing of some portions of the substrate with a first roller or plate and other portions of the substrate with a second roller or plate, etc. By way of example, the sealing protrusions on a first roller or plate may seal the outlet (e.g., venting channels) leading from the sample chambers, while the sealing protrusions on a second roller or plate may seal the inlet channels leading to the sample chambers. Those having ordinary skill in the art would understand a variety of numbers and configurations of rollers and/or plates and sealing protrusions on those rollers and/or plates to accomplish desired sealing of the substrate with a desired force applied.

In addition, it should be understood that in the embodiments of FIGS. 29-31, the rolling of the rollers 2920 and 3120 over the substrates 2910 and 3110 is intended to refer to relative motion between the rollers 2920 and 3120 and the substrates 2910 and 3310. Thus, either the rollers 2920 and 3120 can move while the substrates 2910 and 3110 remain stationary, vice versa, or both the rollers 2920 and 3120 and the substrates 2910 and 3110 may move. In another exemplary aspect, the rollers 2920 and 3120 may be idle or can drive the motion of the substrates 2910 and 3110. Likewise, in the embodiments of FIGS. 3A-3D and 4, the movement of the plates 120 and 320 and the substrates 10 and 310 is relative.

It also is envisioned that, in the case of an integrated instrument where the substrate passes through various stations, the sealing rollers or plates of the may be placed in the transfer path of the substrate. For example, the sealing rollers or plates may be placed at a location after the substrate has been filled (e.g., at a filling station) and before the next station, such as, for example, a thermocycling block or instrument delivery port.

The exemplary sealing roller embodiments of FIGS. 29-31 may be relatively easy to manufacture. They also may facilitate appropriate alignment of the roller with the substrate during sealing, as alignment is necessary only along the longitudinal axis of the roller and not along the longitudinal axis of the substrate.

Figure 7:
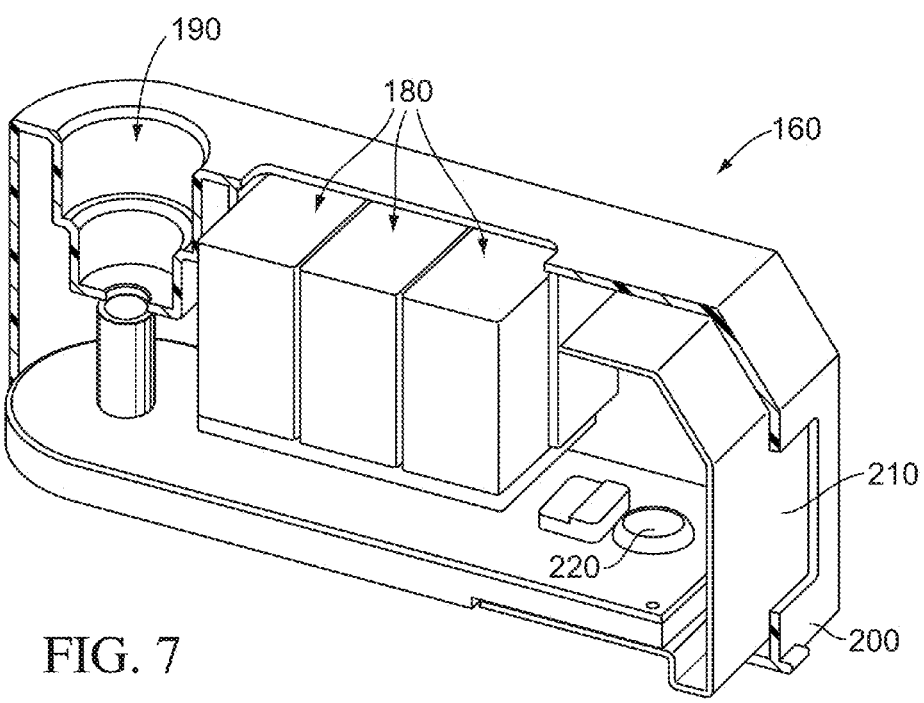
FIG. 7 illustrates a cut-away perspective view of a cartridge for biological sample preparation according to various embodiments of the present teachings.

In various embodiments, sample preparation instrument 150 can take raw biological sample from syringe 170 and prepare the sample for introduction into substrate 10. Preparation of sample can include extraction of nucleic acids and pre-treatment for detection as described above. The instrument 150 docks with several cartridges 160 that provide preparation. FIG. 7 illustrates the cartridge 160. Sample syringe inlet 190 introduces the raw biological sample into the cartridge. Pre-filled reagent reservoirs 180 provide the analyte-specific reagents for the assay to be performed on substrate 10. The back of cartridge housing 200 is open to permit interconnection of a flex circuit PCB device 210 with instrument 150.

Various other exemplary embodiments may provide mechanisms for sealing, venting, controlling pressure, sample preparation, mixing, and/or other features useful in multiple analyte detection in a substrate in accordance with teachings of the disclosure and are described in further detail below.

As discussed above, once the sample chambers of a substrate have been filled, it may be desirable to seal filled chambers from flow communication with each other and the various distribution channels. Such sealing may be desirable, for example, before various operations, such as, for example, PCR, may be performed, and to prevent cross-contamination between wells. It also may be desirable to provide a mechanism for sealing that is relatively easily performed by a user of the biological testing device. Further, it may be desirable to provide a mechanism for sealing the substrate that does not require the use of sensors, heaters, and/or other components that may be relatively difficult and costly to implement.

Figure 8A:
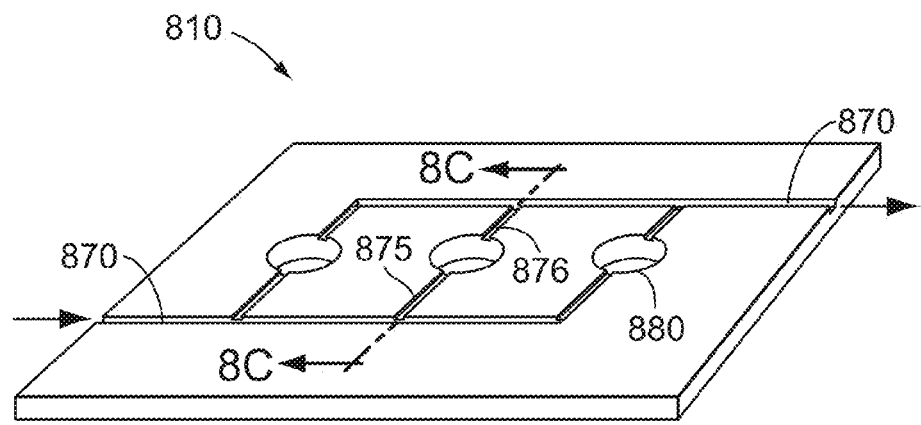
FIG. 8A illustrates a perspective view of a substrate for biological analysis according to various embodiments of the present teachings.
Figure 8B:
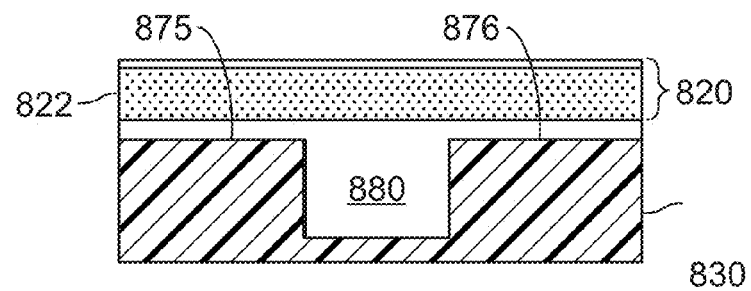
FIGS. 8B and 8C illustrate cross-sectional views of FIG. 8A taken through line 8C-8C according to various embodiments of the present teachings.
Figure 8C:
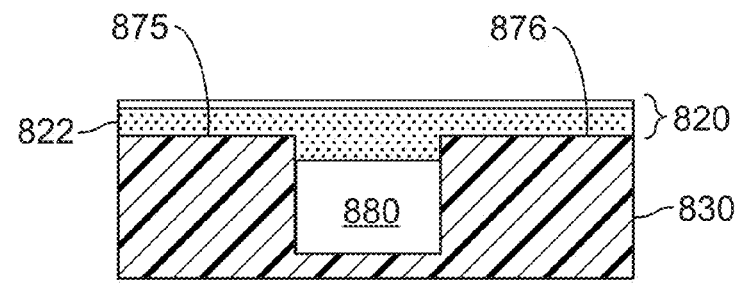

Referring to FIGS. 8A-8C, an exemplary embodiment of a substrate 810 is depicted. It should be understood that the substrate 810 depicted in FIGS. 8A-8C is schematic for purposes of simplifying the drawings. Thus, FIG. 8A shows only three sample chambers 880 having inlet channels 875 and outlet (venting) channels 876 connected to main fluid channels 870. The arrows in FIG. 8A illustrate the direction of flow of sample for filling the sample chambers 880. It should be understood that the substrate 810 could include an array of sample chambers 880 connected by fluid distribution channels and may also include venting chambers (not shown in FIG. 8A). By way of example, the substrate 810 may include features similar to that shown in FIG. 1 or may have other configurations in accordance with the teachings herein.

The substrate 810 may include a base 830, which may have a configuration like the bases described above. The base 830 may be covered with an adhesive-backed film 820. In various embodiments, the adhesive-backed film 820 may be, for example, a PSA film. With reference to the cross-section of the substrate 810 shown in FIG. 8B taken through line 8C-8C in FIG. 8A, prior to filling the substrate 810 with biological sample, the adhesive-backed film 820 may be loosely applied over the base 830 such that the channels 875 and 876 and sample chambers 880 are in flow communication, thereby permitting sample to be injected into the channels 875, 876, and 870 to fill the sample chambers 880. After the sample chambers 880 have been filled and it is desired to seal the chambers 880, pressure may be applied to the film 820 so as to cause the adhesive 822 of the adhesive-backed film 820 to be forced into the channels 870, 875 and 876 and partially into the chambers 880, as depicted in FIG. 8C. Forcing the adhesive into the channels 870, 875, and 876 closes the channels 890, thereby preventing flow communication between the chambers 880 and between the channels 875, 876, and 870, and chambers 880.

Figure 9A:
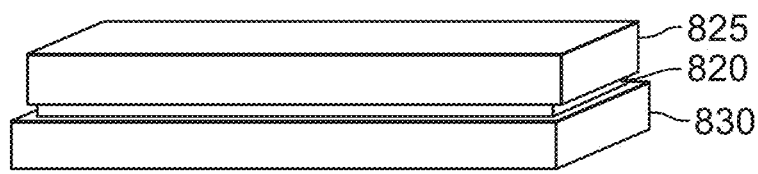
FIGS. 9A-9B illustrate perspective views of exemplary embodiments for sealing the substrate of FIGS. 8A-8C and 10A-10C.
Figure 9B:
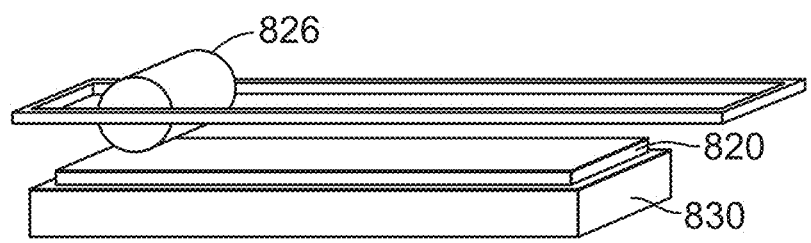

By way of example, in the case of a consumable product, the adhesive-backed film 820 may be loosely applied during manufacturing and a user of the substrate 810 may apply the pressure required for sealing after loading the substrate with sample. Various mechanisms may be used to apply pressure, for example, a substantially uniform pressure, over substantially the entire adhesive-backed film. For example, the pressure could be applied by the user's hand pressing on the film 820. Other techniques for applying the pressure include using a motorized stepping plate 825 (as schematically depicted in FIG. 9A) or a motorized roller 826 (as schematically depicted in FIG. 9B). The plate 825 and/or motorized roller 826 may be provided as part of separate instrumentation or as a separate mechanism to be used with the substrates, and may be used to seal numerous substrates. Those having ordinary skill in the art would understand various mechanisms that may be used to apply a sufficient force across the film layer 820.

According to various exemplary embodiments, in addition or as an alternative to providing pressure to force the adhesive 822 to fill the channels 875, 876, and 870, heat also may be used to facilitate the filling of the channels with the adhesive 822. However, it is envisioned that the use of heat is not necessary. The appropriate thickness of the adhesive layer 822 may be selected so as to perform adequate channel closing without injecting too much adhesive into the chambers 880. By way of example, the thickness of the adhesive layer 822 may be such that the entire depths of the channels are filled with adhesive, leaving no air pockets within the channels. Also, if sample is displaced during sealing, it may be desirable to provide an adhesive thickness that results in a substantially consistent amount of fluid being displaced, while also minimizing the amount of wasted sample due to displacement.

Figure 10A:
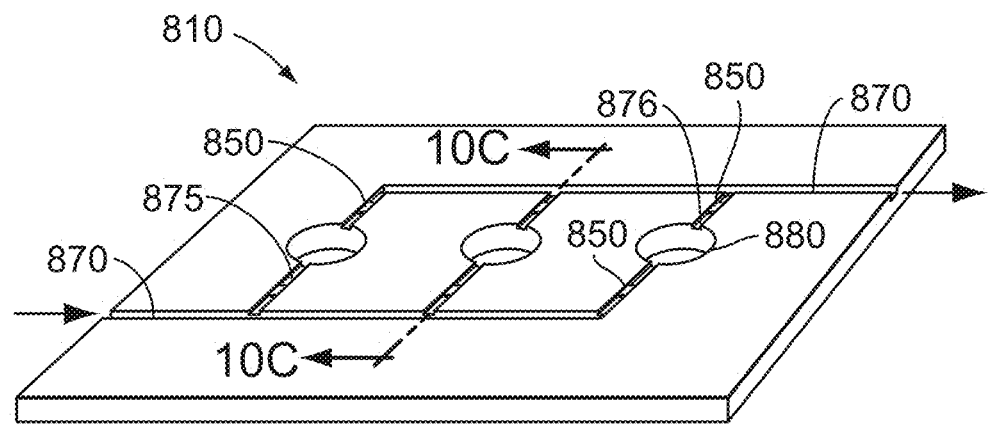
FIG. 10A illustrates a perspective view of a substrate for biological analysis according to various embodiments of the present teachings.
Figure 10B:
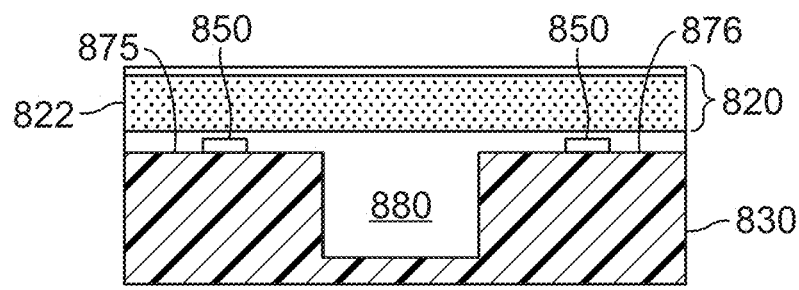
FIGS. 10B and 10C illustrate cross-sectional views of FIG. 10A taken through line 10C-10C according to various embodiments of the present teachings.
Figure 10C:
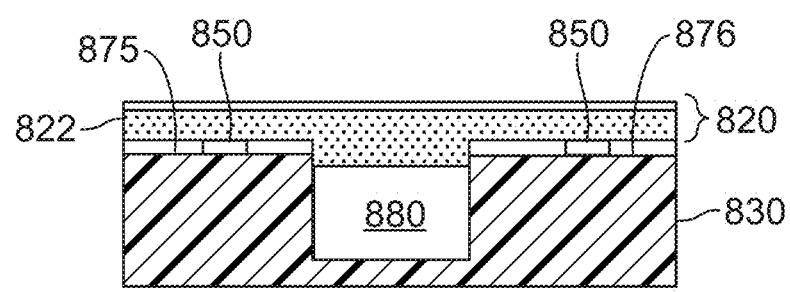

FIGS. 10A-10C illustrate another exemplary embodiment that uses the adhesive of an adhesive-backed film to seal the channels from the chambers in a biological testing device. With reference to FIG. 10A, a protruding portion 850 is provided in a portion of each of the inlet and outlet channels 875 and 876 that lead to and from the chambers 880. As shown in the cross-sectional view of FIG. 10B, the adhesive-backed film 820 may be lightly applied prior to filling the substrate 810 with the sample, such that the channels 875, 876 and 870 may be in flow communication with the chambers 880, as described above with reference to FIG. 8B. Once the substrate 810 has been filled with fluid (e.g., biological sample) as desired, a pressure may be applied, for example, substantially uniformly over substantially the entire surface of the film 820. The pressure may be applied via any mechanism, including those described above with reference to the embodiments of FIGS. 8 and 9, and, optionally, heat may be applied. As a result of the pressure on the film 820, the adhesive 822 of the film 820 will be forced into the channels 875, 876 and 870. However, due to the presence of the protruding portions 850, the adhesive 822 may come into contact with the protruding portions 850 to seal the channels 875 and 876 from flow communication with the chamber 880 without filling the entire channels 875 and 876. The adhesive 822 may make substantially uniform contact over substantially the entire surface of the protruding portion 850, as shown in FIG. 10C. Due to the adhesive 822 making contact with the protruding portion 850 and not filling the entire channel depth, sealing may be implemented with much of the sample remaining in the channels 875 and 876 since a relatively small amount of sample will may be displaced due to the entry of the adhesive throughout the channels 875 and 876. For example, the relatively small amount of sample that is displaced may be so as to slightly deform the film layer 820. Further, sealing may be relatively easy to accomplish since the adhesive layer may only need to contact the protruding portions 850, rather than filling the entire channels 875 and 876.

According to various exemplary embodiments, the protruding portions 850 may be made of the same material as the base 830 and may be formed via injection molding of the base 830. Other materials and techniques for forming the protruding portions 850 also may be used and would be understood to those having ordinary skill in the art. By way of example, and not limitation, the protruding portions 850 may have a height equal to about one-half the depth of the channels 875 and 876, and may span across the width of the channels (e.g., in the left to right direction shown in FIG. 10A).

In various exemplary embodiments, for example, when using a motorized roller 826 such as that depicted in FIG. 9B to apply pressure to the adhesive-backed film 820, the roller 826 may be oriented such that its longitudinal axis (e.g., its axle) is nonparallel (for example, perpendicular) to the channels 875 and 876 in which the protruding portions 850 are placed when performing sealing. With such a nonparallel orientation to a channel during sealing, the roller 826 may contact only a relatively small part of the channels 875 and 876 at a time, thereby displacing a relatively small amount of fluid (e.g., sample), if at all, from the channels. In an exemplary embodiment, the roller 826 may be placed at a 45 degree angle to both axes of the substrate. Placing the roller 826 in a parallel orientation to a channels 875 and 876 during sealing may cause a relatively large portion of fluid (e.g., sample) in the channels 875 and 876 to be displaced therefrom and may potentially increase the pressure to a sufficient amount so as to break the seal formed between the film 820 and the base 830.

In various embodiments, a stationary rotating cam may be used, for example, instead of the motorized plate or roller of FIGS. 9A and 9B, to apply a pressure to the adhesive film layer of a substrate in order to effect sealing of the sample chambers, for example, of a stationary line of sample chambers. In conjunction with such a motorized rotating cam, a member that applies pressure to substantially the entire film layer prior to the sealing by the cam may be used. By applying pressure to the film layer, a small amount of sample in the sample chambers may move into adjacent channels (e.g., sample introduction (inlet) and venting (outlet) channels). As the rotating cam comes into contact with the substrate to perform the sealing function, the pressure on the film layer applied by the member may be removed at a rate substantially proportional to the application of the pressure exerted by the cam and the volume of the channels that will be reduced due to the adhesive entering the channels. This may allow for accommodation of increased pressure in the sample chambers caused by the sealing operation and provide a defined sample volume in each sample chamber, which may make thermocycling more efficient.

Figure 11:
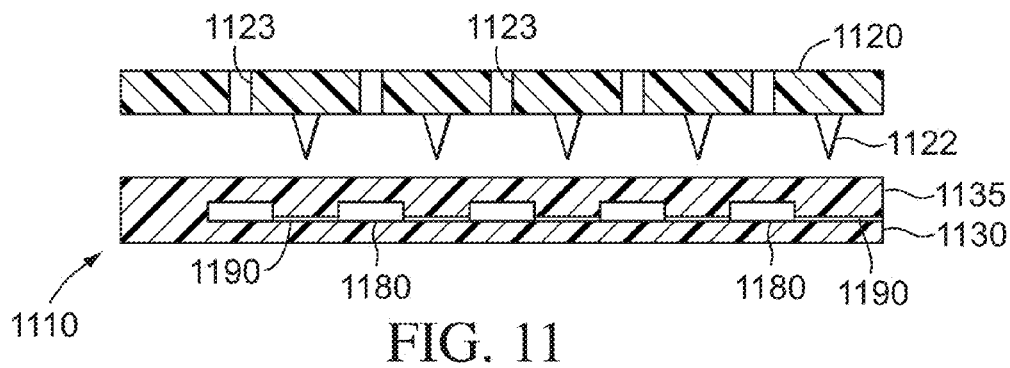
FIG. 11 illustrates a cross-sectional view of a substrate for biological analysis according to various embodiments of the present teachings.
Figure 12A:
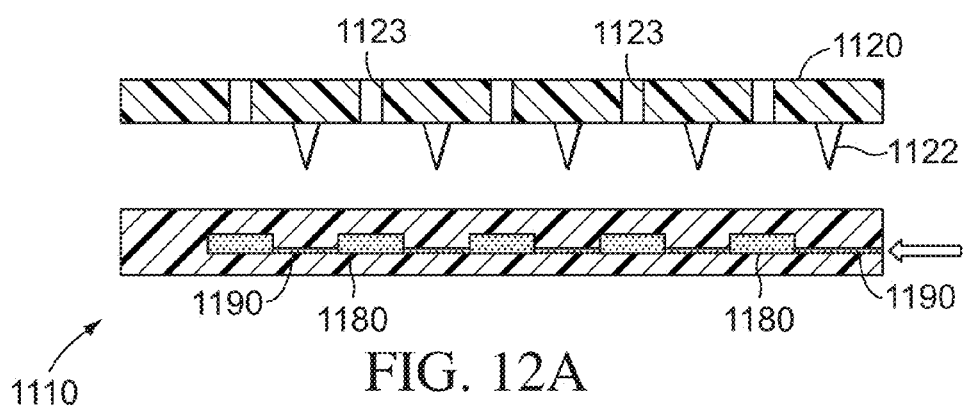
FIGS. 12A-12B are cross-sectional views of filling and sealing the substrate of FIG. 11 according to various embodiments of the present teachings.
Figure 12B:
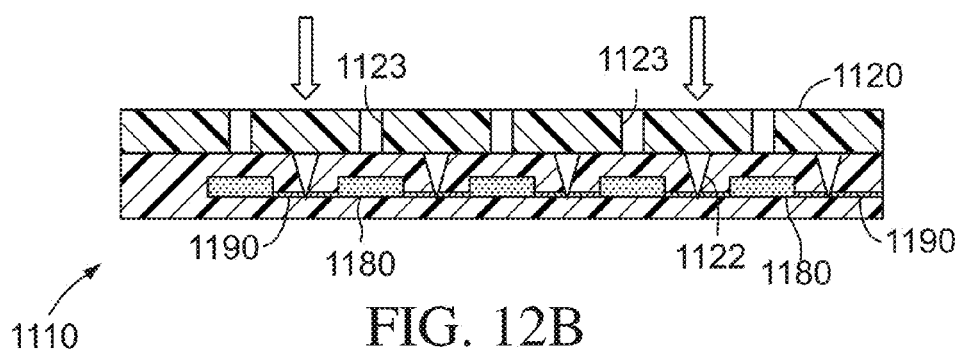

FIGS. 11, 12A, and 12B schematically depict a side cross-sectional view of another exemplary embodiment of an instrument useful for sealing fluid sample chambers in a biological testing device. As shown, the device may include a substrate 1110 that includes a base 1130 and a cover 1135 (e.g., a PSA film layer) for the base 1130 that together define a plurality of channels 1190 in flow communication with a plurality of sample chambers 1180 such that the channels 1190 can deliver sample fluid to and from the sample chambers 1180. For purposes of simplification, the schematic depiction in FIGS. 11, 12A, and 12B show only sample chambers 1180 and introduction and outlet channels 1190 in flow communication with those chambers 1180. It should be understood, however, that the substrate 1110 may include venting chambers, main fluid channels, sample introduction channels, venting channels, a fluid inlet port for supplying fluid to the substrate, etc., in accordance with the teachings herein.

The biological testing device may further include a sealing carrier 1120, having a plate-like structure, that includes a plurality of staking blades 1122 on a side of the carrier 1120 facing the substrate 1110. Prior to filling the substrate 1110, the carrier 1120 may be separated from the substrate 1110 via a temporary mechanical mechanism, such as, for example, a film hinge, or may be separate form the substrate 1110 with no connection. The carrier 1120 may be brought into contact with the substrate 1110 when sealing is desired. In various embodiments, the carrier 1120 and substrate 1110 may be provided with mating pins and holes or other fastening mechanisms that are configured for insertion in one direction but prevent separation in the opposite direction. The carrier 1120 may be separated such that the blades 1122 are above and at a distance from the upper surface (as shown in FIGS. 11 and 12) of the substrate 1110. In this separated configuration, the channels 1190 are in flow communication with the sample chambers 1180 and a biological sample may be loaded into the substrate 1110 via a suitable inlet, as depicted by the arrow in FIG. 12A. It should also be understood that an inlet for fluid supply may be provided on the upper or lower surface of the substrate 1110 via a port (not shown) that is in flow communication with the channel 1190 toward the right hand side of the figures.

Once the sample chambers 1180 of the substrate 1110 have been filled, as shown in FIG. 12A, a force may be applied to the carrier 1120 and/or the substrate 1110 so as to move the carrier 1120 toward the substrate 1110 (e.g., as shown by the arrows in FIG. 12B). The force may be applied via a variety of mechanisms, including but not limited to, for example, a motorized plate, a motorized roller, a clamp, a user's hand, or other suitable mechanisms. The force may be sufficient to bring the carrier 1120 into contact with the substrate 1110 (for example, by breaking or deforming the mechanical mechanism that initially separates the carrier 1120 from the substrate 1110). With the carrier 1120 and substrate 1110 in the contacting position, as shown in FIG. 12B, the staking blades 1122 are driven into the substrate 1110 at a location of the channels 1190 proximate the chambers 1180. In various embodiments, each channel 1190 may be aligned with a differing blade 1122. In other embodiments, a single blade 1122 may be aligned with a plurality of channels 1190, for example, the blades 1122 in FIGS. 11. 12A and 12B may extend into the drawing sheet to seal differing channels positioned along a direction into the drawing sheet.

The blades 1122 may pierce, deform, or otherwise alter the structure of the substrate 1110 at the locations so as to prevent flow communication between the chambers 1180 and between the channels 1190 and the chambers 1180. By way of example, the blades 1122 may pierce through film layer 1135 and enter the channels 1190 so as to block flow between the channels 1190 and corresponding chambers 1180. In addition to blocking flow communication between the channels 1190 and the chambers 1180, the carrier 1120 may be configured to provide a seal (e.g., prevent flow communication) between the substrate 1110 and the exterior, for example, through the fill port in the substrate 1110.

The staking blades 1122 may be positioned relative to the carrier 1120 such that they are properly aligned with the channels 1190 as desired to prevent flow communication between the channels 1190 and the sample chambers 1180 when the carrier 1120 is placed into the contacting position with the substrate 1110 via the applied clamping force. Providing the blades 1122 as part of the carrier 1120 (e.g., an integral part of the carrier 1120) may facilitate manufacturing and alignment of the blades 1122, as the appropriate alignment can be assured prior to sealing the substrate 1110 with the carrier 1120. The appropriate alignment of the blades 1122 with the channels 1190 may ensure reliable sealing of the substrate 1110 and may permit the use of relatively small staking blades 1122. Relatively small staking blades in turn may require less force to drive the blades into the substrate 1110, for example, as compared to larger staking blades. The shape, size, and material of the blades may be selected based on the thickness, material, and other properties of the cover 1135.

The carrier 1120 also may include optical apertures 1123, for example, windows, that are in substantial alignment with the sample chambers 1180 when the carrier 1120 is in the sealing position, as depicted in FIG. 12B. The optical apertures 1123 may thus permit optical detection of the sample chambers 1180 during biological testing/analysis. Other sealing plates according to embodiments of the teachings herein also may include such apertures.

In accordance with various exemplary embodiments, when using the device of FIGS. 11, 12A, and 12B to perform PCR, the substrate 1110 and carrier 1120 may be placed between a clamp and a thermal block of a PCR instrument. When the instrument applies a clamping force via the clamp to the carrier 1120, for example, after the substrate 1110 has been filled with sample as desired, the carrier 1120 may move toward the substrate 1110. As the carrier 1120 moves toward the substrate, any mechanical mechanism that separates the carrier 1120 and the substrate 1110 may fail (e.g., break or deform) such that the carrier 1120 moves into a contacting position with the substrate 1110 and the blades 1122 are driven into the substrate 1110, as depicted in FIG. 12B. The device may be placed between the clamp and thermal block of the PCR instrument either prior to or after filling of the substrate 1110 with sample, however, the clamping force will be applied after filling. It also may be possible to use a clamping device that applies force to one or more sections of the substrate and/or carrier 1120 at a time to reduce the force required for the blades 1122 to penetrate and seal the substrate 1110. Further, in various embodiments, as suggested above, retaining clips or other mechanical connection means may be provided to secure the carrier to the substrate in addition to the blades 1122 themselves holding the carrier 1120 and substrate 1110 together.

In various embodiments, for example, in the case of PCR, the sealing of the substrate sample chambers may be implemented using the thermal block that is placed in contact with the substrate to perform thermocycling. Using the thermal block to perform the sealing function reduces a step in the processing of the substrate, allowing the step of thermocycling and sealing to be performed at the same time. Further, as will be explained, using the thermal block to perform the sealing function may enhance thermal contact and heat transfer between the thermal block and the sample chambers, which may thereby reduce thermocycling times.

Figure 32:
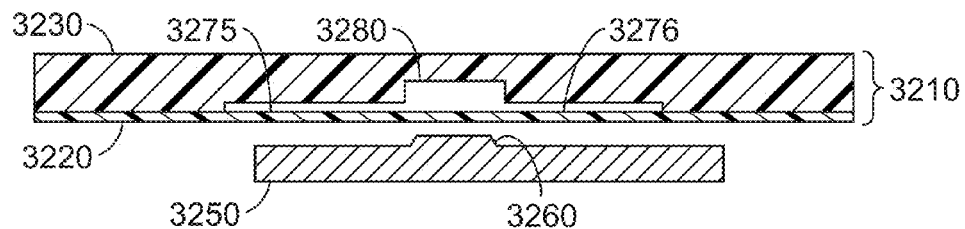
FIGS. 32 and 33 are partial, cross-sectional views of a substrate and a thermal block for sealing a substrate according to various embodiments of the present teachings.
Figure 33:
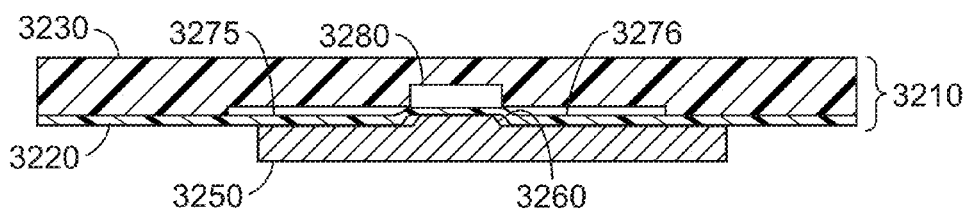

FIGS. 32 and 33 show schematic cross-sectional views of a substrate 3210 including a base 3230 and film layer 3220. The base 3230 may define a plurality of features that, together with the film layer 3220 form a fluid distribution network of fluid distribution channels and chambers, as discussed herein. In the view of FIGS. 32 and 33, for ease of illustration, a single sample chamber 3280 is illustrated with channels 3275 and 3276 leading to and from the chamber 3280. The substrate 3210 may be made of a variety of materials in accordance with the teachings herein.

To perform the sealing function, the thermal block 3250 is provided with a plurality of sealing protrusions (e.g., bumps) 3260 (which may be in the form of an array), only one of which is depicted in FIGS. 32 and 33, that are configured and arranged to align with the sample chambers 3280. To perform thermal cycling, the thermal block 3250 is brought into contact with the film layer 3220 of the substrate 3210 and force is applied to move the substrate 3210 and thermal block 3250 together, for example, via an optical detection mechanism acting on the side of substrate 3210 opposite to the side the thermal block 3250 is in contact with, as shown in FIG. 33. The protrusions 3260 may be configured such that the protrusions 3260 deform the film layer 3220 and partially enter the chamber 3280, such that the film layer 3220 contacts the inner periphery of the opening of the chamber 3280, sealing the chamber 3280 from the channels 3275 and 3276, as shown in FIG. 33. Thus, the protrusions 3260 on the thermal block 3250 permit direct isolation of the sample in the sample chambers 3280, rather than sealing portions of the channels 3275 and 3276.

Figure 34:
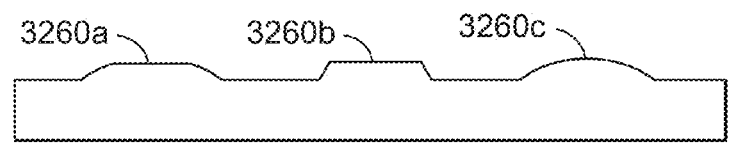
FIGS. 34, 35, and 35A are partial, cross-sectional views of thermal blocks for sealing a substrate according to various embodiments of the present teachings.

The sealing protrusions 3260 of the thermal block 3250 may have various configurations. In an exemplary embodiment, the dimensions of the protrusions 3260 should be such that sufficient contact is made to seal the chambers 3280 from the channels 3275 and 3276. By way of example, the sealing protrusions 3260 may have a substantially circular configuration with a radius that is slightly larger than the radius of the chambers 3280. The top of the sealing protrusions 3260 may be substantially flat, as shown by protrusions 3260a and 3260b in FIG. 34, or may be rounded, as shown by protrusion 3260c in FIG. 34. Likewise, the sides of the sealing protrusions 3260 may be rounded, as shown by protrusions 3260a and 3260c, or substantially flat, as shown by protrusion 3260b. In the case of a sealing protrusion having a flat top and rounded sides, like 3260a, a rounded protrusion may be formed with its top cut off so as to be flat. A rounded configuration may provide a slightly larger alignment tolerance with the sample chambers by permitting a sliding movement to be implemented during positioning the thermal block in contact with the substrate.

According to exemplary embodiments, the sealing protrusions 3260 may be machined directly on the thermal block 3250 or may be formed on a metal insert secured to the thermal block 3250.

Figure 35:
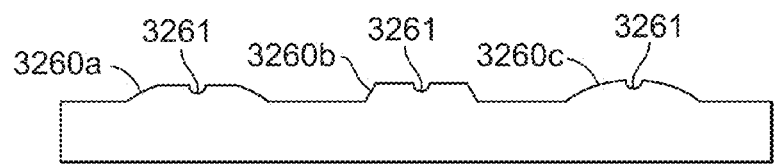
Figure 36:
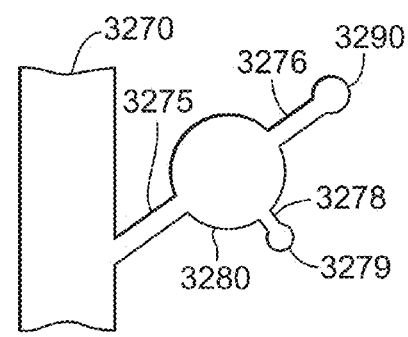
FIG. 36 is a top view of a sample chamber with an escape channel according to various embodiments of the present teachings.

Due to the sealing protrusions of a thermal block entering the sample chambers to perform sealing, as discussed above, it may be desirable to permit a relatively small amount of displaced sample contained in the chambers to escape. FIGS. 35 and 36 illustrate exemplary embodiments that permit the escape of a small amount of displaced sample from the sample chambers when the sealing protrusions of a thermal block enter the sample chambers to seal the chambers.

Figure 35A:
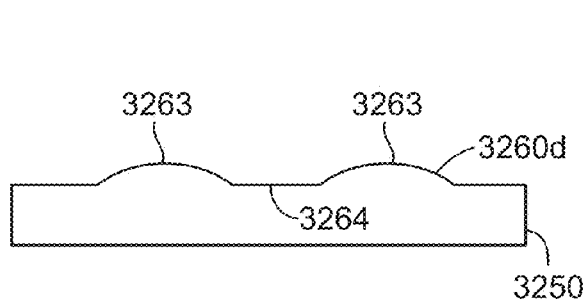

Referring first to FIG. 35, a small recess 3261 (e.g., dimple) may be formed in the sealing protrusions 3260 of the thermal block 3250 in order to fill with displaced fluid as a result of reduction of the sample chamber volume during sealing. In various exemplary embodiments, the recess 3261 may form a hole through the sealing protrusions 3260 from one side to another to permit a small amount of fluid displaced from the chamber to escape if needed so as to avoid the potential for over-pressurization of the chamber and potential adhesion failure of the film layer to the base during thermal cycling. FIG. 35A depicts another exemplary shape of a sealing protrusion 3260d on a thermal block 3250 for performing sealing and also permitting displaced sample in a sample chamber to escape. The sealing protrusion 3260d includes raised perimeter portions 3263 and a recessed center portion 3264. The raised perimeter portions 3263 may enter the sample chamber proximate the edge (periphery) of the sample chamber and seal the sample chamber. The recessed center portion 3264 may permit any displaced sample from the chamber to escape during sealing.

FIG. 36 represents another exemplary embodiment that may be used to protect against over-pressurization and/or adhesion failure when the thermal block sealing protrusions 3260 enter the chambers 3280. In FIG. 36, a side escape channel 3278 that is slightly deeper than the feed channels 3275 and 3276 may be provided in flow communication with each sample chamber 3280. A main fluid channel 3270 that is used to supply sample to the inlet feed channel 3275 also is depicted in the exemplary embodiment of FIG. 36. During filling, a small displaced amount of sample may escape through the escape channel 3278, and may also leave a small amount of air at the end of the escape channel 3278, which may end in a venting chamber 3279 similar to the venting chambers 3290 at the end of the vent (outlet) channel 3276, as are described herein. By forming the escape channel 3278 with a greater depth than the channels 3275 and 3276, when the sealing protrusions of the thermal block enter the chamber to seal off the channels 3275 and 3276, for example, as depicted in FIG. 33, the sealing protrusions 3260 may not fully seal the channel 3278 due to its greater depth. This may permit any displaced fluid in the chamber 3280 to pass into the escape channel 3278 during sealing and thermocycling, which in turn, may reduce the potential for over-pressurization in the chamber 3280 and adhesion failure (e.g., leakage) of the film layer 3220.

Although the embodiments of FIGS. 32-36 above described a thermal block having sealing protrusions (sealing protrusions 3260) that mate with sample chambers to perform sealing, it is envisioned that protrusions on a thermal block also may be configured and arranged to achieve a sealing pattern similar to that shown by the gaps 140 of FIG. 5. In other words, the thermal block and sealing protrusions thereon may contact and seal the substrate at locations of the sample introduction and venting channels in flow communication with each sample chamber. Those of ordinary skill in the art would understand how to configure and arrange sealing protrusions on a thermal block to accomplish this type of sealing.

Figure 38:
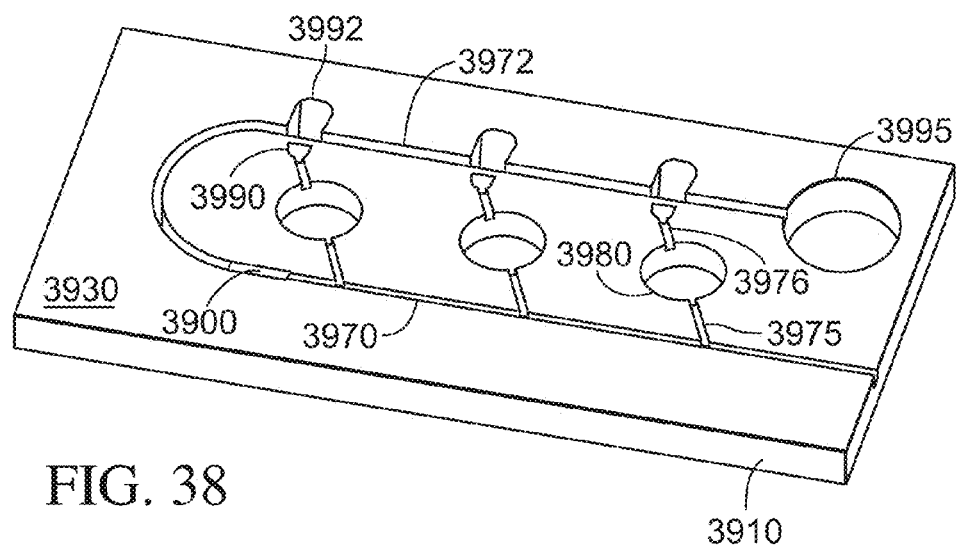
FIG. 38 is a perspective view of a substrate for biological analysis according to various embodiments of the present teachings.

FIGS. 38 and 39A-39C depict yet another exemplary approach for achieving sealing of sample chambers in a substrate for biological testing. Referring to FIG. 38, a schematic representation of a substrate 3910 is shown, showing only three sample chambers 3980 for ease of illustration. In accordance with the teachings herein, the substrate 3910 may comprise a base 3930 and a film layer covering the base to form the sample distribution network shown. In the exemplary embodiment, each sample chamber 3980 is in flow communication with a main fluid supply channel 3970 via a sample introduction (inlet) channel 3975. A venting channel 3976 leads from each sample chamber 3980 to a venting chamber 3990. A through hole (not shown) leads through the substrate 3910 from each venting chamber 3990 to a corresponding venting chamber 3992 provided in a main fluid outlet channel 3972 that connects to the main fluid supply channel 3970, for example, in a U-shaped bend as shown. The main fluid outlet channel 3972 terminates in an overfill chamber 3995. A dissolvable plug of material 3900 is positioned in the main fluid channel 3970 just downstream of the last introduction channel 3975 and corresponding chamber 3980 and upstream of the venting chamber 3992 corresponding to that chamber 3980. For example, the dissolvable plug 3900 may be positioned before the U-shaped junction of the main fluid supply channel 3970 and the main fluid outlet channel 3972. The plug 3900 may be made of a material that can fill the channel 3970 to block fluid flow temporarily as the material dissolves at a controlled rate. By way of example, the plug 3900 may be made of polyethylene glycol.

Figure 39A:
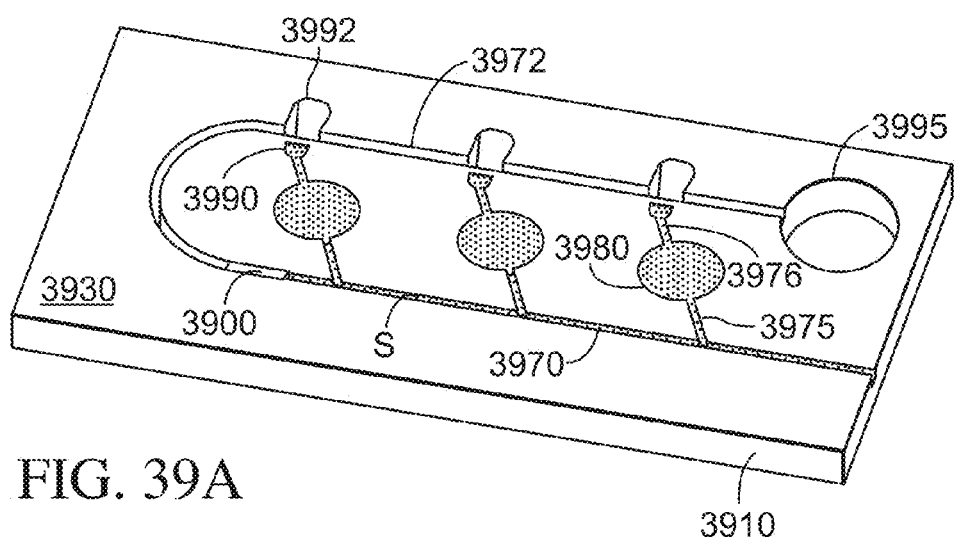
FIGS. 39A-39C are perspective views of steps of filling and sealing the substrate of FIG. 38 according to various embodiments of the present teachings.
Figure 39B:
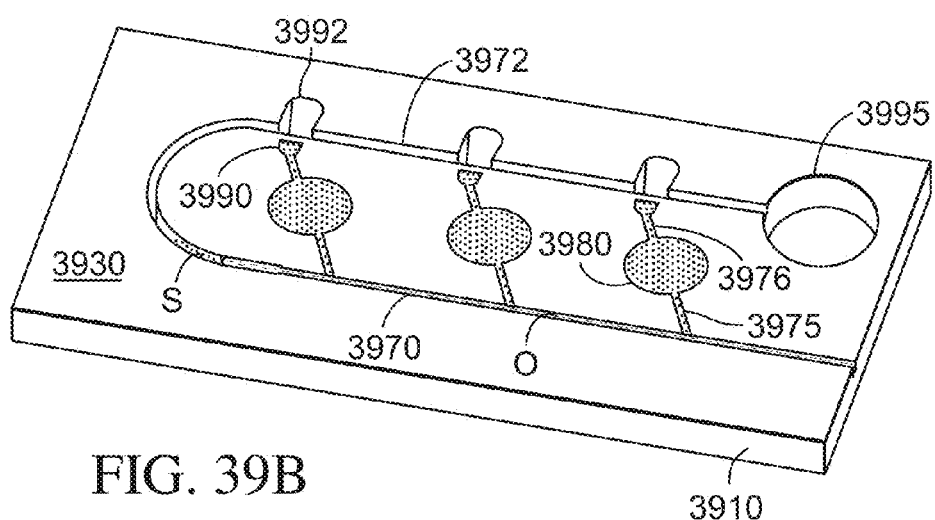
Figure 39C:
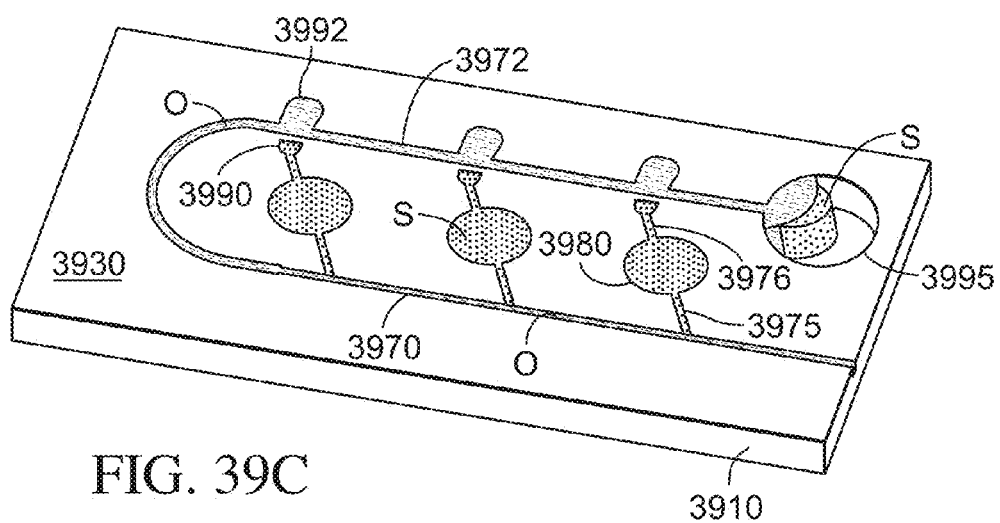

FIGS. 39A-39C illustrate various exemplary steps to fill and seal the substrate 3910. In FIG. 39A, sample S (e.g., a biological sample) is introduced to the substrate 3910. The sample S may be pumped through the main fluid supply channel 3970, the introduction channels 3975, and into the sample chambers 3980 via pressure from a volume of oil (not shown in FIG. 39A), or other substance that is immiscible with the sample, that is pumped behind the sample S. As shown in FIG. 39A, the sample S that is introduced is sufficient to fill the sample chambers 3980, the introduction and venting channels 3975 and 3976, the venting chambers 3990, and the main fluid supply channel 3970 from the inlet of the substrate 3910 (at the right hand side in FIG. 39A) up to the plug 3900. The plug 3900 prevents the sample S from advancing past the plug 3900 until the sample S has a chance to fill the various chambers and channels, as shown in FIG. 39A.

Once the substrate 3910 has been filled with sample S, as depicted in FIG. 39A, the plug 3900 may begin to dissolve, thus allowing any remaining supply of sample S to the substrate 3910 and the oil O behind it to flow in the main fluid supply channel 3970 past the location of the plug 3900, as shown in FIG. 39B. The oil O may continue to be supplied to the substrate 3910 such that it fills the main fluid supply channel 3970, the main fluid outlet channel 3972, the venting chambers 3992, and reaches the overfill chamber 3995, as shown in FIG. 39C. Due to the immiscibility of the oil O and sample S, once the oil fills the portions of the substrate 3910 described above and shown in FIG. 39C, the oil acts to seal the inlet and outlet of each of the sample chambers 3980, for example, so that further processing of the sample in the chambers 3980 may occur. The total volume of sample S and oil O that are supplied to the substrate 3910 may be selected so as not to fill the overfill chamber 3995 completely. According to various embodiments, the main outlet channel 3972 may have a volume that is larger than the main fluid supply channel 3970 since the channel 3972 fills with oil and does not affect the waste ratio of the sample, assuming the time required to pump the oil through the main fluid supply channel 3970 is not too great.

In an exemplary aspect, the pumping of the sample into the substrate 3910 may be at a substantially constant pressure so that the pressure is not excessive so as to burst the seals during the time between filling the last well and breaking through the plug 3900. To allow the sample S to reach the plug 3900, a vent hole (not shown) that permits gas (e.g., air) to escape the substrate 3910 may be provided. According to various embodiments, a mechanical sealing mechanism may be desired at the inlet and outlet of channels 3970 and 3972 to prevent oil from being pumped out due to potentially expanding sample S, for example, during PCR and/or thermocycling. In various embodiments, it also may be desirable to exert pressure on the oil to pressurize the fluids to reduce bubble formation. In an exemplary aspect, such force may be placed on the film layer covering the base.

According to various embodiments, the oil sealing approach described above may include variations. By way of example, and not limitation, instead of the dissolvable plug 3900, a burst valve or a Timavo valve can be used. In this case, rather than waiting for the plug to dissolve, the sample slug can be immediately followed with an oil slug. Also, rather than utilizing the vents described above, membranes (porous or gas permeable) can be used between the venting channel and the main fluid outlet channel. In yet another exemplary embodiment, in place of the vents described with reference to FIGS. 38 and 39A-39C, a hydrophobic stop can be used between the venting channel and the main fluid channel. Further, the configuration of the main channels may be more along the lines of FIG. 8A, where sample is introduced along one main channel, and venting occurs along the other main channel, without the two channels being connected in the U-shaped junction of the embodiment of FIGS. 38 and 39A-39C. The main venting channel could either terminate in a large overfill chamber or use a valve to a waste port. The sample can be followed directly with oil in the main fluid supply channel. After the sample has been filled, oil can be introduced into the main venting channel, either at the same time as the oil is introduced into the main fluid supply channel, or either one can precede the other. This configuration can be combined with any of the venting approaches in accordance with the teachings herein.

Figure 40A:
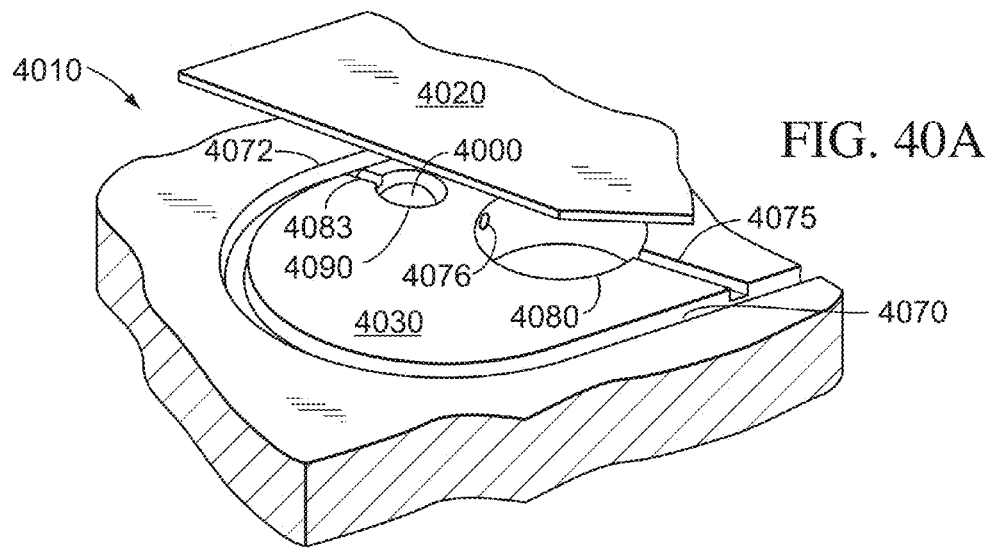
FIG. 40A is a partial, perspective, isometric view of a substrate for biological analysis according to various embodiments of the present teachings.
Figure 40B:
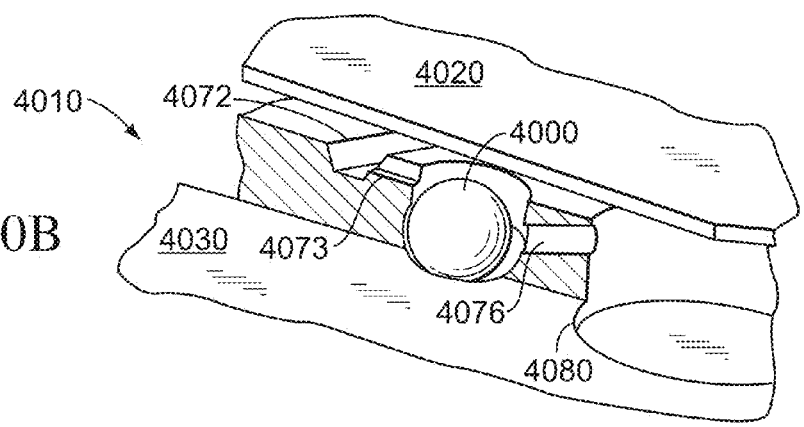
FIGS. 40B and 40C are partial cross-sectional views of the substrate of FIG. 40A showing the substrate before and after being filled with sample, respectively.
Figure 40C:
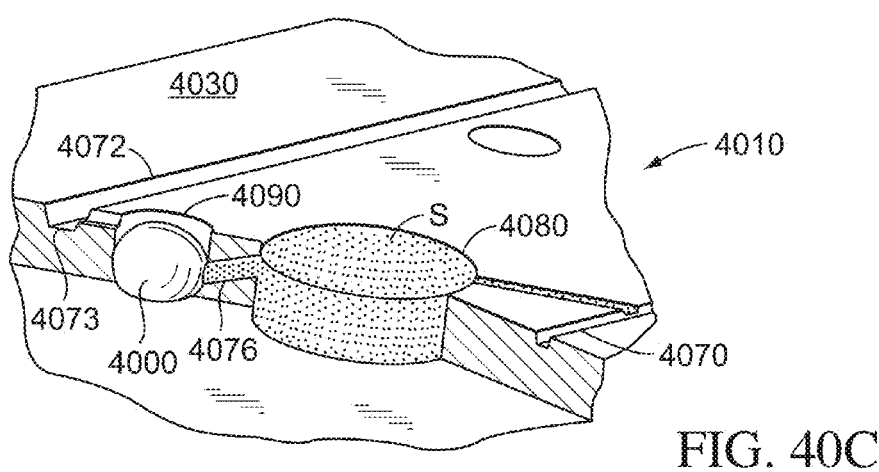

FIGS. 40A-40C depict yet another exemplary embodiment of an approach to seal sample chambers in a substrate. The embodiment of the substrate 4010 shown in the partial views of FIGS. 40A-40C is similar in design to the substrate 3910 of FIGS. 38 and 39A-39C with respect to the main fluid supply channel 4070, sample introduction channels 4075, sample chambers 4080, and main outlet channel 4072. In the embodiment of FIGS. 40A-40C, the sample chambers 4080 are in flow communication with venting chambers 4090 via venting channels 4076 that are tunneled through the base 4030, as shown best in FIGS. 40B and 40C. The venting chambers 4090 are in flow communication with the main fluid outlet channel 4072 via connection channels 4073, as shown in FIGS. 40A-40C, which may be formed at the upper surface of the base 4030, rather than through the base 4030 like channels 4076. For simplicity, FIGS. 40A-40C show only a partial view of the substrate 4010 depicting one sample chamber 4080. It should be understood, however, that an array of such sample chambers 4080 and corresponding introduction and venting channels and chambers are provided.

The exemplary embodiment of FIGS. 40A-40C includes a plug (e.g., bead) 4000 of super-absorbent material disposed in the venting chambers 4090. Such a super-absorbent material may be configured so as to absorb many times the bead's volume in water relatively rapidly and retain the water under relatively high pressure so that water is prevented from filtering through the bead and exiting therefrom. Examples of such super-absorbent materials that may be used to form the bead 4000 include, but are not limited to, polymers, such as, for example, cross-linked polyacrylate.

Prior to filling the substrate 4010 with sample, the bead 4000 may be positioned within the venting chamber 4090 such that it does not occupy the entire volume of the venting chamber 4090, as depicted in FIG. 40B. After sample S is introduced into the substrate 4010 and fills the chambers 4080, as depicted in FIG. 40C, the sample S exits through the venting channels 4076 and into the venting chambers 4090 in contact with the beads 4000, causing the beads 4000 to absorb the sample S and swell. The swelling of the beads 4000 in turn occupies the venting chambers 4090 and blocks the venting channels 4076, thereby sealing the chambers 4080 so that sample therein cannot escape and further processing, such as PCR, may be performed. In various embodiments, the sample introduction channels 4075 may be sealed via a fluid that is immiscible with the sample, such as, for example, oil, in a manner similar to that described with reference to FIGS. 38 and 39A-39C. Other sealing mechanisms in accordance with the present teachings also may be used to seal the sample introduction channels 4075 and would be understood by those skilled in the art based on the present teachings.

The beads 4000 may be configured so as not to block the connection channels 4073 when they have absorbed the sample S, thereby permitting escape of gas (e.g., air) into the main outlet (vent) channel 4072. In various embodiments, it may not be necessary to permit gas to escape the venting chambers and out of the substrate, however, since even at elevated temperatures, the super-absorbent beads 4000 may retain water without the tendency for the water to evaporate. This may be especially true when the beads are used for a relatively small fraction of their absorptive capacity.

In various embodiments, the beads 4000 may be substantially spherical and have a diameter of about 1 mm prior to absorbing sample. It is envisioned, however, that other shapes and sizes of the beads 4000 may be used. In particular, the shape and size of the beads 4000, as well as the configuration of the venting chamber 4090, may be selected such that the beads may swell and deform to substantially match the surface of the opening of the venting channel 4076 to the venting chamber 4090. Further, venting chamber 4090 may be small enough so that the bead 4000 may only expand to a limited extent to prevent the bead 4000 from absorbing more than a predetermined amount of sample. In the exemplary embodiment of FIGS. 40A-40C, the venting chamber 4090 may have a substantially egg-shaped configuration, narrowing toward the end where the venting channel 4076 enters the chamber 4090.

According to various other embodiments, the venting channel 4076 may be provided in the surface of the base 4030, as previously described herein, rather than having the cylindrical configuration shown in FIGS. 40A-40C. With such a configuration, it may be more difficult to ensure that the beads 4000 expand so as to conform to the relatively square profile defined by the film layer covering the base. However, it may be possible for the expansion of the beads 4000 to cause enough pressure on the film layer 4020 to create a rounded top surface. Further, the sealing may not need to be complete if a secondary sealing mechanism also is employed, such as, for example, the oil sealing described with reference to FIGS. 38 and 39A-39C.

In yet further exemplary embodiments, the bead 4000 may be in the form of a superporous hydrogel bead that acts to absorb sample and permit passage of gas.

Figure 41A:
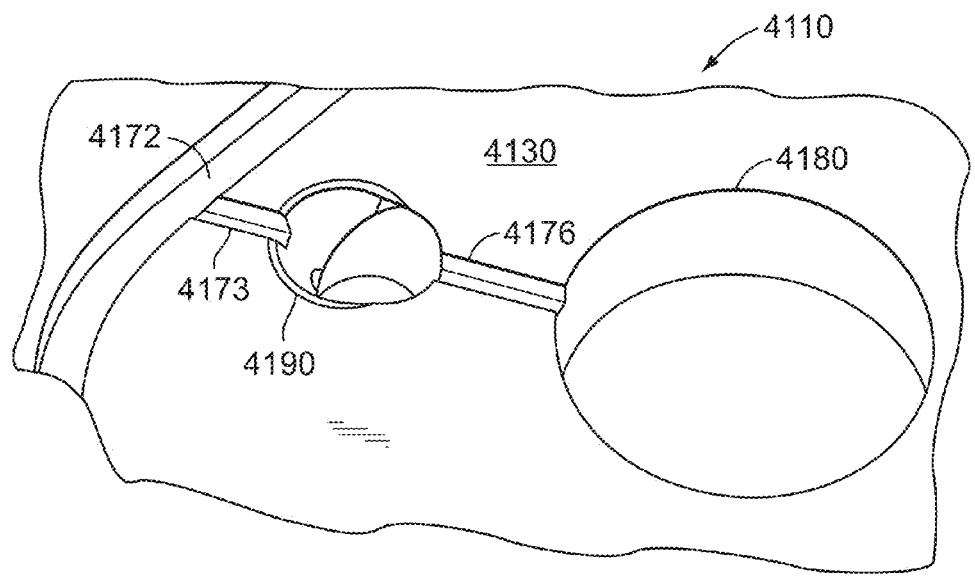
FIGS. 41A and 41B are partial perspective views of a substrate for biological analysis according to various embodiments of the present teachings.
Figure 41B:
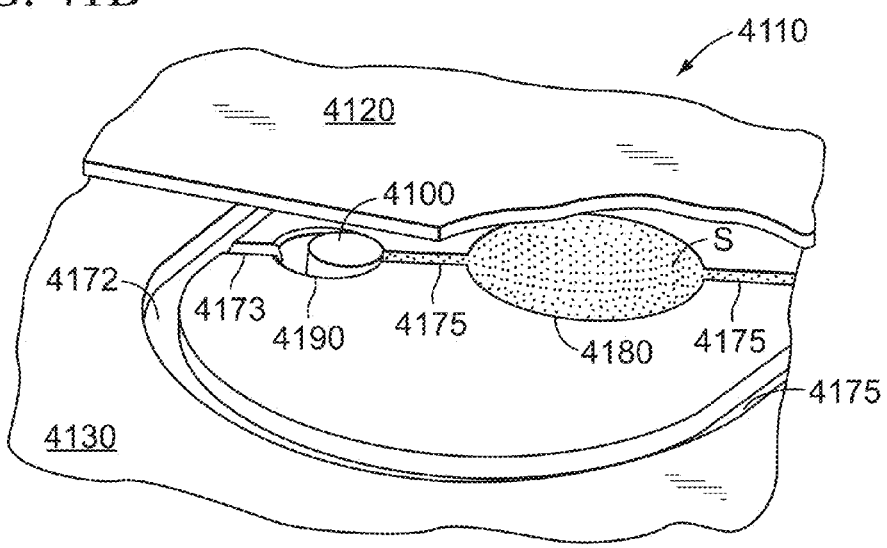

FIGS. 41A and 41B show an embodiment of a substrate 4110 that includes the use of a porous, hydrophobic pellet 4100 inserted into a venting chamber 4190 for both sealing the sample chambers 4180 and also permitting venting of gas from the substrate. Such a pellet 4100 may be relatively easy to manipulate and insert into the individual venting chambers 4190. Further, placing the pellets 4100 substantially in the same plane as the chambers 4180, as described below, may be advantageous during thermocycling, for example, to provide more efficient heat transfer and/or a more effective thermal contact between a thermal block and the substrate.

The substrate 4110 may have a configuration similar to that described in the embodiment of FIGS. 40A-40C, with the exception that the venting channel 4176 is not formed through the substrate 4110, though it may be if desired, but rather on the surface of the substrate 4110. In the embodiment of FIGS. 41A-41B, the venting chamber 4190 may have a substantially square edge at the side of the chamber 4190 proximate the venting channel 4176 and a tapered edge at the side proximate the connection channel 4173. A substantially cylindrical porous hydrophobic pellet 4100 may be inserted into the venting chamber 4190 into contact with the tapered side first and then pushed forward against the square side, as depicted in FIG. 41B. The top surface of the pellet 4100 may sit slightly above the surface of the base 4130, as shown in FIG. 41B, and may be pushed down so as to be substantially flush with the surface of the base 4130 when the film layer 4120 is adhered to the base 4130.

After filling the substrate 4110 with sample S, the pellet 4100 may prevent the sample from flowing past it, as shown in FIG. 41B, but could allow for the passage of air due to its porous nature. According to various embodiments, the pellets 4100 for each venting chamber 4190 may be formed from a coil of material, similar to a coil of string, and cut into small pieces and placed in a consistent orientation so as to be properly positioned in each venting chamber 4190.

In various embodiments, the sample introduction channels 4175 leading to the sample chambers 4180 may be sealed via a fluid that is immiscible with the sample, such as, for example, oil, in a manner similar to that described with reference to FIGS. 38 and 39A-39C. Other sealing mechanisms in accordance with the present teachings also may be used to seal the sample introduction channels 4175 and would be understood by those skilled in the art based on the present teachings.

Figure 42A:
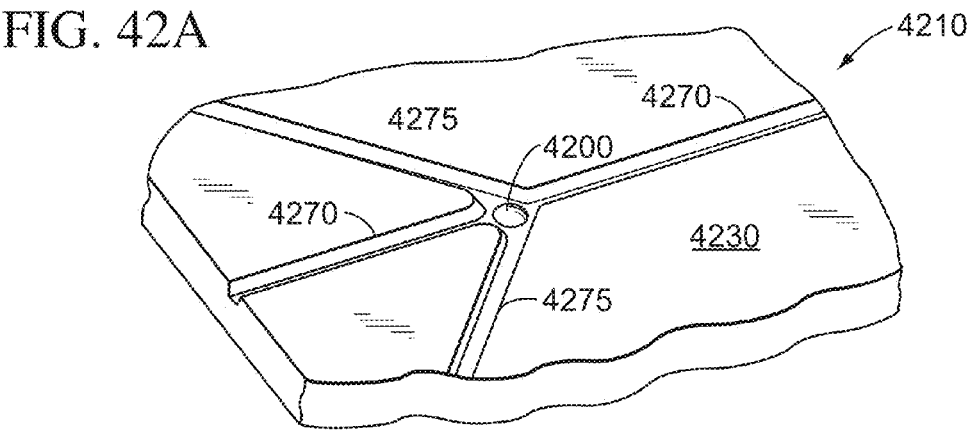
FIGS. 42A-42C are partial perspective views of a substrate for biological analysis according to various embodiments of the present teachings.
Figure 42B:
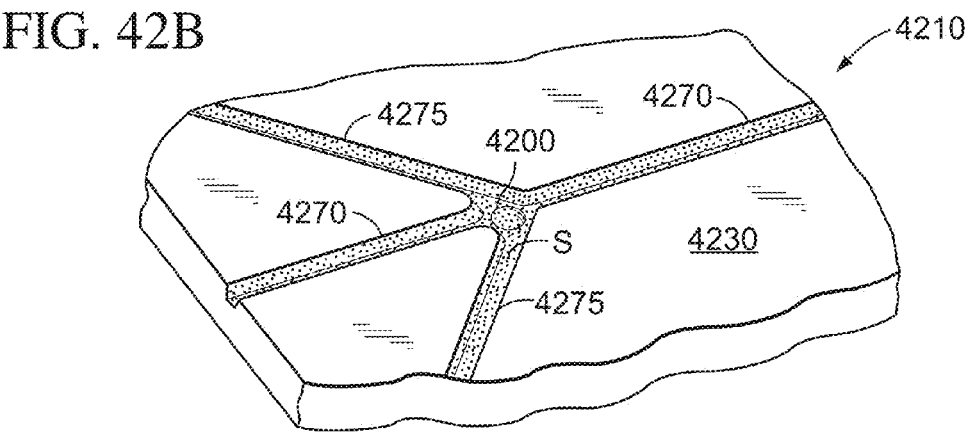

According to still further embodiments, a material capable of breaking down to a gas, for example, with elevated temperatures may be used to seal sample chambers of a substrate. With reference to FIG. 42A, a partial perspective view of a substrate 4210 is depicted. The view in FIG. 42A shows a main fluid supply channel 4270 that is in flow communication with two sample introduction channels 4275 that lead to sample chambers (not shown). A material 4200 that is configured to break down into a gas at elevated temperatures is placed at the junction between the main fluid supply channel 4270 and the introduction channels 4275. According to various exemplary embodiments, the material 4200 may be predeposited in the substrate 4210. The material 4200 may be or may be made insoluble in water so it does not dissolve upon contact with the sample S as the sample S fills the substrate 4210, as depicted in FIG. 42B. For example, the material may be deposited with an organic solvent.

Figure 42C:
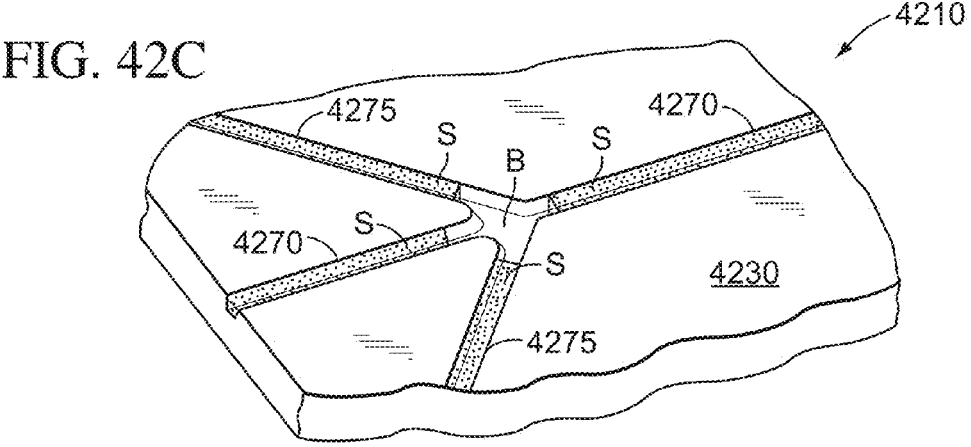

The material 4200 may break down into a gas, like a blowing agent, at elevated temperatures, for example, at temperatures associated with PCR and/or thermocycling. By way of example, the material 4200 may turn to gas at temperatures of about 90° C. Thus, as shown in FIG. 42C, the material 4200 may turn into a gas, for example, after the substrate 4210 has been heated in the first step of a PCR process. This creates a bubble B at the junction that prevents the sample S from migrating from one sample chamber to another, thereby sealing the sample chambers. Although FIGS. 42A-42C depict the use of the material 4200 at the junction between a main fluid supply channel 4270 and introduction channels 4275, it should be understood that this approach also may be used to seal the sample chambers at their outlet (e.g., vent) sides. In various embodiments, the interior channel surfaces may be relatively hydrophobic in order to prevent sample from wicking around the bubble B.

Figure 43A:
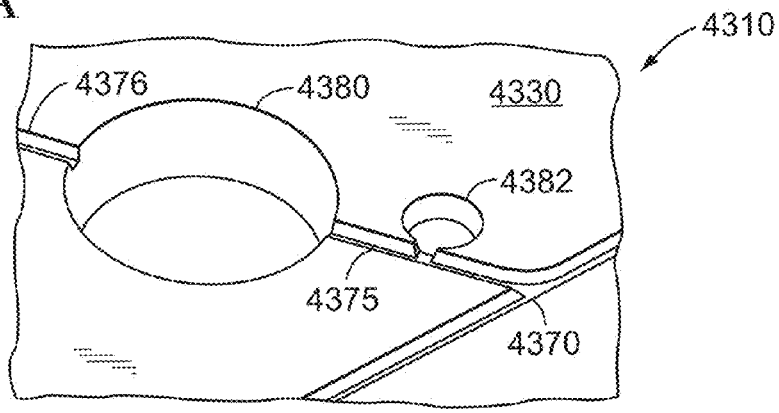
FIGS. 43A-43C are partial perspective views of a substrate for biological analysis according to various embodiments of the present teachings.
Figure 43B:
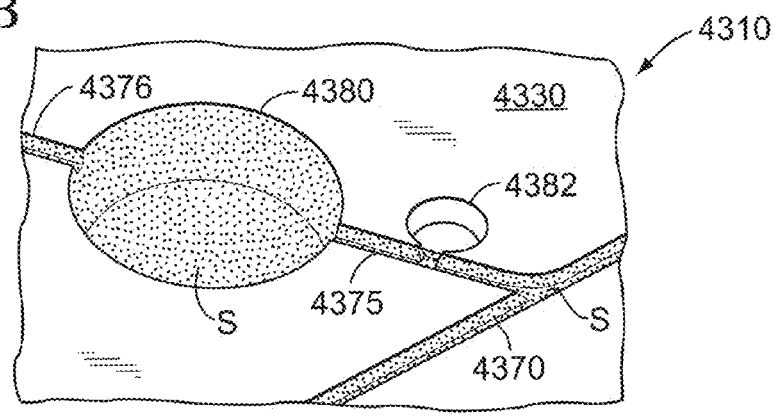
Figure 43C:
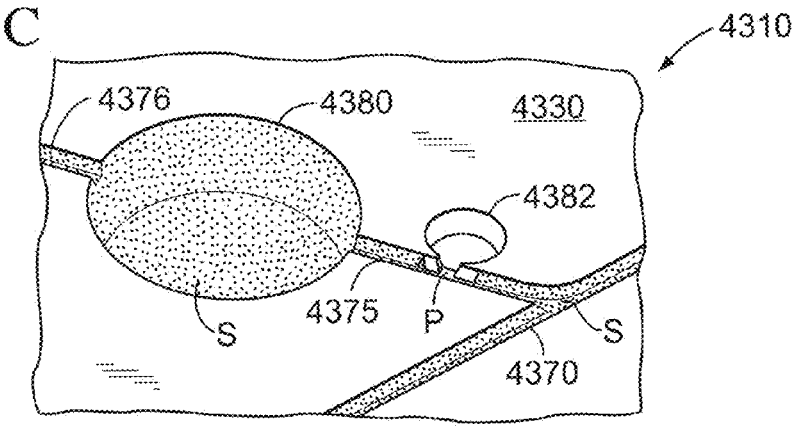

FIGS. 43A-43C depict yet another exemplary approach for sealing the sample chambers of a substrate for biological testing in accordance with the present teachings. Again, for ease of discussion, only one sample chamber 4380 of the substrate 4310 is depicted in FIGS. 43A-43C. With reference to FIG. 43A, the substrate 4310 includes a small blind chamber 4382 in flow communication with the sample introduction channel 4375 upstream of the sample chamber 4380 between the sample chamber 4380 and a main fluid supply channel 4370. Assuming that pressure filling is used to supply sample to the substrate, the sample S progresses through the main fluid supply channel 4370, into the introduction channel 4375 and sample chamber 4380, and into the venting channel 4376, without substantially filling the blind chamber 4382, as shown in FIG. 43B. This is due to the pressure resistance of the relatively small blind chamber 4382 in comparison to that of the chambers 4380. Thus, the blind chamber 4382 contains trapped air after the remainder of the substrate has been filled.

Upon further processing of the sample in the sample chambers, for example, during thermocycling and/or PCR, elevating the temperature of the substrate 4310 causes the trapped air in the chamber 4382 to expand, introducing an air pocket P in the portion of the introduction channel 4375 slightly upstream and downstream of the chamber 4382, as shown in FIG. 43C. The air pocket P serves to seal the chamber 4380. Skilled artisans would understand that a blind chamber, similar to 4382, also may be provided on an outlet side of the sample chamber 4280 in conjunction with the venting channel 4376 to perform sealing.

Although FIGS. 43A-43C show the blind chamber 4382 being completely filled with trapped air, it should be understood that a small amount of sample S may enter the blind chamber 4382 during filling. However, as the substrate 4310 is heated during biological testing (e.g., PCR and/or thermocycling), the trapped air in the chamber 4382 will expands, forcing out any sample in the chamber 4382.

The embodiment of FIGS. 2A and 2B provides an exemplary configuration for achieving venting of gas via membranes from a substrate of a biological testing device, while substantially preventing leakage of the sample and/or other fluids that fill the substrate. Various additional exemplary embodiments for achieving venting in accordance with the disclosure are described below.

Figure 13:
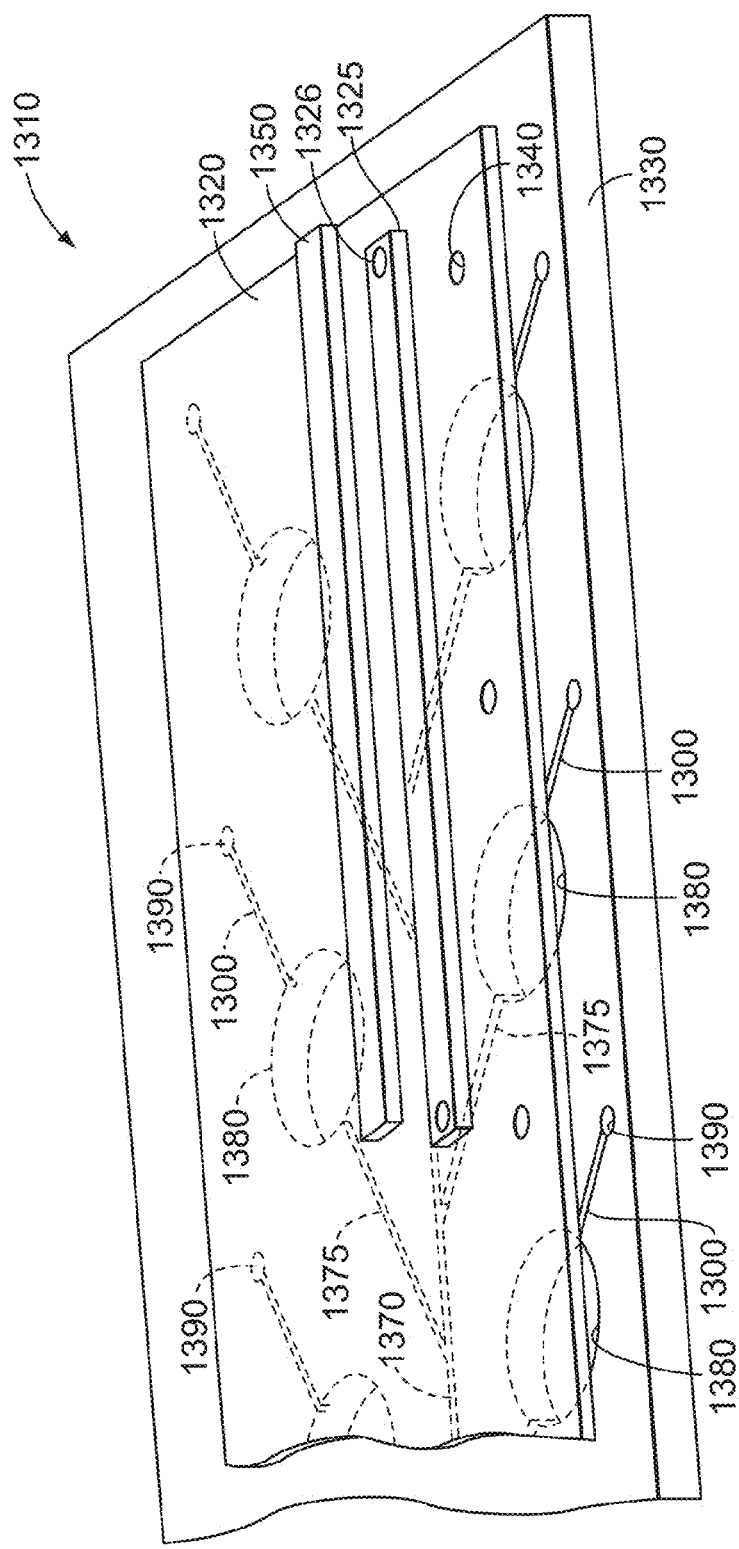
FIG. 13 is a perspective view of a substrate for biological analysis according to various embodiments of the present teachings.

With reference to FIG. 13, a partial perspective isometric view of an exemplary embodiment of a substrate 1310 including an array of features providing parallel processing of several samples for carrying out biological testing is illustrated. The substrate 1310 includes a base 1330 and a film layer 1320. Sample chambers 1380 may form a regularly spaced array, as depicted, for example, in FIG. 1. Sample introduced to the substrate (e.g., via sample ports like sample ports 60 in the embodiment of FIG. 1 and not shown in FIG. 13) flows to main channel 1370 and from there to sample introduction channels 1375 into sample chambers 1380. Each sample chamber 1380 is connected to a venting channel 1300 which joins a venting chamber 1390 with the sample chamber 1380.

The base 1330 and film layer 1320 may be made from any of the materials described herein for the bases and film layers, respectively. By way of example, the film layer 1320 may be a COP film or a PSA film and may be thermally bonded to the base 1330, which may be manufactured from a plastic material, for example, such as COP. As described above with reference to the embodiment of FIGS. 2A and 2B, the film layer 1320 may be provided with a plurality of vent holes 1340 configured to be aligned with the venting chambers 1390 when the film layer 1320 is attached to the base 1330. Rather than providing a die-cut membrane in each of the venting chambers 1390 like in the embodiment of FIGS. 2A and 2B, however, in the exemplary embodiment of FIG. 13, a venting membrane strip 1350 is provided on a side of the film layer 1320 that faces away from the base 1330 (e.g., on the top surface of the film layer 1320). Providing such a strip configuration may facilitate manufacturing of the device, for example, by permitting a single strip to serve as the vent membrane for a plurality of chambers 1390 and/or permitting relatively simple manufacturing of the strip 1350 and manipulation of the strip 1350 into position due to its relatively large size. The strip 1350 may be attached to the film layer 1320 via adhesive and may be aligned with a row of venting chambers 1390, as depicted in FIG. 13. Thus, a plurality of membrane strips 1350 may be positioned on the top surface of the film layer 1320 so as to align with a plurality of rows of venting chambers 1390 of the substrate 1310.

As shown in FIG. 13, according to various exemplary embodiments, the adhesive used to bond the membrane strip 1350 to the film layer 1320 may also be in the form of a strip 1325, for example, a PSA strip, provided on a bottom side of the membrane strip 1350 and having a length and width substantially similar to the membrane strip 1350. Vent holes 1326 may be provided through the adhesive strip 1325 and in alignment with the vent holes 1340 of the film layer 1320 and the venting chambers 1390. The vent holes 1326 and the vent holes 1340 may be formed via a laser, mechanically punching, or other suitable technique for forming vent holes. If PSA strips 1325 are used to bond the membrane strips 1350 to the film layer 1320, the film layer may be, for example, a COP film layer thermally bonded to the base 1330.

The membrane strips 1350 may be gas-permeable or porous and also liquid impermeable so as to prevent leakages of the sample fluid from the substrate 1310. In various exemplary embodiments, the membrane strips may be made of materials such as those described above for the membranes 40 of the embodiment of FIGS. 2A and 2B.

In various exemplary embodiments (not shown in the figures), instead of providing adhesive strips 1325 to bond the membrane strips 1350 to the film layer 1320, the film layer 1320 may be a double-sided adhesive PSA layer such that adhesive on one side of the layer 1320 is used to bond the film 1320 to the base 1330 and adhesive on the opposite side is used to bond the membrane strips 1350 to the film layer 1320. In such an embodiment, the vent holes 1340 would be formed through the entire film layer 1320 including both adhesive sides of the layer 1320.

According to various exemplary embodiments, when using multi-chamber devices for parallel processing of plural fluid samples, it may be desirable to cycle the device through various temperatures. For example, it may be desirable to perform PCR, which requires thermal cycling of the device over a range of temperatures, for example from about 60° C. to about 95° C. In such cases, relatively precise temperature control in the individual sample chambers of a substrate, as well as temperature uniformity over the entire substrate area may be desired. Further, as discussed above, the ability to isolate the individual chambers after filling the chambers (e.g., to prevent flow communication between the chambers and between the chambers and channels that lead to and from each chamber, such as fluid introduction and venting channels), may be desired in order to prevent cross-contamination during a biological testing process such as PCR.

In order to perform thermal cycling, in accordance with various exemplary embodiments, a thermal block may be placed in contact with the multi-chambered substrate. Typically, the thermal block is placed in contact with the film layer of the substrate that, together with the cavities formed in the base of the substrate form the fluid distribution network made up of, for example, main fluid channels, a plurality of sample chambers (e.g., in an array) in flow communication with the main fluid channel by a plurality of sample introduction channels, and a plurality of venting chambers in flow communication with the plurality of sample chambers via a plurality of venting channels. In other words, the thermal block may be positioned in contact with the substrate on the side of the base of the substrate that defines the various channel and chamber openings. For example, in the exemplary embodiments of FIGS. 1, 2, and 13 the thermal block may be positioned in contact with the film layer 20 and with the membranes 1350 and film layer 1320.

Placing the thermal block on the same side of the base of the substrate that the membranes are located, however, may impair the ability to achieve effective and uniform thermal conductivity between the thermal block and the sample chambers. In particular, the presence of membranes, whether disposed between the film layer and the base or on the side of the film layer facing away from the base, may cause an irregular surface (e.g., a "bumpy" surface). Such an irregular surface may prevent uniform contact of the thermal block with the substrate, and in some cases, it may be desirable to remove the membranes and add a metal lamination layer instead of the film layer to perform PCR after the substrate has been loaded with sample.

Further membranes in the form of strips of material may have a potential to leak around the borders of the strips.

Figure 14:
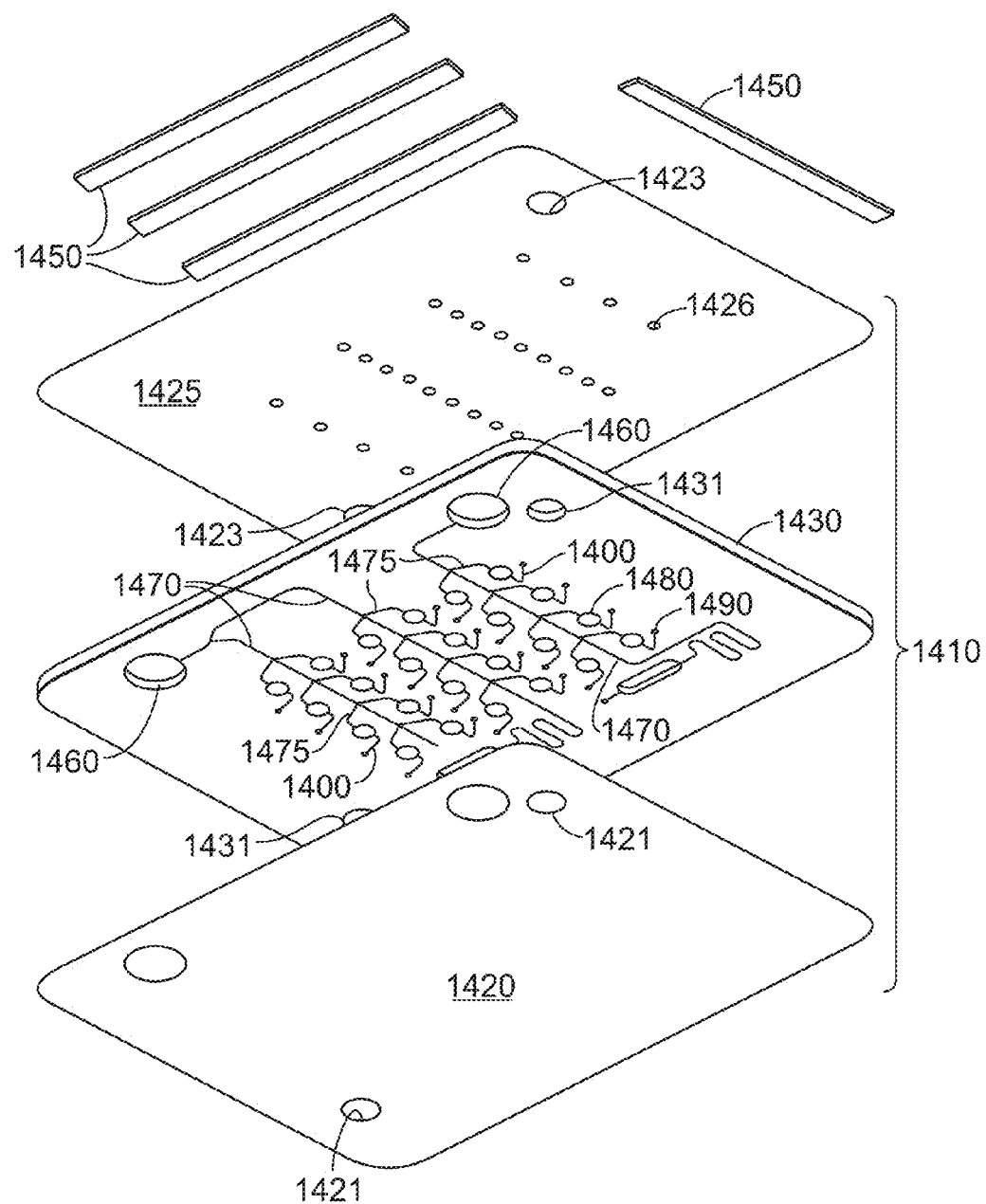
FIG. 14 is a perspective, isometric view of another substrate for biological analysis according to various embodiments of the present teachings.
Figure 15:
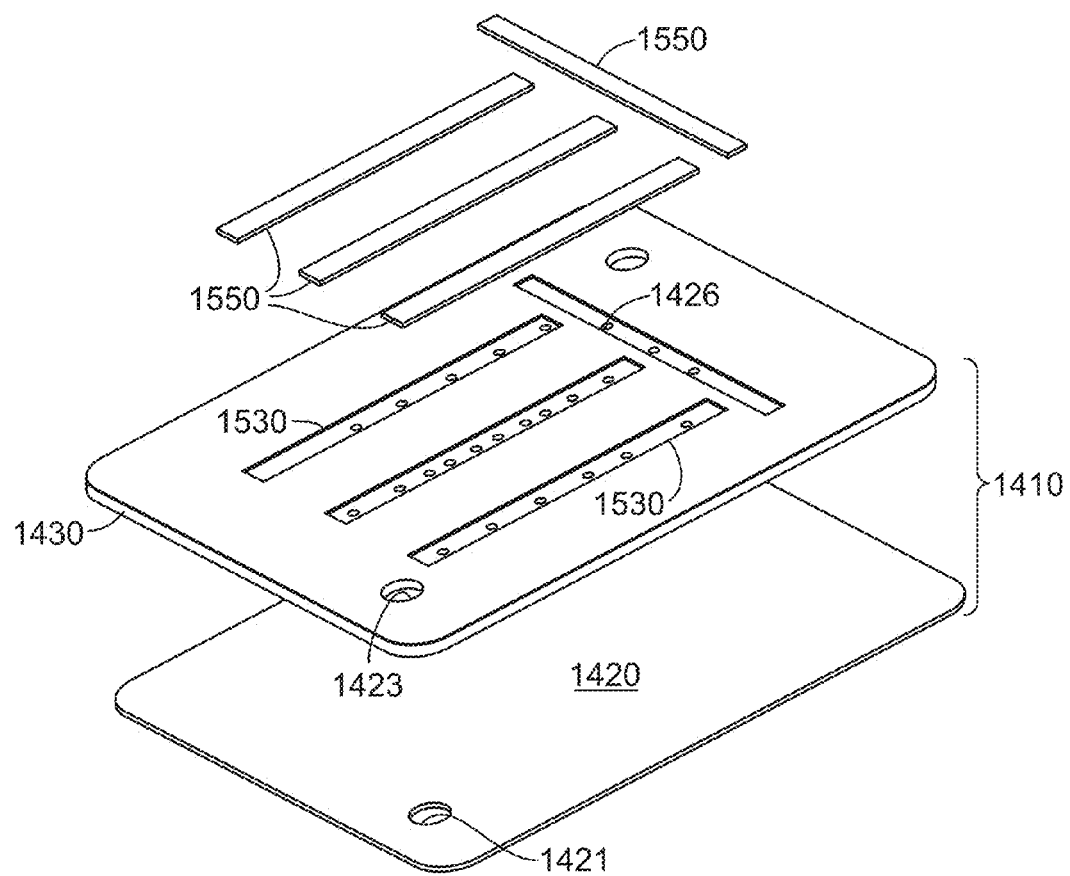
FIG. 15 is a perspective, isometric view of yet another substrate for biological analysis according to various embodiments of the present teachings.
Figure 16:
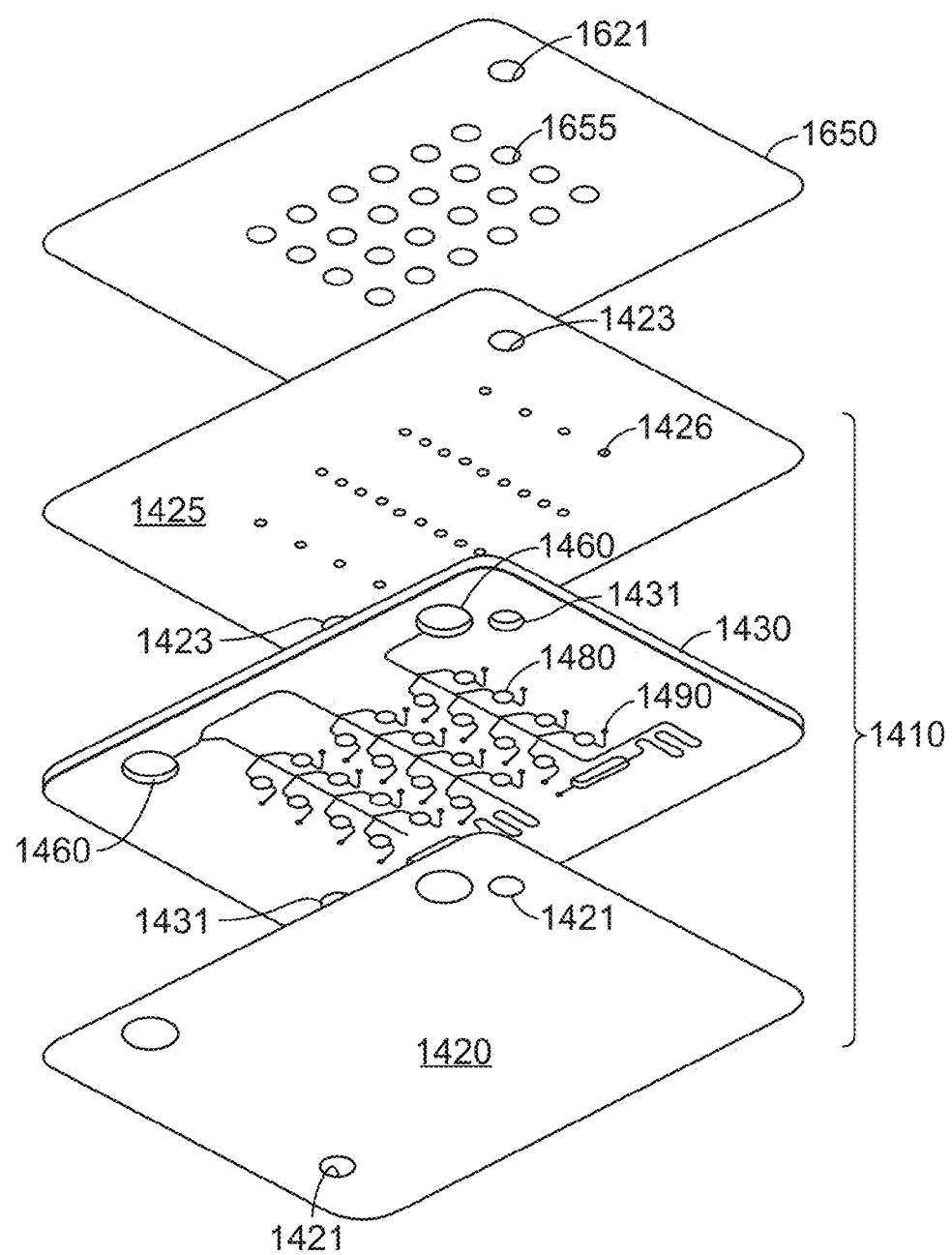
FIG. 16 is a perspective, isometric view of a substrate for biological analysis according to various embodiments of the present teachings.

With reference to FIGS. 14-16, various exemplary embodiments are schematically illustrated that provide gas-permeable or porous membranes for venting a substrate on a side of the substrate opposite to the side that is placed in contact with a thermal block for performing thermal cycling of the sample loaded into the substrate. FIG. 14 is an isometric perspective view of an exemplary embodiment of a substrate 1410 for which membrane strips 1450 are positioned on a side of the substrate 1410 (the side facing up in FIG. 14) that is opposite to the side (the side facing down in FIG. 14) of the substrate 1410 that the thermal block is placed in contact with during thermal cycling.

In the embodiment of FIG. 14, the substrate 1410 may comprise a base 1430 covered with a film layer 1420 that together define a fluid distribution network. FIG. 14 shows the side of the base 1430 looking through the film layer 1420. As shown in FIG. 14, the base 1430 and film layer 1420 may together define a plurality of sample chambers 1480 that form a regularly spaced array. Sample may be introduced in sample ports 1460 and may flow to main fluid supply channels 1470 and from there to sample introduction channels 1475 into sample chambers 1480. Each sample chamber 1480 may be connected to a venting channel 1400 that joins a venting chamber 1490 with the sample chamber 1480. A venting through hole (not shown) may be formed from each venting chamber 1490 and through the base 1430 so as to open at the side of the base 1430 facing upward in FIG. 14. Elements 1421, 1423 and 1431 are indexing holes provided in each layer of the substrate 1410 to provide appropriate alignment of the substrate 1410 with other instrumentation, if needed, for example, during filling and/or sample analysis.

Figure 28:
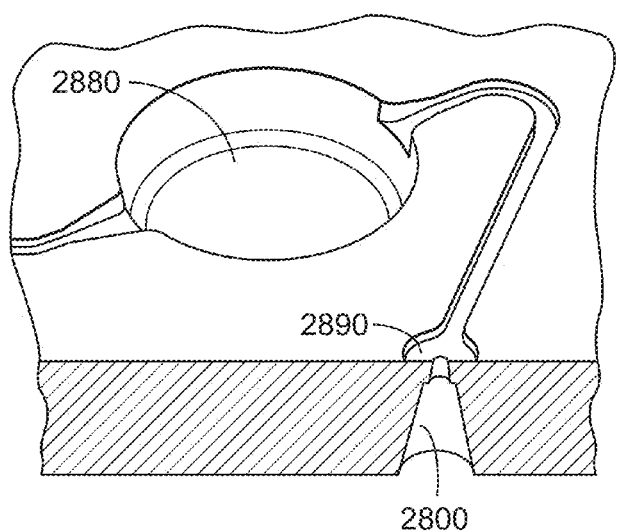
FIG. 28 is a partial cross-sectional view of a sample chamber and venting chamber provided with a vent through hole according to various embodiments of the present teachings.

FIG. 28 shows an exemplary venting through hole 2800 that may be used in conjunction with a venting chamber 2890 associated with a sample chamber 2880. The venting through hole 2800 in FIG. 28 may be used in the base 1430 of FIGS. 14-16. As shown in the exemplary embodiment of FIG. 28, the through hole 2800 may have a conical shape with a smaller opening leading from the venting chamber 2890 and a larger opening formed at the underside of the base. By way of example only, the opening leading from the venting chamber 2890 may be about 100 µm in diameter and the opening at the underside of the base may be about 500 µm in diameter. The conical configuration shown in FIG. 28 is exemplary only, and venting through holes in accordance with the teachings herein may have a variety of configurations, including, for example, cylindrical. The shape and size of the vent through holes may be selected based on various factors, including, for example, the manufacturing technique used to form the base, desired venting, and other such factors.

With reference again to FIG. 14, the film layer 1420 and the base 1430 may be made of any of the materials described herein for film layers and bases. In various embodiments, the film layer 1420 may be a metal or polymer PSA film and may be bonded to the base 1430 via the adhesive, for example, by applying pressure and/or heat. Further, the base 1430 may be etched, stamped, hot-embossed, or injection molded to form the various chambers and channels. Using a metal PSA film for film layer 1420 may be desirable to achieve good thermal conductivity.

As shown in FIG. 14, the substrate 1410 may further include, on the side of the base 1430 opposite to the side on which the film layer 1420 is placed, a film layer 1425 formed with a plurality of vent holes 1426. The vent holes 1426 may be configured and arranged so as to be substantially aligned with the vent through holes of the base 1430 described above. The film layer 1425 may be made of any of the materials described herein as useful for forming a film layer. By way of example, the film layer 1425 may be a PSA film layer and may be configured to be adhesively bonded and aligned with the base 1430. In accordance with various exemplary embodiments, the vent holes 1426 may be formed in the film layer 1425 via laser or via mechanical punching. In an alternative embodiment, the film layer 1425 may formed of a porous hydrophobic material and the vent holes 1426 may be eliminated.

Gas-permeable or porous membrane strips 1450 may be placed in contact with the film layer 1425 and in alignment with the vent holes 1426. Each membrane strip 1450 may be arranged and configured so as to cover a row of vent holes 1426. Examples of porous membranes include Gortex® and other similar materials known in the art and examples of selectively permeable membrane materials include, for example, PDMS. The membrane strips 1450 can be liquid impermeable so as to prevent leakage of sample from the substrate and to prevent a sponging effect of the liquid that can reduce the volume in the sample chamber. Other suitable porous membrane materials are described in U.S. Pat. No. 5,589,350 and other suitable gas-permeable membrane materials are described in U.S. Pat. Pub. No. 2005/0164373 entitled "Diffusion-Aided Loading System for Microfluidic Devices," both of which are incorporated herein.

According to various embodiments, the film layer 1425 may be a double-sided adhesive film layer, for example, a double-sided PSA polymer film, and the membrane strips 1450 may be adhered to the film layer 1425 via the adhesive provided on the side of the film layer 1425 facing the strips 1450. In alternative exemplary embodiments (not shown)

the film layer 1425 may be a PSA film having only one adhesive layer facing the base 1430. The membrane strips 1450 may be adhered to the opposite side of the film layer 1425 via adhesive strips (e.g., PSA strips) having substantially the same length and width as the membrane strips 1450. Thus, for example, the membrane strips 1450 may be adhered to the film layer 1425 via adhesive strips similar to adhesive strips 1325 shown and described with reference to the embodiment of FIG. 13. Like the adhesive strips 1325 of FIG. 13, adhesive strips used to adhere the membrane strips 1450 to the film layer 1425 may be provided with vent holes that align with the vent holes 1426 of the film layer 1425 and with the vent through holes (not shown) provided in the base 1430. When using PDMS membrane strips, additional adhesive may not be needed as PDMS is self-adhering.

With reference now to FIG. 15, another exemplary embodiment of a substrate having membranes for venting positioned on a side of the substrate opposite to the side of the sample chamber and channel openings in the base is shown. The exemplary embodiment of FIG. 15 includes components and materials similar to those described above with reference to the exemplary embodiment of FIG. 14, with the reference labels of such components being the same as those used in FIG. 14. In addition, in the exemplary embodiment of FIG. 15, recesses 1530 are formed in the base 1430. The recesses 1530 have substantially the same dimensions as the membrane strips 1550 and are configured to receive the membrane strips 1550 and a film layer attached to the membrane strips 1550 for bonding the membrane strips 1550 to the base 1430. The recesses 1530 may facilitate proper alignment of the membrane strips 1550 relative to the vent holes 1426 and vent through holes (not shown) of the base 1430 during placement of the strips 1550 on the substrate 1410. Also, providing recesses 1530 having a depth substantially equal to the thickness of the membrane strips 1550 may permit the membrane strips 1550 to be positioned flush with the upper surface of the substrate 1410. As such, a thermal block may be positioned in contact with the upper surface (e.g., the membrane side of the substrate 1410) and may make substantially uniform thermal contact with the upper surface, thereby enhancing uniform thermal conductivity. It should be understood, however, that a thermal block also may be positioned in addition or instead in contact with the bottom surface of the substrate 1410 (e.g., in contact with the film layer 1420), as described with reference to the embodiment of FIG. 14.

As described above with reference to the exemplary embodiment of FIG. 14, in various embodiments, the membranes 1550 of FIG. 15 may be bonded to the surface of a single sided adhesive layer 1425 via adhesive strips (not shown), for example, PSA adhesive strips, having substantially the same length and width as the membranes 1550. Again, however, if self-adhering PDMS strips are used, additional adhesive is not needed. Regardless of how the membrane strips 1550 are attached within the recesses 1530, the depth of the recesses 1530 may be selected so as to accommodate both the thickness of the membrane strips 1550 and the thickness of an adhesive layer such that membrane strips 1550 are substantially flush with the top surface of the substrate 1410. In other words, the top surface of the substrate 1410 and the membrane strips 1550 placed in position in the recesses should be substantially flat and uniform.

Yet another exemplary embodiment of a substrate for parallel processing of biological samples that utilizes a venting membrane on the backside of the substrate is shown in FIG. 16. The exemplary embodiment of FIG. 16 includes many of the same components and materials as described above with reference to the exemplary embodiment of FIG. 14, and illustrated components that are the same as those in the exemplary embodiment of FIG. 14 are indicated by the same reference labels. The exemplary embodiment of FIG. 16 differs from that of FIG. 14, however, in that the membrane strips 1450 are replaced with a single venting membrane layer 1650 configured and arranged to cover substantially the entire top surface of the substrate 1410, as depicted in FIG. 16.

Providing a single membrane 1650 may facilitate positioning and attaching of the membrane 1650 to the substrate 1410, may reduce the number of components, and thus also may facilitate manufacturing. The membrane 1650 also may include a plurality of optical apertures 1655 configured and arranged to be substantially aligned such that the sample chambers 1480 (shown in FIG. 14) can be optically detected during biological testing. It should be noted that optical detection of the chambers 1480 can occur through the optical apertures 1655 by providing a transparent film layer 1425 and transparent base 1430. The optical apertures 1655 may be substantially circular, although apertures also may have shapes other than circular.

According to various embodiments, in a manner similar to that described with reference to FIG. 15, the base 1430 of FIG. 16 may be provided with a single large recessed region (not shown in the view of FIG. 16) configured to receive the film layer 1425 and membrane 1650. This may permit the membrane 1650 to lie flush with the upper surface of the base 1430.

By providing the venting membranes 1450, 1550, and 1650 on the side of the substrate 1410 opposite to the side that is placed in contact with the thermal block during thermal cycling, as shown in the exemplary embodiments of FIGS. 14-16, it may be possible to achieve a more uniform and effective thermal conduction between the thermal block and the substrate 1410. Moreover, isolation of the sample chambers may be facilitated. For example, if staking and/or filling channels with adhesive is used to effect isolation of the sample chambers (e.g., blocking flow communication between sample chambers and between sample chambers and channels), such techniques may be performed at the side of the substrate opposite to the side on which the membranes are placed. Thus, a lower force may be applied to deform and/or puncture the film layer 1420 than would be required to deform and/or puncture both a film layer and membranes. Alternatively, sealing could occur on the same side as the venting membranes, especially in the embodiment of FIG. 16 if pressure is applied at the apertures 1655. The various membrane embodiments of FIGS. 14-16 also may facilitate sealing of the sample chambers of the substrate via the thermal block itself, for example, as shown and described with reference to the exemplary embodiments of FIGS. 32-36. The various membrane embodiments of FIGS. 14-16 also may facilitate manufacturing of the device as the membranes are relatively easily manipulated and installed. Moreover, the thermal conductivity may be improved by using a metal film layer 1420 and reducing thickness of that layer, which may be placed in contact with the thermal block during thermocycling. In some embodiments, where it may be desirable to heat the substrate from both sides (e.g., place a thermal block in contact with the membrane side and opposite side of the substrate), optical detection may occur via illumination from the edges of the substrate, though chambers may be restricted to locations around the perimeter of the substrate.

According to various embodiments, a heated cover used for processing (e.g., a thermal block in a thermocycler), if placed in contact with the venting side of the substrate in FIGS. 14-16, for example, may also include holes or porous areas that align with the vent holes and venting chambers to permit gas to escape during loading of the substrate while in place in a thermocycler.

In some circumstances, it may be desirable to eliminate venting membranes at each of the venting chambers. For example, by eliminating the need for such membranes, manufacturing may be facilitated and less costly since handling and assembly of the membranes is not needed. Further, precise alignment of the membranes will not be required and the chances of misalignment of a membrane and potential consequent leakage of sample may be avoided. Also, isolation (e.g., sealing) of the sample chambers of the substrate may be facilitated and improved due to a reduction in force needed to deform and/or penetrate substrate layers to achieve isolation, as removal of the membranes may provide less layers to deform and/or penetrate. Finally, removal of such venting membranes may improve thermal conductivity and thermal uniformity, for example, during PCR thermal cycling, due to the provision of a substantially flat surface with which a thermal block may be placed in contact and/or a decrease in thickness of the layers of the substrate that a thermal block must act on.

According to various embodiments, a multi-chambered substrate may include a plurality of micro-sized vent holes in the film layer that, together with the base, forms the fluid distribution network (e.g., sample chambers, main fluid channel, sample introduction channels, venting channels, and venting chambers) in the substrate. The micro-sized vent holes may function both as capillary stops to prevent leakage of sample from a filled substrate and as vents to release gas from the substrate.

Figure 17:
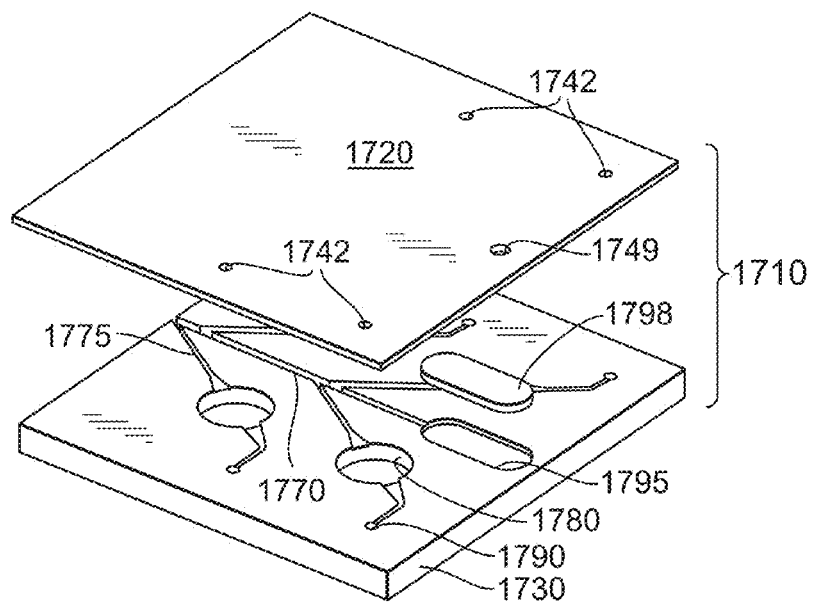
FIG. 17 is a perspective, isometric view of yet another substrate for biological analysis according to various embodiments of the present teachings.

A partial, isometric, perspective view of a multi-chambered substrate 1710 that eliminates the need to provide a membrane over each venting chamber is depicted in FIG. 17. The substrate 1710 includes a base 1730 and a film layer 1720 that is adhered to the base 1730. The base 1730 defines a plurality of features and, with the layer 1720 placed in position over the base, defines a main fluid channel 1770 configured to receive the sample supplied to the substrate 1710 and distribute the sample to a plurality of sample introduction channels 1775 that are in flow communication to in turn supply the sample to a plurality of sample chambers 1780. Each of the sample chambers 1780 is in flow communication with a venting chamber 1790 via a venting channel 1700.

The film layer 1720 is provided with a plurality of micro-sized vent holes 1742 configured and arranged to be aligned with the venting chambers 1790 when the film layer 1720 is in position on the base 1730. By way of example only, the film layer 1720 may be a PSA film layer with adhesive on one side used to attach the film layer 1720 to the base 1730. The film layer 1720 may be, for example, a PSA polymer film or a PSA metal film. The vent holes 1742 may be sized so as to allow gas to escape from the substrate 1710 while creating a fluidic stop that prevents the sample within the substrate from leaking through the holes 1742. For example, capillary forces may prevent the sample from passing through the holes 1742 and out of the substrate 1710. In various exemplary embodiments, the vent holes 1742 may have a dimension (e.g., a diameter) ranging from about 1 µm to about 10 µm, for example, about 5 µm. In some embodiments, areas surrounding the vent holes 1742 may be substantially free of adhesive to prevent adhesive from flowing (e.g., cold-flowing) into and reducing the diameter of the vent holes.

In some cases, it may also be desirable to provide venting at the end of the fill channel 1770. Thus, the exemplary embodiment of FIG. 17 also includes a venting chamber 1795 and corresponding vent membrane 1798 provided at the end of the main fill channel 1770. The membrane 1798 may be contained in the venting chamber 1795 between the film layer 1720 and the base 1730, for example, similar to the membranes 50 discussed with reference to the exemplary embodiment of FIGS. 2A and 2B. The membrane 1798 thus may be sized and configured to substantially fill the venting channel 1795. The membrane 1798 may be made of any material described herein as suitable for such porous or gas-permeable membranes. A vent hole 1749, which may be formed in the same manner and may have a similar structure as the vent holes 1742, may be provided in the film layer 1720 in a position aligned with the membrane 1798 and venting chamber 1795. The venting chamber 1795 is relatively large compared to the venting chambers 1790. Although the exemplary embodiment of FIG. 17 depicts the use of the venting chamber 1795, the membrane 1798, and the vent hole 1749, a substrate like that in FIG. 17 but that does not include those features is also considered as within the scope of the invention. In such a case, sufficient venting may be provided solely by the use of vent holes 1742 corresponding to each venting chamber 1790.

Various techniques may be used to provide the micro-sized vent holes 1742 in the film layer 1720. According to various embodiments, laser micro-machining (e.g., drilling) may be used to form the holes 1742 in the film layer 1740. For example, a laser micro-machining process may be used to drill holes through the film layer 1740 after it has been attached to the base 1730, without penetrating the base 1730. One exemplary laser micro-machining process developed by Oxford Lasers, Inc. (Oxon, United Kingdom) uses an ultraviolet cold laser process capable of drilling holes having a dimension (e.g., diameter) ranging from about 5 µm to about 10 µm in the film layer 1720. This process may form about 10 holes to several hundred holes per second, for example about 16 holes per second, in the film layer 1720 after the film layer 1720 has been bonded to the base 1730, without damage to the base 1730.

Figure 18A:
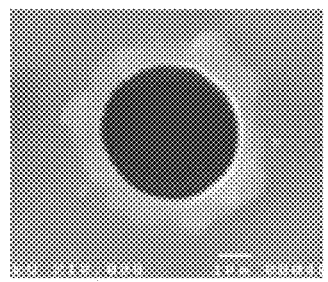
FIGS. 18A-18C illustrate perspective views of vent holes formed in various materials via Oxford Laser, Inc. instruments.
Figure 18B:
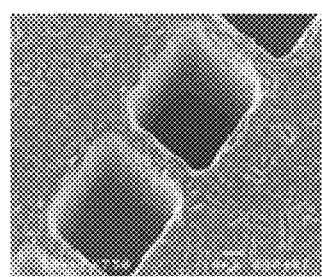
Figure 18C:
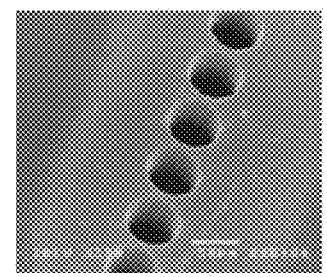

The laser drilling process can be applied to a variety of materials, including, but not limited to, for example, silicon, glass, metal, and/or polyimide. Examples of holes laser-drilled in various materials using Oxford Lasers, Inc. instruments are shown in FIGS. 18A-18C. In particular, FIG. 18A shows a laser-drilled hole of about 5 µm in diameter in steel, FIG. 18B shows 2 square laser-drilled holes with each side being about 50 µm formed in silicon, and FIG. 18C shows several holes about 50 µm in diameter formed laser-drilled in Kapton.

A technique that permits vent holes 1742 to be formed in the film layer 1720 after the film layer 1720 has been bonded to the base 1730 eliminates the need to precisely align the film layer with the base, which may thereby facilitate manufacturing. In other words, in a film layer that has pre-formed holes, precise alignment of the film layer with the base during bonding is needed to ensure alignment of the pre-formed holes with the venting chambers. Moreover, a micro-machining technique for forming the holes, such as that described above, for example, permits the size (e.g., diameter) of the vent holes to be altered as desired and progressively. This may permit control over the pressure gradient along the fill path during filling of the substrate.

Although the exemplary embodiment of FIG. 17 depicts a single vent hole 1742 corresponding to each venting chamber 1790, it should be understood that one or more vent holes 1742 may be provided in communication with each venting chamber 1790. The number of vent holes per venting chamber may be selected based on a variety of factors, including size of the vent holes, desired venting of the gases in the substrate, minimization of leakage of sample from the substrate, and other factors. Results of tests performed for substrates having differing number of vent holes associated with each venting chamber are provided below.

Figure 19:
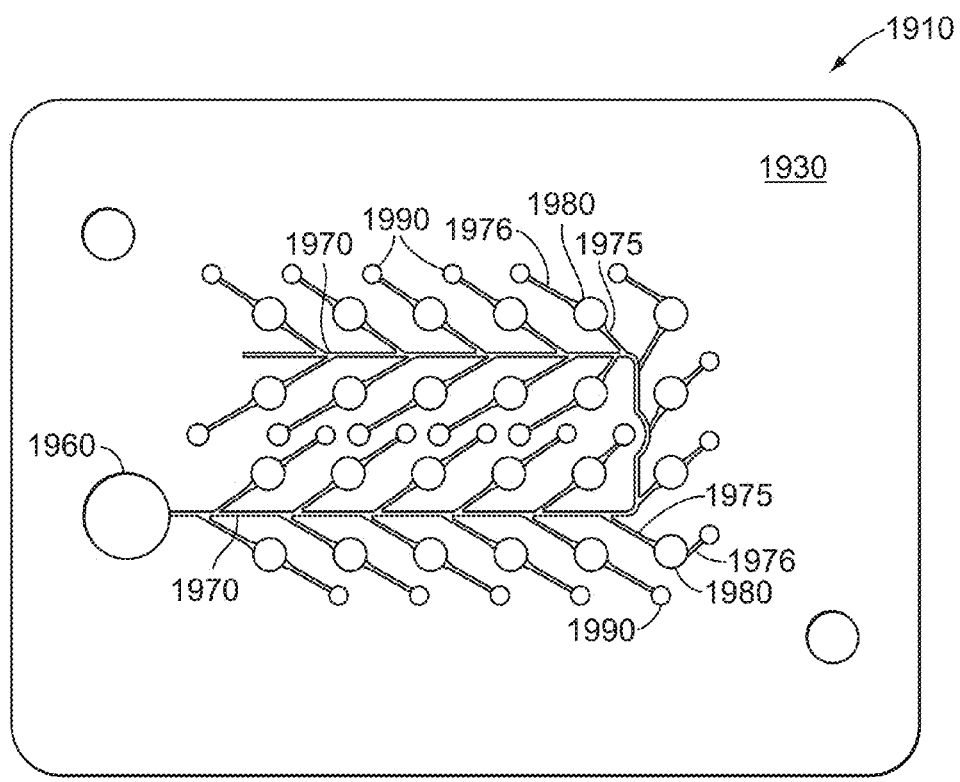
FIG. 19 is a perspective view of yet another substrate for biological analysis according to various embodiments of the present teachings.

Filling tests were performed on substrates defining a 24 sample-chamber array having a configuration substantially as shown in the partial schematic representation of the substrate 1910 depicted in FIG. 19. In FIG. 19, the arrangement of the sample chambers 1980, inlet channels 1975, venting channels 1976, venting chambers 1990, main fluid channel 1970, and sample supply inlet 1960 are shown. The substrate used for the tests also included a film layer like the film layer 1720 with vent holes 1742 aligned with the venting chambers 1990. The substrates 1910 were made of a COP base covered with an aluminum PSA film layer that included a 5 mm thick aluminum layer with a 1.5 mm thick PSA laminate layer.

In a first test configuration, a single vent hole of approximately 10 μm in diameter was laser-drilled in the film layer and aligned with each venting chamber. In a second test configuration, three vent holes of approximately 10 μm in diameter were laser-drilled in the film layer and aligned with each venting chamber. In a third test configuration, six vent holes of approximately 10 μm in diameter were laser-drilled in the film layer and aligned with each venting chamber. A syringe pump was used to supply a red dye fluid to each substrate at a pump speed of 40 μl/minute. Red dye was used to assist in observing the flow and filling in the substrate.

For the first test configuration using a single hole for each venting chamber 1990, no leakage was observed during filling. For the second test configuration using three holes for each venting chamber 1990, single droplet leakage was observed for three vent locations. For the third test configuration using six holes for each venting chamber 1990, single droplet leakage was observed in two vent locations. Those skilled in the art would understand that the number and/or size of vent holes provided for each venting chamber may vary based on a variety of factors, including, the sample being introduced, the pressure in the substrate, and other factors. Overall, the size and number of vent holes may be chosen so as to substantially prevent leakage of sample through the one or more vent holes and out of the device, while permitting gas (e.g., air) to escape through the one or more vent holes.

Various exemplary embodiments may utilize a hydrophobic, porous filter, substantially in the form of a fiber-like configuration, in lieu of a venting membranes described earlier, to permit gas (e.g, air) to escape the substrate while preventing sample leakage therethrough. Although the embodiments described below use a hydrophobic, porous fiber member, it may also be possible to utilize a porous or gas-permeable membrane material formed into a fiber-like structure. With reference to FIG. 44, an exemplary embodiment of a substrate 4410 for biological sample analysis is depicted. The substrate 4410 includes a base 4430 and a film layer 4420 covering the base 4430. The substrate 4410 defines a sample distribution network including an array of sample chambers 4480 in flow communication with a plurality of main fluid supply channels 4470 via sample introduction branch channels 4475. Each sample chamber 4480 also is in flow communication with a main venting channel 4472 via branch venting channels 4476. A hydrophobic, porous fiber 4400 may be placed in the main venting channel 4472, as shown in FIGS. 44 and 44A. Thus, rather than each sample chamber 4480 terminating in an individual venting chamber, as described in other embodiments herein, a group of sample chambers 4480 terminates in a common venting channel 4472. As shown in the close-up view of FIG. 44A, the film layer 4420 may be provided with vent holes 4425 aligned with the main venting channel 4472. Each adjacent pair of chambers 4480 and corresponding venting channels 4476 may be associated with a vent hole 4425, as depicted in FIG. 44A. The vent holes 4425 may permit gas to escape through the fibers 4400 and out of the substrate 4410. The vent holes 4425 may be formed via a variety of techniques, including the laser process described above with reference to FIG. 17. In an alternative embodiment, rather than providing vent holes 4425 in the film layer 4420, vent through holes may be formed from the venting channel 4472 through the depth of the base 4430, opening to the bottom of the base 4430 shown in FIGS. 44 and 44A.

The hydrophobic porous fibers 4400 may have a configuration similar to such fibers used in the filtration industry to filter impurities from water pumped into the fiber at pressures higher than the outside of the fiber. Such fibers permit impurities to flow through the pores of the fiber wall while water is retained. In various other exemplary embodiments, the fibers 4400 may be in the form of a resilient fiber cord that has a porous hydrophobic coating. Similarly, in the case of use with a substrate for biological testing, the filter 4400 can permit gas (e.g., air) to pass therethrough while retaining sample. Thus, with the fibers 4400 in place in the substrate 4110, gas may be permitted to pass through the main venting channels 4172 and fibers 4400 and out of the substrate 4410 through vent through holes.

Figure 45:
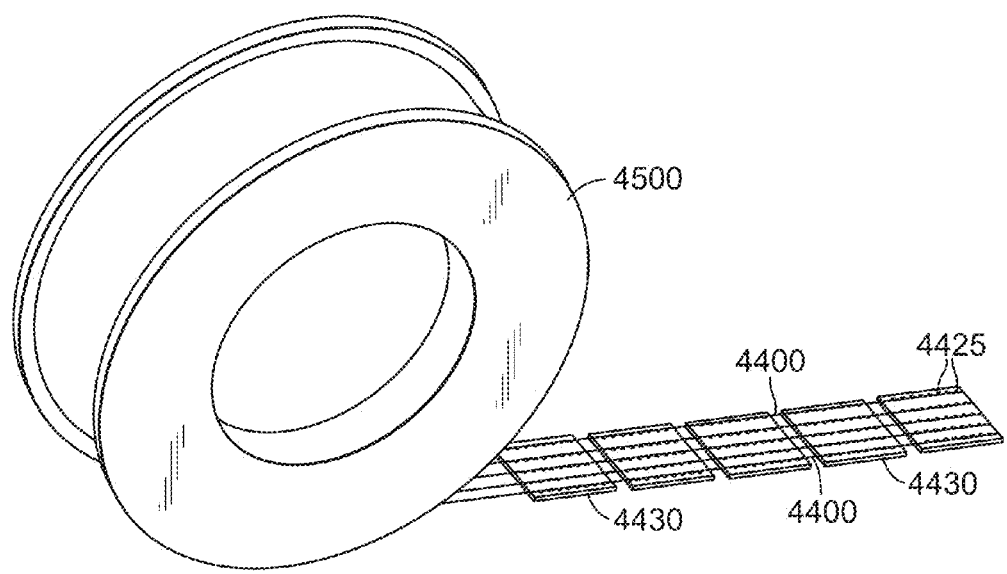
FIG. 45 is a perspective view of a device for inserting porous fibers in substrates for biological analysis according to various embodiments of the present teachings.

FIG. 45 shows an exemplary technique for placing the fibers 4400 in an assembly-line fashion into a plurality of bases 4430 to form substrates 4410. A fiber supply roller 4500 may supply a plurality of separate fibers 4400, for example, corresponding to at least the number of main venting channels 4172 in a substrate. The fibers 4400 may be secured in position in the main venting channels 4172 in the first base 4430 and the first base 4430 may move down a belt or other similar device, thereby pulling the fibers 4400 with it. As the bases 4430 move to the right shown in FIG. 45, new bases 4430 to be supplied with fibers 4400 are added to the left end. After a desired number of bases 4430 have been supplied with fibers 4400, a film layer may be adhered to the bases 4430 and the parts cut away from each other in the spaces between the parts shown.

Figure 46A:
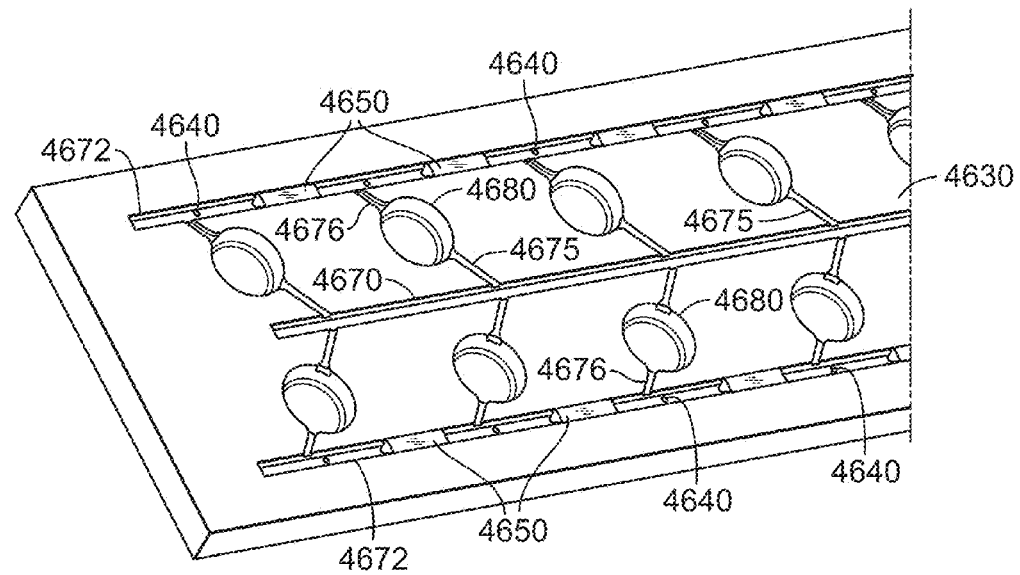
FIGS. 46A-46D show exemplary steps for making the substrate of FIG. 44.
Figure 46B:
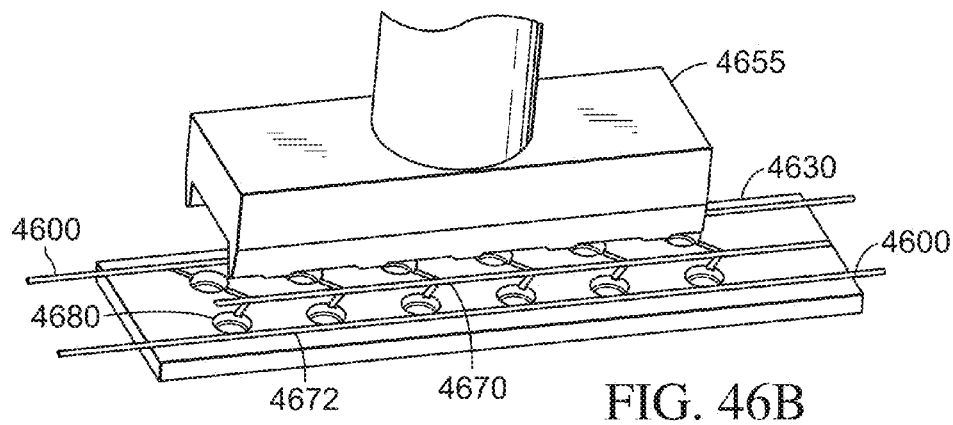
Figure 46C:
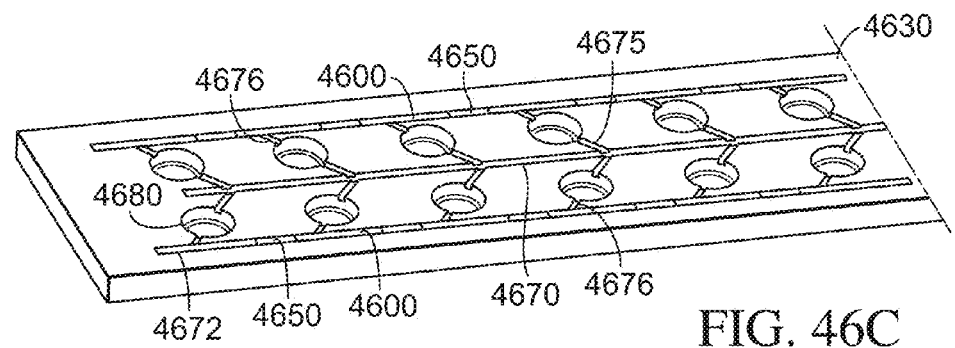

FIGS. 46A-46C show an exemplary embodiment for securing hydrophobic porous fibers in place in venting channels of a base portion of a substrate. For simplicity, the base 4630 depicted in FIGS. 46A-46C shows only two rows of sample chambers 4680 in flow communication with a common main fluid supply channel 4670 and differing main venting channels 4672. FIG. 46A depicts the base 4630 prior to the placement of the fibers 4600 in the channels 4672. A plurality of weld spots 4650 are deposited along the length of each of the main venting channels 4672 in positions between where adjacent venting channels 4676 intersect the main venting channels 4672. By way of example, the weld spots 4650 may be formed from a low melting point polymer deposited in the channels 4672, for example, via an ink-jet type of device. In another example, the base 4630 may be molded with the weld spots 4650. Between the weld spots 4650, vent through holes 4640 may be provided in the base from the channels 4672 to the bottom of the base 4630 in order to permit gas to escape the substrate 4610. Alternatively, such vent through holes may be provided in the film layer that covers the base 4630, as has been described herein.

As shown in FIG. 46B, the fibers 4600 may be placed in the channels 4672, for example via a fiber supply tool as was described with reference to FIG. 45 above. A heated pressing instrument 4655 may be used to press the fibers 4600 into the channels 4672, preferably while the fibers 4600 are held in tension. At the same time, the heated instrument 4655 melts the weld spots 4650 to fuse the weld spots 4650 and fibers 4600 together at the locations of the weld spots 4650, as shown in FIG. 46C. This melting process may serve to block the paths between the sample chambers 4680 and thus may serve as a sealing mechanism for sealing the chambers 4680. A series of bases 4630 may be formed in this way using the assembly line process discussed in FIG. 45, with the film layers being applied and the substrates being separated from each other by cutting the fibers as described above. In other embodiments, a heated instrument may be used after the film layer 4620 has been applied in order to fuse the weld spots 4650 and fibers 4600 together and at the same time bond the film layer 4620 to the base 4630.

In yet further various embodiments, the instead of the weld spots 4650, a two layer laminated material may be used.

Figure 46D:
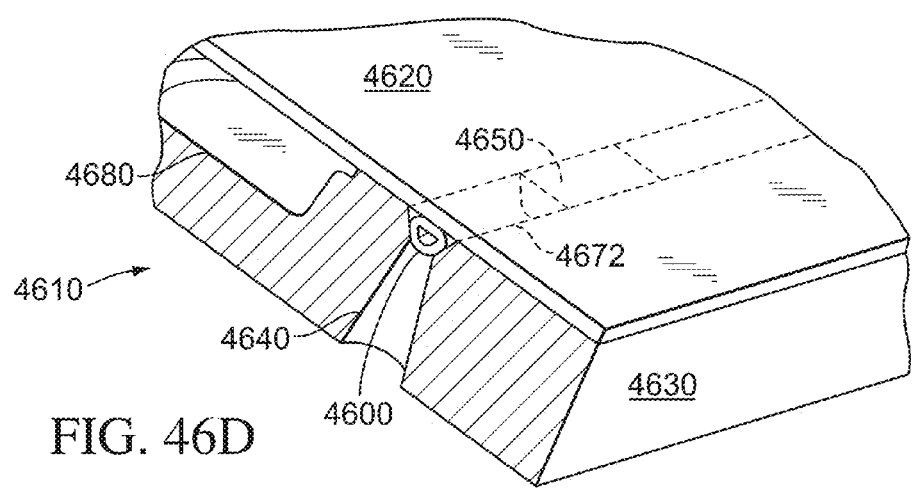

FIG. 46D depicts a partial cross-section of the completed substrate 4610 with the film layer 4620 adhered to the base 4630. The cross-section in FIG. 46D is taken through a vent through hole 4640. As shown in FIG. 46D, the main venting channel 4672 may have a depth that is less than a diameter of the fiber 4600 such that the film layer 4620 presses down on the top of the fiber 4600 to hold the fiber against the bottom of the channel 4672 and seal off the vent through hole 4640 to ensure that no sample leaks around the fiber 4600 and escapes through the through hole 4640. If needed, the substrate 4610 may be held against a flat plate or the like during filling to prevent the film layer 4620 from bulging rather than maintaining a tight seal like that shown in FIG. 46D.

Figure 47A:
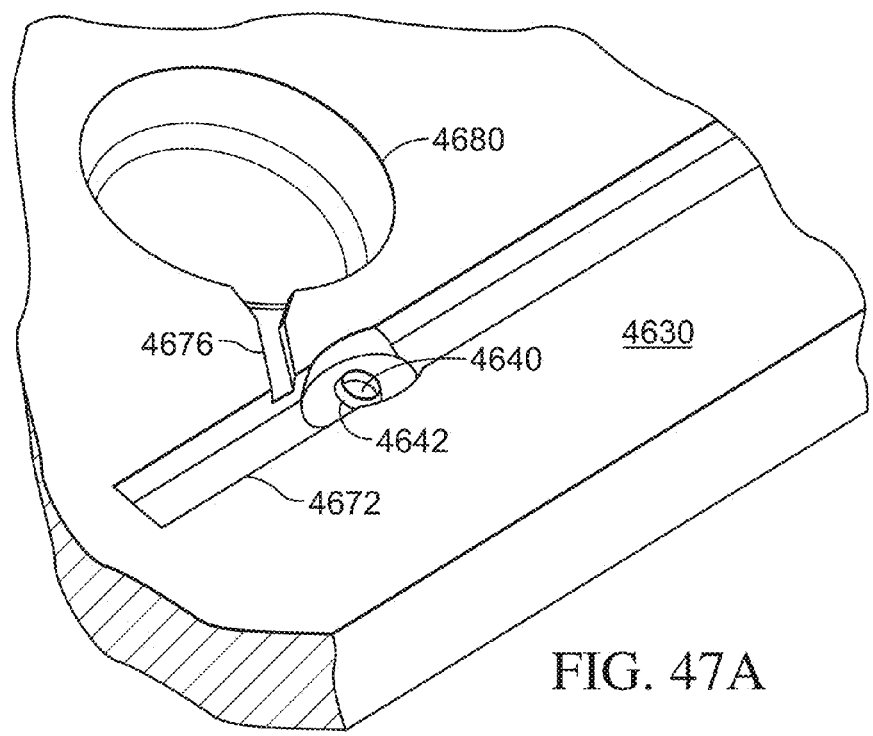
FIGS. 47A and 47B are a partial perspective and cross-sectional view of a substrate for biological analysis according to various embodiments of the present teachings.
Figure 47B:
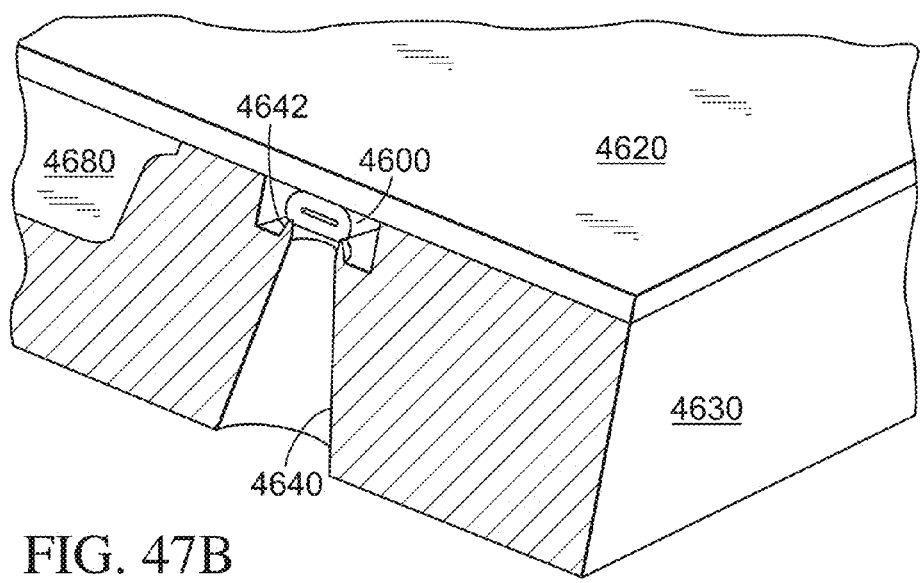

To further improve sealing of the vent through holes 4640 with the fiber 4600, a circular seal ring 4642 may be provided around the vent through hole opening in the channel 4672, as shown in FIGS. 47A and 47B. The ring 4642 may have a raised surface relative to the bottom surface of the channel 4672 and provide a flat surface to press against the fiber 4600 rather than, for example, a rounded surface of the bottom of the channel 4672. Further, because the surface of the seal ring 4642 is slightly raised relative to the bottom of the channel 4672 in the area of the vent through hole 4642, a better seal may be achieved between the fiber 4600 and the vent through hole 4642.

Although FIG. 47B depicts a hollow tubular fiber structure, it should be understood that porous hydrophobic fibers in accordance with the present teachings may have a variety of cross-sectional shapes, including, but not limited to, for example, a solid circular cross-section (e.g., a rod).

Figure 49:
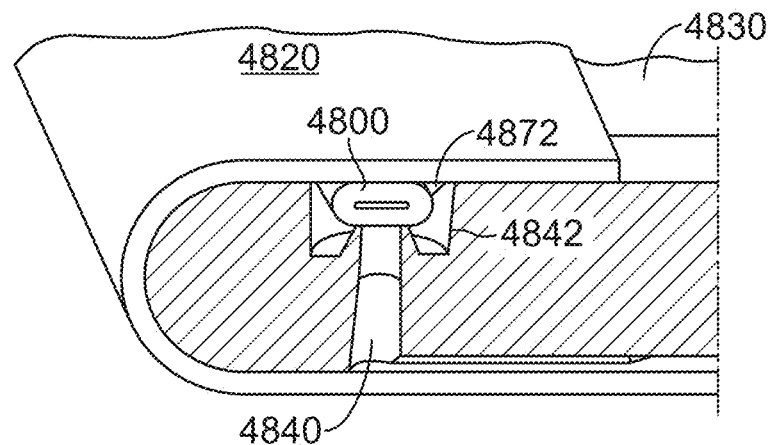
FIG. 49 is a partial cross-sectional view of the substrate of FIGS. 48A-48C.
Figure 50:
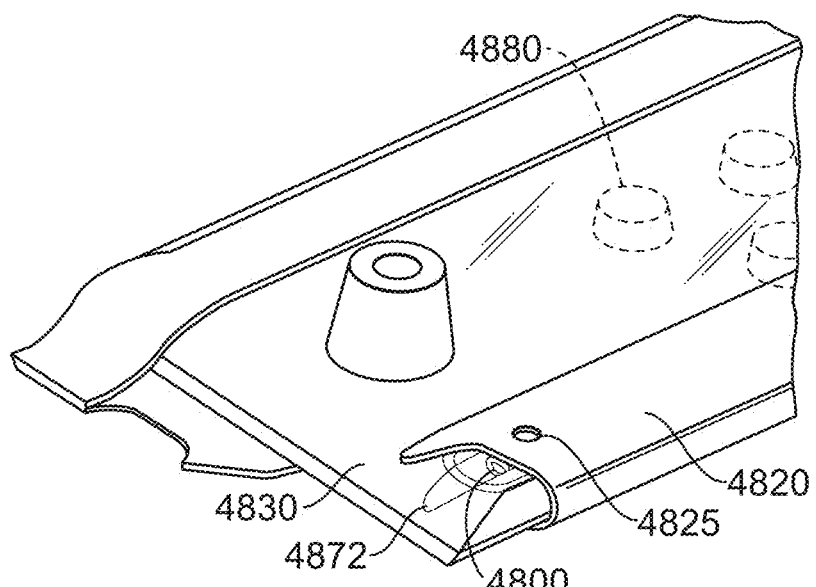
FIG. 50 is a partial perspective view of the substrate of FIGS. 48A-48C.

FIGS. 48-50 show another exemplary embodiment of a substrate 4810 that includes a porous, hydrophobic fiber 4800 for retaining sample in the substrate while permitting gas to escape. FIGS. 48A and 48B show opposite sides of the base portion 4830 of the substrate 4810, while FIG. 48C shows the substrate 4810 including film layer 4820 as viewed from the same side as in FIG. 48B. In the embodiment of FIGS. 48A-48C, the base 4830 is transparent and the film layer 4820 may be metallic, such as, for example, an aluminum PSA film layer. However, it should be understood that the base 4830 and film layer 4820 may be made of any materials described herein as suitable for making a base and film layer. To avoid confusion between features of the substrate 4810 on the near and far sides, FIGS. 48A and 48B are shown as being opaque.

With reference to FIG. 48A, the substrate 4810 may comprise a base 4830 that, together with the film layer 4820, defines a sample distribution network that includes a plurality of sample chambers 4880 which all connect to a common main fluid supply channel 4870. Each chamber 4880 is in flow communication with the main fluid supply channel 4870 via a sample introduction channel 4875. Each chamber 4880 also is in flow communication with a venting channel 4876 that leads to a main venting channel 4872 provided in the side of the base 4830 facing up in FIG. 48B, i.e., opposite to the side in which the other features discussed above are provided. The substrate 4810 further includes a sample inlet port 4860 in flow communication with the main fluid supply channel 4870. An initial portion 4865 of the main fluid supply channel 4870 may have a serpentine configuration so as to permit passive mixing of the sample, for example, of an eluted sample, prior to introducing the sample to the introduction channels 4875. A more detailed explanation of using a serpentine channel to achieve sample mixing is provided below.

A hydrophobic, porous fiber 4800 may be provided in the main venting channel 4872 in a manner similar to that described above with reference to the exemplary embodiments of FIG. 44-47. As shown in FIG. 48C and the close up views of FIGS. 49 and 50, a film layer 4820 may cover the side of the base 4830 shown in FIG. 48A and a portion of the film layer 4820 may wrap around the base portion to cover and seal the channel 4872 and fiber 4800. Flow communication between the venting channels 4876 and the main venting channel 4872 may be provided via a vent through hole 4840 that leads from the end of the venting channels 4876 to the venting channel 4872. According to various exemplary embodiments, in a manner similar to that described above in FIGS. 47A and 47B, the vent through holes 4840 may terminate in the main venting channel 4872 in a raised sealing rim 4842 that presses against the fiber 4800, as shown in partial cross-sectional view of FIG. 49.

Vented air may pass into the porous fiber 4800, which may be in the form of a hollow tube as shown or may have other configurations, as described above. The air may pass down the fiber 4800 and/or exit the fiber 4800 into the channel 4872 that the fiber 4800 lies in. According to various embodiments, a single vent hole 4825, shown in FIG. 50, may be provided in the film layer 4820 and aligned with the main venting channel 4872, permitting any air leaving the substrate 4810 to pass therethrough. Providing a single vent hole 4825 may limit the potential of sample escaping from the substrate due, for example, to improper sealing of the vent passages after filling the substrate 4810. However, it should be understood that plural vent holes also may be formed in the film layer 4820 to allow air to escape therethrough.

Figure 51A:
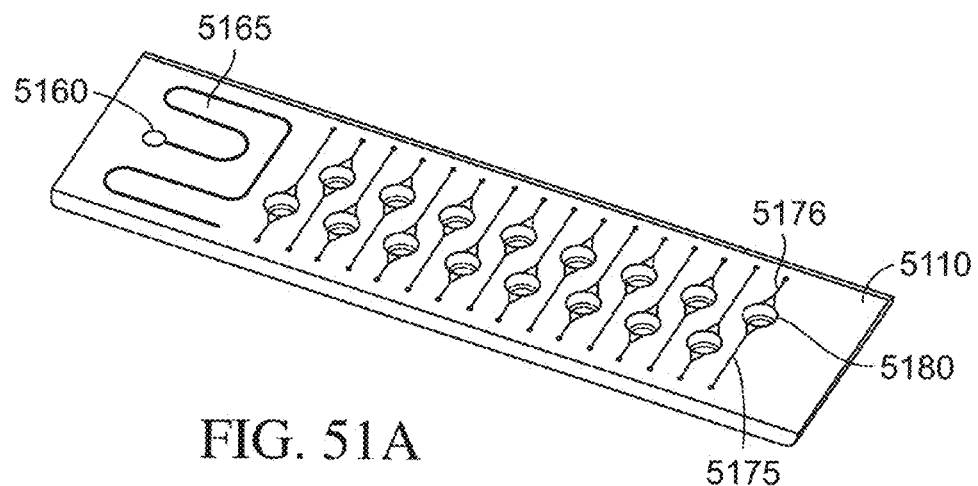
FIGS. 51A and 51B are perspective views of yet another substrate for biological analysis according to various embodiments of the present teachings.
Figure 51B:
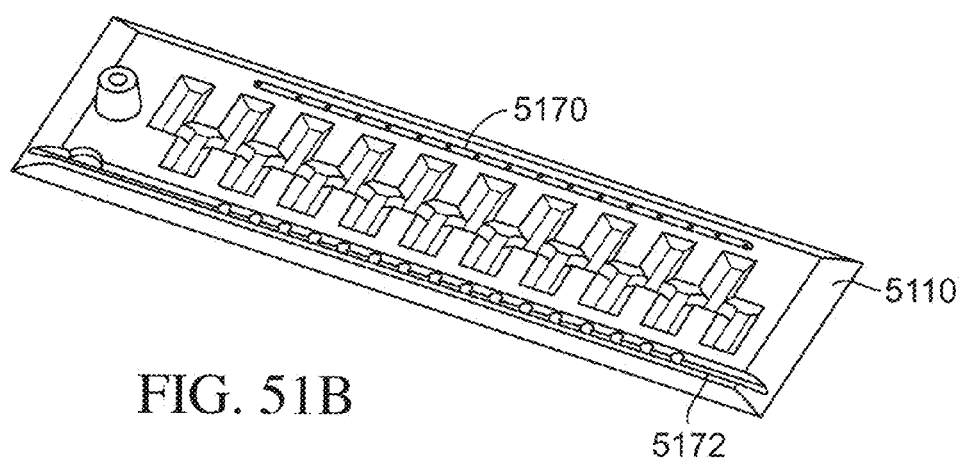

FIGS. 51A and 51B show the opposing sides of another substrate provided with a porous, hydrophobic fiber venting member according to various embodiments of the present teachings. The substrate 5110 of FIGS. 51A and 51B has substantially the same structure as the substrate 4810 described above, except that the main fluid supply channel 5170 is provided in the same side of the base 5130 as the main venting channel 5172. The two channels 5170 and 5172 are depicted in the view of FIG. 51B and are on a side of the substrate opposite to the chambers 5180, sample introduction channels 5175 and venting channels 5176. As with the main venting channel 5172, flow communication between the introduction channels 5175 and the main fluid supply channel 5170 may be provided via through holes (not shown) in the base 5130. The configuration of FIGS. 51A and 51B may permit isolation of the sample chambers 5180 via a sealing (staking) mechanism on the detection side (e.g., the side shown in FIG. 51B) of the substrate 5110. This may allow the sealing mechanism to be provided on a portion of instrumentation that is not part of a thermocycler and thus may be made of materials that do not need to take thermal properties into consideration.

Providing the sample chambers 4880 and 5180 in two rows, as shown in the exemplary embodiments of FIGS. 48-51 may be advantageous in that all of the chambers 4880 and 5180 are positioned at an outer perimeter of the substrate 4810 and 5110. This may avoid edge effects that may cause interior chambers of a substrate to experience differing temperatures than temperatures of chambers at a perimeter of the substrate. Thus, all of the chambers may have a substantially uniform temperature, for example, during thermocycling of the substrate. Even in the case where one row of chambers is hotter than the other row of chambers if the temperature difference is uniform between the two rows, the temperature of the chambers may be uniform. Further, due to the relatively small size of the substrates 4810 and 5110, for example, in the configuration shown that includes 16 chambers, a smaller thermal block may be used with reduced margin on either side, which may decrease the overall size of the instrumentation used for biological testing of the substrates 4810 and 5110.

Although the exemplary substrates 4810 and 5110 include an array of two rows of chambers 4880 and 5180, the substrates may be formed with any number of chamber rows. By way of example only, the substrates may be formed with four rows of chambers, in which case a main fluid supply channel may be positioned between a first pair of chamber rows and a second pair of chamber rows. Two venting channels may then be provided at the two opposite edges of the substrate in conjunction with each of the pair of rows of chambers. Any number of rows may be used, with the porous, hydrophobic filters disposed inward from the edges of the substrate being secured in position by a separate film or series of strips of film on the underside of the substrate. The substrates also may include negative template control sections, described in more detail with reference to the embodiments of FIGS. 26 and 27, which according to various embodiments may be provided substantially in the center of the substrate array with corresponding sample inlet ports.

Figure 52:
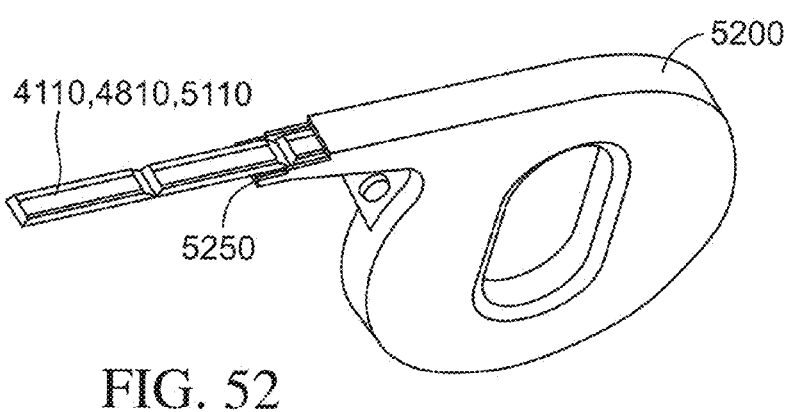
FIG. 52 is a perspective view of a system for packaging a plurality of substrates for biological analysis according to various embodiments of the present teachings.

The substrates 4810 and 5110 may be assembled in a manner similar to that described above with reference to FIG. 45, that is, in a continuous fashion by tensioning the fibers 4800 and 5100 from a roll and making plural substrates 4810 and 5110 in an assembly line. According to various embodiments, after applying the film layer to the bases, as described with reference to FIG. 45, the substrates 4410, 4810, and 5110 may be left in a continuous strip-like configuration (e.g., without separating the individual substrates) and packaged in a reel 5200, as shown in the exemplary embodiment of FIG. 52. The reel 5200 may have a cutter mechanism 5250, similar to a tape reel, in order to separate individual substrates as desired. According to yet other exemplary embodiments, the substrates may be left connected to one another and supplied in an automated manner to a processing instrument, such as, for example, a thermocycler or the like, in a continuous and/or high throughput manner. This may permit processing of the substrates without an operator handling each substrate individually, which could potentially contaminate and/or damage each substrate. Those having ordinary skill in the art would understand how to package any of the substrate embodiments herein in a continuous reel mechanism like that of FIG. 52.

Figure 53A:
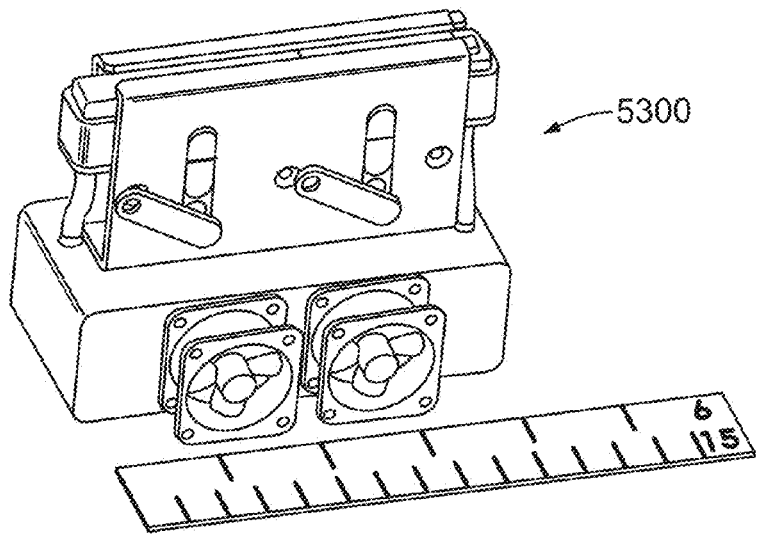
FIGS. 53A and 53B are a perspective and cross-sectional view of a thermocycler in accordance with various embodiments of the present teachings.
Figure 53B:
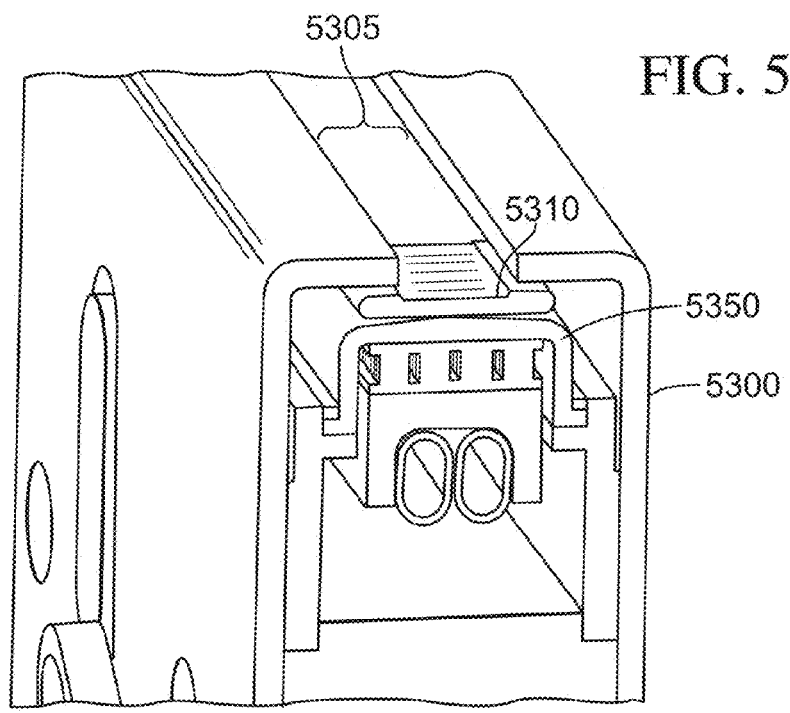

In yet other embodiments, a thermocycler may be configured to accommodate two sample substrates, for example, substrates 4810 or 5110. A perspective view of such a thermocycler 5300 is depicted in FIG. 53A and a partial cross-sectional view is depicted in FIG. 53B. The substrates could be processed at both ends of the thermocycler 5300 (e.g., the left and right sides) shown in FIG. 53A. As shown in FIG. 53B, the thermocycler 5300 may be provided with a heated plate (thermal block) 5350 having a crowned profile and pressure may be applied to the chamber array by providing pressure on the outer edges of the substrate 5310 without transmitting force through the open area (or window) 5305 directly over the sample chambers of the substrates. A relatively thin, narrow heated plate 5350 may be used and transmit sufficient clamping force to the side walls of the substrates rather than through a Peltier device or other component.

As discussed above, control over the pressure gradient along the fill path during filling of the substrate may be provided, for example, by controlling the size of vent holes, such as vent holes 1742 provided in the substrate 1710, as was described in relation to the embodiment of FIG. 17. Other techniques also may be used, either alone, in combination with the vent holes or other substrate configurations in accordance with the disclosure, and/or in combination with each other, to provide control over the pressure gradient during filling of a substrate via positive pressure. It may be desirable to control the pressure gradient by creating a higher pressure in the venting channels so as to reduce the potential for leakage from the substrate (e.g., through the vent holes in a film layer).

By way of example, the hydrophobicity of the venting channels of the substrate may be modified, for example increased, to control the pressure gradient while filling the substrate with sample. The hydrophobicity may be modified, for example, by adding texture and/or increasing roughness (e.g., on a nano-scale level) to the surface defining the venting channels. Such texturing and/or increasing roughness may be introduced during the injection molding process, for example, by texturing the mold as desired in the area that forms the venting channels. Other techniques for modifying the hydrophobicity of a surface defining the venting channels may include providing a coating, or chemically treating the surface. By way of example only, Kim et al., "Nanostructured Surfaces For Dramatic Reduction Of Flow Resistance In Droplet-Based Microfluidics," IEEE 2002, hereby incorporated by reference in its entirety herein, teaches one technique for providing nanostructures on a surface to alter hydrophobicity. It is envisioned that the hydrophobicity of all or a portion of the venting channels may be altered.

Figures 20A, 20B:
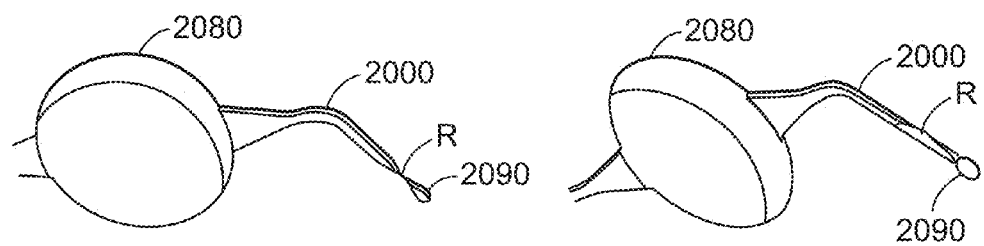
FIGS. 20A and 20B illustrate perspective views of sample chambers, venting channels, and venting chambers according to various embodiments of the present teachings.

According to various embodiments, the venting channel configuration (e.g., geometry) also may be modified in order to control the pressure gradient during filling of the substrate. For example, the venting channels may be provided with a region of reduced cross-section so as to increase the pressure within the venting channel and reduce the potential for leakage. With reference to the exemplary embodiments of FIGS. 20A and 20B, a sample chamber 2080 and corresponding venting channel 2000 in flow communication with the chamber 2080 is depicted. As shown, the venting channel 2000 may be provided with a reduced cross-section R, for example, toward an end of the venting channel 2000 that leads to the venting chamber 2090. In the exemplary embodiment of FIG. 20A, the reduced cross-section R is achieved by narrowing the side walls defining the channel 2000. In the exemplary embodiment of FIG. 20B, the reduced cross-section R is achieved by raising the bottom surface of the channel 2000 at the location R in comparison to the remainder of the bottom surface of the channel. In other words, the depth of the channel 2000 is less at the location than the depth of the remainder of the channel.

According to various embodiments, for example, when filling a multi-chambered substrate via positive pressure (e.g., via pumping, syringe, etc.), it is desirable to know when to stop the filling once the various chambers and channels have been filled in order to control over-pressurization and/or sample leakage. An exemplary mechanism for determining when to stop filling the substrate includes providing optical sensors in association with the sample chambers. The sensors, which in an exemplary embodiment may be an optical sensor including a photodiode and LED, can detect the presence of the sample by a difference in the index of refraction and send a signal to stop the filling process (which may occur either manually or automatically). Due to potential increased costs and manufacturing complexity associated with such a sensor/feedback mechanism, it may be desirable to provide a relatively simple substrate design configured to passively and automatically stop sample delivery so as to avoid over-pressurization and/or leakage of the substrate.

Figure 21A:
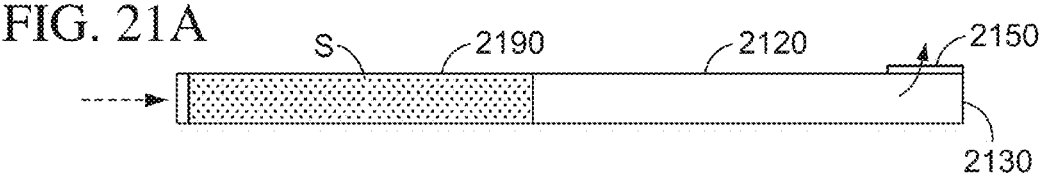
FIGS. 21A-21C schematically illustrate cross-sectional views of exemplary steps of filling a feature of a substrate for biological analysis.
Figure 21B:
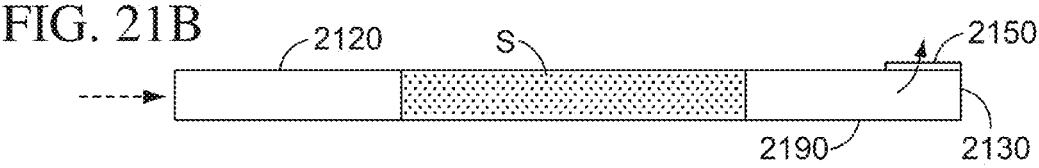
Figure 21C:
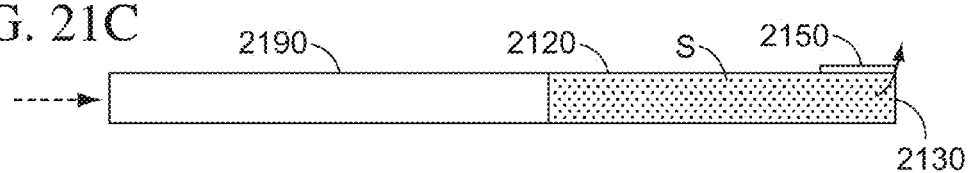

FIGS. 21A-21C schematically depict exemplary steps of filling a multi-chambered substrate that includes a venting mechanism, such as, for example, either a vent membrane or vent hole, as have been described above. It should be noted that FIGS. 21A-21C are simplified for the purposes of showing the principles of filling channels and/or chambers of a substrate and leakage of fluid that may occur due to over-pressurization. Thus, in the figures, only a single channel is illustrated with a vent positioned at a distal end of the channel.

Referring to FIG. 21A, a volume of sample S is delivered, for example, via positive pressure, at an end of the channel 2190 (or chamber) opposite to an end at which vent membrane 2150 is disposed. The dashed arrows in FIGS. 21A-21C indicate the direction of sample delivery and movement through the channel 2190, with the shaded area representing the sample S and the nonshaded area representing gas (e.g., air). The channel 2190, in an exemplary configuration, may be defined by a base portion 2130 and a film layer 2120, with the film layer 2120 comprising a vent hole (not shown) positioned beneath the membrane 2150 to permit gas to escape therethrough. In FIG. 21A, as the sample S is forced via pressure through the channel 2190, gas (e.g., air) residing in the channel 2190 is compressed and passed out of the channel 2190 through the vent hole (not shown) and the gas-permeable membrane 2150, as shown by the solid arrow proximate the membrane 2150. As the sample S continues to move downstream in the channel 2190 (e.g. toward the membrane 2150), gas that is between the sample S and the end of the channel 2190 continues to be released through the vent membrane 2150, as shown in FIG. 21B.

Eventually, due to the continued positive pressure applied at the end of the channel 2190 proximate the dashed arrow, as shown in FIG. 21C, the sample S reaches a location in the channel 2190 corresponding to the vent hole (not shown) and membrane 2150 (e.g., the end of the channel 2190 opposite the end to which pressure is applied). If further pressure is applied after the sample S reaches the position shown in FIG. 21C, the channel 2190 becomes over-pressurized and the sample S may leak out of the vent hole and membrane 2150. For example, in the case of a gas-permeable, liquid impermeable membrane 2150, the membrane may burst due to over-pressurization and/or sample S may leak around the edges of the membrane 2150, as depicted by the arrow in FIG. 21C.

In FIGS. 21A-21C, it should be understood that the membrane 2150 may be eliminated and a vent hole of micro-size may be used instead, as described, for example, with reference to the embodiment of FIGS. 17 and 19.

Leakage of sample out of the substrate may depend upon various factors, including, for example, the configuration of the substrate, the applied pressure, the method of pressure generation (e.g., via syringe, pump, constant pressure source, etc.), properties of the membrane material and/or configuration of vent holes, and other factors that may influence the extent to which the substrate becomes over-pressurized during filling with sample.

Figure 22A:
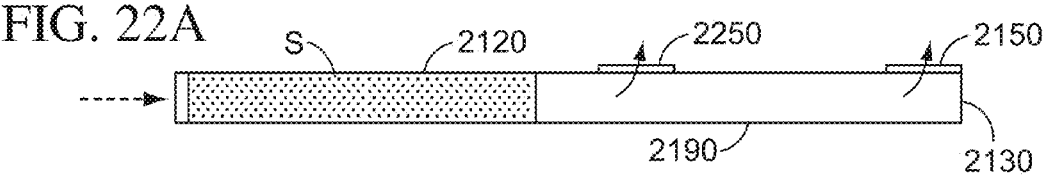
FIGS. 22A-22C schematically illustrate cross-sectional views of exemplary steps of filling a feature of a substrate for biological analysis according to various embodiments of the present teachings.
Figure 22B:
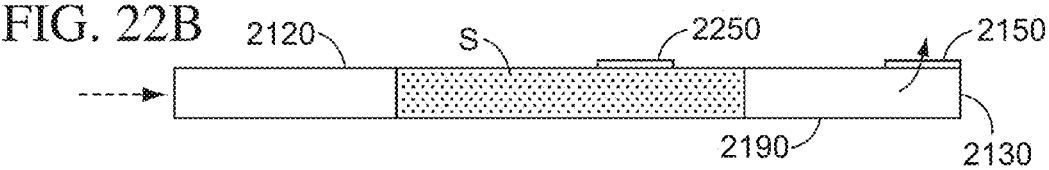
Figure 22C:
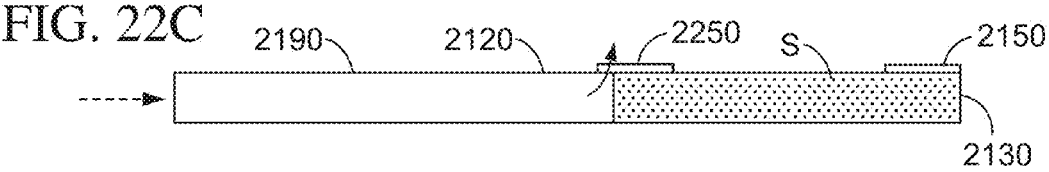

According to various embodiments, providing an additional vent upstream of the vent 2150 of FIGS. 21A-21C may alleviate over-pressurization and leakage. FIGS. 22A-22C schematically depict the filling process that occurs for the channel 2190 of FIGS. 21A-21C when an additional, bypass venting mechanism 2250 is placed upstream of the vent membrane 2150.

In FIG. 22A, like in FIG. 21A, sample S is delivered, for example, via positive pressure, at an end of the channel 2190 (or chamber) opposite to an end at which gas-permeable vent membrane 2150 is disposed. The dashed arrows in FIGS. 21A-21C indicate the direction of sample delivery and movement through the channel 2190, with the shaded area representing the sample S and the nonshaded area representing gas (e.g., air). The channel 2190, in an exemplary configuration, may be defined by a base portion 2130 and a film layer 2120, with the film layer comprising a vent hole (not shown) positioned beneath the membranes 2150 and 2250 to permit gas to escape therethrough. Alternatively, as described with reference to FIGS. 21A-21C above, the membranes 2150 and 2250 may be eliminated, and a micro-sized vent hole in the film layer used instead.

In FIG. 22A, as the sample S is forced via pressure through the channel 2190, gas (e.g., air) residing in the channel 2190 is compressed and passed out of the channel 2190 through the vent holes (not shown) and the gas-permeable membranes 2150 and 2250, as shown by the solid arrows proximate the membranes 2150 and 2250. As the sample S continues to move downstream in the channel 2190 (e.g. toward the membrane 2150), gas that is between the sample S and the end of the channel 2190 continues to be released through the vent membrane 2150, with no gas being released through the membrane 2250 while the sample S moves into the region of the channel 2190 aligned with the membrane 2250, as shown in FIG. 22B.

Eventually, due to the continued positive pressure applied at the end of the channel 2190 proximate the dashed arrow, as shown in FIG. 21C, the sample S reaches a location in the channel 2190 corresponding to the vent hole (not shown) and membrane 2150 (e.g., the end of the channel 2190 opposite the end to which pressure is applied). In the additional upstream venting arrangement depicted in FIG. 22, however, if further pressure is applied after the sample S reaches the position shown in FIG. 22C, gas trapped in the channel 2190 upstream of the sample S may be released through the membrane 2250 and corresponding vent hole (not shown), as indicated by the solid arrow proximate the membrane 2250. By releasing the gas through the additional upstream venting mechanism (e.g., membrane 2250 in FIGS. 22A-22C), over-pressurization of the channel 2190 may be prevented and the sample movement in the channel 2190 will stop and the sample S will remain in the position shown in FIG. 22C without leaking from the channel 2190.

In order to provide the proper functioning of the upstream bypass venting mechanism, as described with reference to FIGS. 22A-22C, however, the location of the upstream venting mechanism and the volume of the sample supplied must be selected so as not to cause over-pressurization or incomplete sample delivery. Examples of how over-pressurization and incomplete delivery may occur if the sample volume and upstream venting position are not chosen appropriately are schematically depicted in FIGS. 23A and 23B, respectively.

Referring to FIG. 23A, incomplete sample delivery may occur if the location of the upstream venting mechanism 2355 and the volume of delivered sample S are not selected appropriately. In other words, the sample S will not reach and fill the end portion of the channel (or chamber) 2390 and gas (e.g., air) will become trapped underneath the venting mechanism 2350 downstream of the sample S. The situation in FIG. 23A may occur when the amount of sample S supplied to the channel 2390 and the location of the upstream bypass vent mechanism 2355 are such that the sample S advances past the vent mechanism 2355 prior to reaching the vent 2350 at the end of the channel 2390 where it is desired to collect the sample S. In this situation, as depicted in FIG. 23A, as positive pressure is supplied to the channel 2390, shown by the dashed arrow, the sample S is moved within the channel 2390 toward the vent mechanism 2350. However, as the sample S moves past the upstream vent mechanism 2355, the sample front has not yet reached the vent mechanism 2350, but continued application of pressure causes gas in front of the sample S (i.e., to the left of the sample S in FIG. 23A) to escape through the upstream vent mechanism 2355. This upstream venting of gas results in the pressure becoming equalized with the atmosphere despite the continued application of pressure in the channel 2390. Due to the pressure equalization, there is no pressure to cause further advancement of the sample S within the channel 2390, thus resulting in incomplete delivery of the sample S to the desired location (e.g., the end of the channel beneath the vent mechanism 2350 in FIG. 23A).

On the other hand, as depicted in FIG. 23B, the location of the upstream venting mechanism 2355 and the amount of sample S delivered to the channel 2390 may be selected such that the sample S completely blocks both venting mechanisms 2355 and 2350 once the sample S has advanced through and reached the end of the channel 2390. In this situation, continued application of pressure to the channel 2390, as indicated by the dashed arrow in FIG. 23B, may result in sample S leaking from the venting mechanism 2350, as shown by the solid arrow in FIG. 23B. Sample leakage through the venting mechanism 2350 and/or 2355 may occur substantially as described with reference to FIG. 21C.

Referring now to FIG. 24, an exemplary embodiment of a multi-chamber substrate 2410 may include an upstream venting mechanism that protects against over-pressurization and leakage, as described in FIGS. 22A-22C, while also including features that avoid the problems described in FIGS. 23A and 23B. As shown in FIG. 24, the substrate 2410, which may include a base and film layer in accordance with various embodiments of the disclosure, defines a plurality of sample chambers 2480 forming an array. The chambers 2480 are in flow communication with a plurality of sample introduction chambers 2475, which distribute sample supplied to the substrate 2410 via a main fluid channel 2470. The chambers 2480 also are in flow communication with venting chambers 2490 via venting channels 2476. The venting chambers 2490 are associated with venting mechanisms (not shown), such as, for example, the various membrane embodiments or micro-sized vent holes described herein.

Upstream of the chambers 2480, the substrate 2410 is provided with a venting mechanism 2455, which may be, for example, in the form of a vent hole in a film layer of the substrate 2410 covered with a venting membrane. This upstream venting mechanism 2455 may allow gas (e.g., air) to escape from the substrate 2410 after the various channels and chambers have been filled such that over-pressurization and sample leakage out of the venting mechanisms associated with the venting chambers do not occur.

In accordance with the exemplary embodiment of FIG. 24, the substrate 2410 also defines an overfill channel 2475 and overfill chamber 2495. The overfill channel 2475 leads from the downstream end of the main fluid channel 2470 and terminates in the overfill chamber 2495. The purpose of the overfill channel 2475 and overfill chamber 2495 is to provide a collection reservoir for the sample so as to ensure that complete delivery of the sample to the chambers 2480 and venting chambers 2490 occurs. Providing an overfill chamber 2495 of sufficient size allows for a sufficient volume of sample S to be loaded into the substrate 2410 to ensure complete delivery of the sample S, without a risk of overfilling and/or overpressurizing the substrate 2410 such that leakage may occur.

The overfill channel 2475 may have a smaller cross-sectional area than the main fluid channel 2470. The smaller cross-section will increase the fluidic resistance (e.g., pressure) encountered by the sample S as it fills the substrate 2410. As such, the overfill chamber 2495 will fill only after the remaining chambers 2480 and 2490 and channels 2470, 2420, and 2400. In various embodiments, rather than a straight overfill channel of reduced cross-section, an overfill channel having a serpentine configuration may be used as depicted in FIG. 24 and/or a combination of serpentine configuration and reduced cross-section may be used. The serpentine configuration can lengthen the overfill channel in comparison to a straight overfill channel substantially without increasing the overall size of the substrate. The lengthening and serpentine configuration of the overfill channel also may function to increase fluidic resistance encountered by the sample such that the overfill chamber fills after the remaining portions of the substrate.

According to various embodiments, the inlet sample volume requirement may be calculated as follows to ensure that all of the sample chambers 2480 are filled and the substrate is not overpressurized. Assuming that the substrate 2480 has 24 sample chambers, as shown in FIG. 24, the inlet sample volume=(the volume of all 24 chambers 2480)+(the volume of all 24 venting chambers 2490)+(the volume of the main fluid channel 2470)+(the volume of the sample introduction channels 2420)+((the volume of the overfill chamber 2495)/2) Thus, the sample volume tolerance using the above inlet sample volume is ½ the volume of the overfill chamber, which will allow the volume to fill all of the sample chambers, without over-pressurizing the device.

According to various embodiments, aspiration of sample into the chambers can be assisted by moving the overfill chamber to the inlet to provide protection against over-aspirating the sample.

As discussed above, in various embodiments, it may be desirable to integrate sample preparation with a multi-chamber array substrate. For example, it may be desirable to elute nucleic acid from a membrane and supply the eluted sample volume directly to a substrate. Before filling the sample chambers with the eluted sample, however, it is desirable to ensure that the eluted sample has been sufficiently mixed to substantially homogenize the concentration of the sample prior to filling the sample chambers. If the eluted sample is not sufficiently homogenized, a concentration gradient may result in the substrate chambers. For example, the concentration of nucleic acid may be higher in upstream chambers than in downstream chambers of the substrate. Such a concentration gradient in the substrate may impair detection, quantization (e.g., for gene expression) and/or analysis of the biological sample being tested.

Figure 25:
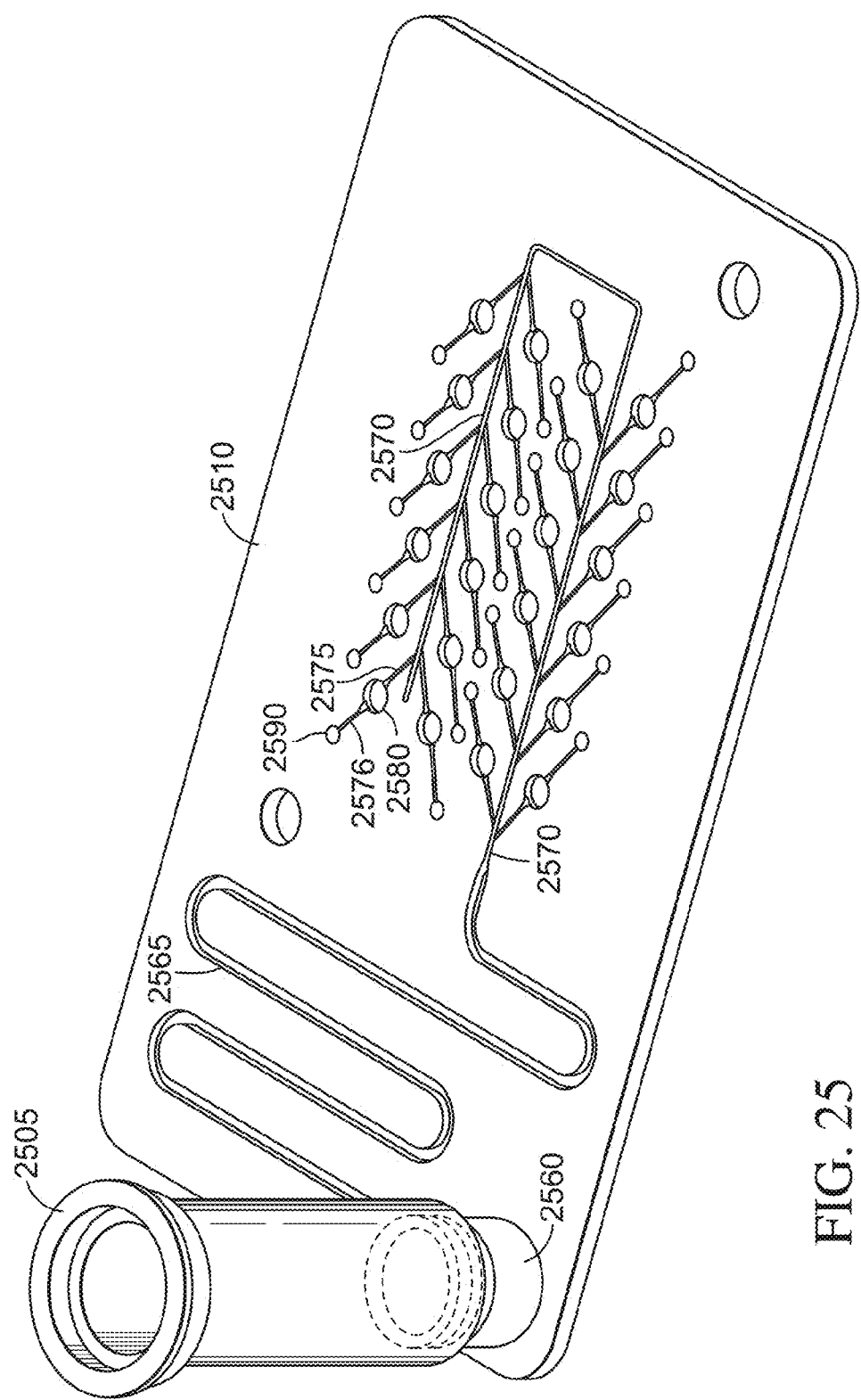
FIG. 25 illustrates a perspective view of yet another substrate for biological analysis according to various embodiments of the present teachings.

To mix the eluted sample so as to obtain a substantially homogenized concentration, an external mixing force, for example, via a vortex or the like, may be applied to the collected sample and the mixed sample may then be introduced into the substrate. In an alternative embodiment, however, it may be desirable to provide a mechanism for mixing eluted sample as part of the substrate itself. FIG. 25 shows an exemplary embodiment of a substrate configuration that provides for mixing of eluted sample within the substrate itself prior to the eluted sample being loaded into the sample chambers. In the exemplary embodiment of FIG. 25, passive mixing of the sample may occur in the substrate via a relatively simple design and without moving parts.

In the multi-chamber array substrate 2510 shown in FIG. 25, a tube 2505 configured to collect eluted sample (e.g., a sample of nucleic acid eluted from a membrane) is positioned in flow communication with a sample inlet port 2560 of the substrate 2510. The tube 2505 may collect eluted sample prior to any mixing, for example, nucleic acid sample eluted directly from a membrane. The substrate 2510 includes an array of sample chambers 2580, venting chambers 2590, sample introduction channels 2575, venting channels 2576, and a main fluid channel 2570, similar to other substrate embodiments described herein.

In addition to the various features listed above, the substrate 2510 also defines a serpentine mixing channel 2565 that connects the inlet port 2560 and the main fluid channel 2570 in flow communication with each other. The serpentine channel 2565 serves to lengthen the distance the sample travels between being supplied to the inlet port 2560 and filling the sample chambers 2580. By increasing the distance, and thus time, the sample travels prior to filling the chambers 2580, diffusion may be increased in the sample thereby mixing the sample and promoting homogenization of the sample concentration. In other words, moving a plug of liquid, such as a volume of eluted sample, through a channel of sufficient length prior to introducing the sample into the sample chambers may take advantage of the recirculation patterns that occur along the axis of the microfluidic channel that results from the plug of liquid having a parabolic velocity profile with substantially flat menisci at both ends of the plug. With a long enough mixing channel, and thus time, such recirculation patterns may act to mix the sample plug and provide a substantially uniform concentration prior to the sample being introduced into the sample chambers. Enhanced mixing may also occur by providing the mixing channel 2565 with sharp corners rather than rounded corners and/or by applying various surface finishes configured to enhance mixing.

Thus, the mixing channel 2565 provides a passive mixing feature that is integral with the substrate 2510. This permits direct loading of the substrate 2510 with eluted sample without prior mixing, while ensuring that the sample filling the chambers 2580 will have a substantially uniform concentration for all of the chambers 2580. The serpentine mixing channel 2565 may be relatively large in comparison to the main fluid channel 2570. By way of example only, the main fluid channel 2570 may be approximately 150 μm wide by approximately 50 μm deep, while the width of the mixing channel 2565 may range from approximately 1 mm to approximately 2 mm and have the same depth as the main fluid channel 2570.

A straight mixing channel may be used rather than the serpentine mixing channel shown in FIG. 25, however, using a straight channel having approximately the same length of the serpentine channel may increase the overall dimensions of the substrate 2510. Thus, the serpentine configuration provides a benefit of providing a sufficient length over which diffusion of the eluted sample can occur, without substantially increasing the overall dimensions of the substrate. Further, the bends in the serpentine channel configuration may promote additional mixing of the sample as it travels through the channel.

Figure 26:
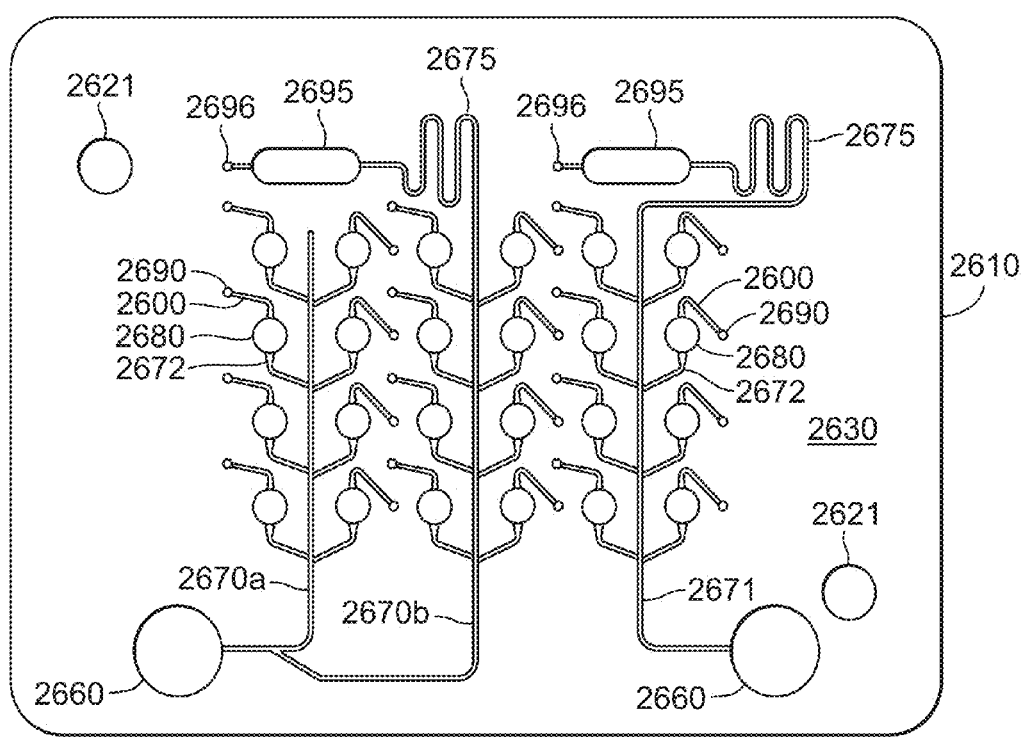
FIG. 26 illustrates a top view of yet another substrate for biological analysis according to various embodiments of the present teachings.

Yet another exemplary embodiment of a multi-chamber array substrate 2610 is depicted in FIG. 26. The view of the substrate 2610 shows the various features of the base 2630 of the substrate that, together with a film layer, as has been described for various substrate embodiments above, form a sample fluid distribution network including main fluid channels 2670a, 2670b, and 2671, inlet channels 2672 leading from the main fluid channels to sample chambers 2680, and venting channels 2600 leading from sample chambers 2680 to venting chambers 2690. Thus, the view in FIG. 26 is through a film layer applied over the side of the base 2630 that has openings defining the various features described above. Further features of the substrate 2610 include sample inlet ports 2660 for supplying sample to the substrate 2610 and to main fluid channels 2670a, 2670b, and 2671, overfill chambers 2695 and overfill channels 2675 leading from main fluid channels 2670b and 2671 to the overfill channels 2695. According to various exemplary embodiments, the substrate 2610 also may include indexing holes 2621 to help align and position the substrate 2160 in various biological testing apparatuses, such as, in conjunction with thermal blocks and the like for performing PCR or other biological analysis.

The substrate 2610 of FIG. 26 may be made of a variety of materials for the base and film layers, including any of the materials that have been discussed above. In particular, the materials chosen may be PCR compatible materials. By way of example, the base 2630 may be made molded from COP (e.g., ZEONOR 1420R) and the film layer that together with the base 2630 defines the sample distribution network (e.g., the sample chambers, channels, venting chambers, etc.) may be an aluminum PSA layer. In addition, it is envisioned that various sealing, venting, and mixing mechanisms that have been described above may be used in combination with the substrate depicted in FIG. 26 and those having skill in the art would understand based on the teachings herein how to combine those mechanisms and/or various structural configurations associated with those mechanisms with the embodiment of FIG. 26. By way of example only, in various embodiments, the substrate of FIG. 26 may be combined with any of the venting mechanisms illustrated in FIGS.

14-16. That is, the base 2630 of the embodiment of FIG. 26 may replace the base 1430 shown in FIGS. 14-16 and be combined with the other components shown in those figures, including the film layer 1420, the film layer 1425, and any of the membranes 1450, 1550, and 1650. Other structural aspects of the substrate 2610 shown in FIG. 26 are discussed below in more detail.

As noted above, the exemplary embodiment of FIG. 26 includes two inlet fluid supply ports 2660. One of the ports 2660 is in flow communication with main fluid supply channels 2670a and 2670b and the other inlet port 2660 is in flow communication with main fluid supply channel 2671. Main fluid supply channels 2670a and 2670b are in parallel connection with each other and the inlet port 2660, however, the inlet port 2660 also may supply fluid to main fluid channels that are serially connected, for example, as shown in the exemplary embodiment of FIG. 27. The main fluid supply channels 2670a and 2670b are configured to supply fluid (e.g., biological sample) to a first group of sample chambers 2680 (e.g., 16 chambers in FIG. 26) and the main fluid supply channel 2671 is configured to supply sample to a second group of chambers 2680 (e.g., 8 chambers in FIG. 26). The main fluid supply channels 2670a and 2670b and the first group of chambers 2680 are not in flow communication with the main fluid supply channel 2671 and the second group of chambers 2680.

This configuration of two inlet ports 2660 for supplying two differing sample chamber networks that are not in flow communication with each other permits two differing samples to be supplied to the substrate 2610 and/or differing biological testing (analysis) to be performed within the same substrate 2610. Moreover, according to various embodiments, the dual fluid distribution network provided in the substrate 2610 may provide a negative template control mechanism in order, for example, to test for false positives. By way of example, the inlet portion 2660 connected to the main fluid channels 2670a and 2670b may be supplied with a biological sample for which PCR analysis may be desired, while the inlet port 2660 in flow communication with the main fluid supply channel 2671 may be supplied with a blank sample (such as, for example, an elution buffer such as deionized water or Tris HCl). Analysis, such as via optical detection (for example, by detection of a fluorescent signal), of both groups of sample chambers may be performed and if a signal is detected in the sample chambers filled with the blank sample, this may indicate that the substrate is contaminated or otherwise susceptible to giving a false positive result.

Although the exemplary embodiment of FIG. 26 depicts 16 sample chambers in flow communication with one inlet port 2660 and 8 sample chambers in flow communication with the other inlet port 2660, any number of sample chambers may be provided in flow communication with each inlet port. However, when using one group of sample chambers and corresponding inlet port as a negative template control, it may be desirable to provide less sample chambers than for a group of chambers and corresponding inlet port being used for analysis of biological sample. It also should be understood that each inlet port may supply more than one main fluid channel, which may be connected either in parallel or serially. In addition, more than two sample inlet ports may be provided and thus more than two groups of sample chambers may be supplied with differing samples.

Figure 27:
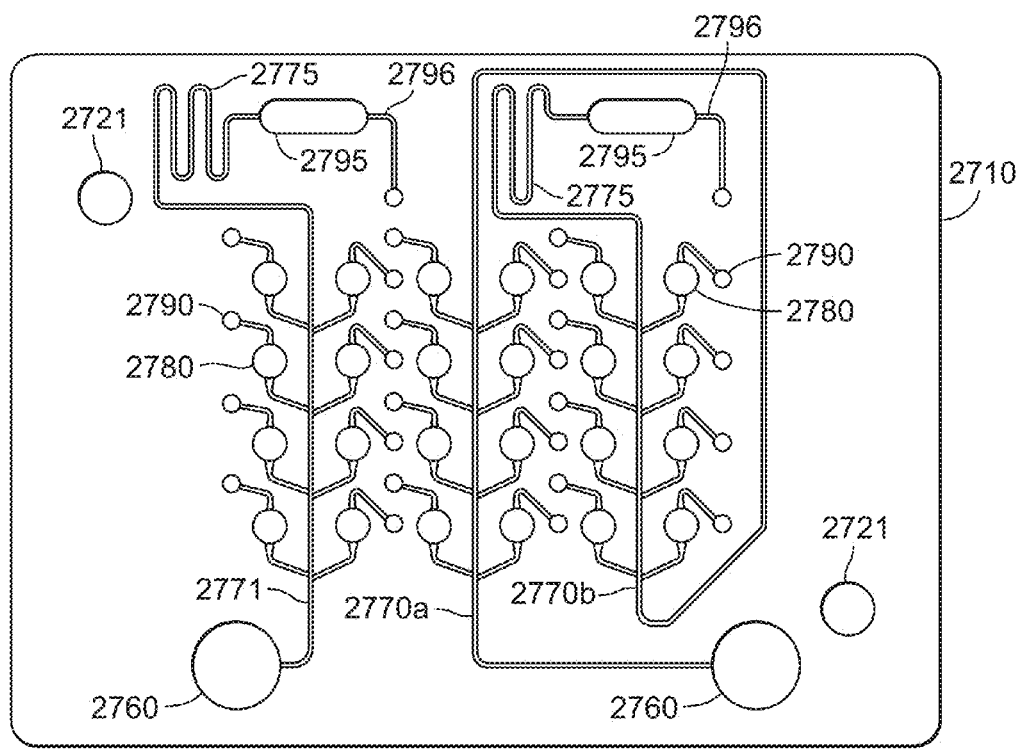
FIG. 27 illustrates a top view of yet another substrate for biological analysis according to various embodiments of the present teachings.

As mentioned above, for an inlet supply port supplying sample to more than one main fluid channel, those main fluid channels may be connected either serially or in parallel. The exemplary embodiment of FIG. 27 depicts a substrate 2710 similar to that of the substrate 2610 of FIG. 26, with the exception that the main fluid channels 2770a and 2770b that supply the group of 16 sample chambers 2780 are connected in series rather than in parallel. Like the substrate 2610, the substrate 2710 includes two inlet supply ports 2760 that are configured to supply differing fluids to two differing groups of sample chambers 2780, and thus can provide a negative template control as discussed above. Based on studies performed, providing the configuration of FIG. 26, wherein the main fluid channels 2670a and 2670b are connected in parallel rather than serially like the main fluid channels 2770a and 2770b, permits faster filling of the substrate. For example, for machined substrate prototypes having configurations similar to the embodiments depicted in FIGS. 26 and 27, using an applied pressure of 2 psi to perform the filling, the embodiment of FIG. 26 filled in 15 seconds while the embodiment of FIG. 27 filled in 4 minutes. At an applied pressure of 5 psi, the embodiment of FIG. 26 filled in 6 seconds and the embodiment of FIG. 27 filled in 22 seconds.

The exemplary embodiment of FIGS. 26 and 27 also include two overfill chambers 2695 and 2795 and two overfill channels 2675 and 2775 associated with each group of sample chambers 2680 and 2780. Each overfill channel 2675 leads respectively from the main fluid supply channels 2670b and 2671 to the overfill chambers 2695. Each overfill channel 2775 leads respectively from the main fluid supply channels 2770b and 2771 to the overfill chambers 2695. In a manner similar to that described above with reference to FIG. 24, the overfill chambers 2695 and 2795 and overfill channels 2675 and 2775 act to protect against overfilling, and thus over-pressurization of the substrate while ensuring sufficient filling of all of the sample chambers 2680 and 2780 with fluid.

An upstream venting mechanism in conjunction with the inlet supply ports 2660 and 2760 may be provided in order to protect against overfill and over-pressurization of the substrate, as discussed above with reference to FIGS. 22 and 24, for example. The upstream venting mechanism may be in the form of any of the venting mechanisms in accordance with the teachings herein, including, but not limited to, the venting mechanism of the embodiment of FIGS. 2A and 2B, the venting mechanism of the embodiment of FIG. 13, the backside venting mechanisms discussed with reference to the embodiments of FIGS. 15-16, and the venting mechanism of the embodiment of FIG. 17. In an exemplary aspect, the venting mechanism may be a vent hole provided in the film layer that covers the openings of the various fluid distribution features of the base (e.g., the film layer that together with the base forms the fluid distribution network of chambers and channels) and a gas permeable or porous membrane (e.g., hydrophobic membrane) situated over the inlet ports 2660 and 2760. Further, rather than positioning the upstream venting mechanism over the inlet ports 2660 and 2760, the upstream venting mechanism could be provided in conjunction with the fluid channels leading from the inlet ports 2660 and 2760 at a location proximate the inlet ports 2660 and 2760.

Using an upstream venting mechanism, the sample volume that may be used to fill the sample chambers 2680 and 2780 associated with the main fluid supply channels 2670a, 2670b and 2770a, 2770b may range from a minimum determined by adding the total volume of the sample chambers (the 16 chambers in the case of FIGS. 26 and 27), the total volume of the venting chambers, the main fluid supply channels, the inlet channels, and the venting channels associated with those chambers, and the volume of vent through holes (if any, for example, if the substrate of FIGS. 26 and 27 has a configuration like those shown in one of FIGS. 14-16) associated with the venting chambers and inlet supply port feeding the first group of chambers. The sample volume maximum may be calculated by adding the above volumes to the volume of the overfill chamber. According to an exemplary embodiment, assuming that for the fluid distribution networks associated with the group of 16 chambers of FIGS. 26 and 27 that the volume of each sample chamber 2680 and 2780 is 1.35 μL, the volume of the overfill chamber 2695 and 2795 is 5.09 μL, the total volume of the main fluid channels 2670a, 2670b and 2770a, 2770b, the inlet channels 2670 and 2770 and venting channels 2600 and 2700 associated with those main fluid channels, and the venting chambers 2690 and 2790 associated with the 16 sample chambers is 1.40 μL, the sample supply volume may range from 24.53 μL to 29.62 μL.

According to other exemplary embodiments, instead of or in addition to providing an upstream venting mechanism to protect against over-pressurization of the substrate, optical detection of sample reaching the overfill chambers 2695 and 2795 may be implemented. In an exemplary aspect, a dried, colored, fluorescence dye (e.g., a red dye) may be deposited in the overfill chambers 2695 and 2705, for example, proximate an inlet of the chambers 2695 and 2795. Thus, when the sample begins filling the overfill chambers 2695 and 2795, an optical detection mechanism may detect a change in color in the overfill chamber 2695 and 2795 and a feedback control mechanism may send a signal indicating to stop the application of pressure used for filling the substrate 2610 and 2710. For example, a feedback signal may be sent to a pressure-providing device (e.g., a pump, syringe, etc.) to automatically stop the pressure being used to fill the substrate and/or to an individual to manually stop the pressure.

The optical detection system may, for example, include an optical cover over the substrates 2610 and 2710 such that only the sample chambers 2680 and 2780, and the outlet portion of the overfill chambers 2695 and 2795 are viewable by an optical reading mechanism. The optical detection system may use, for example, an LED beam to illuminate the overfill chambers 2695 and 2795 and the optical reading mechanism may monitor the overfill chambers 2695 and 2795 near their respective outlets 2696 and 2697 for a change in fluorescence. After all of the chambers 2680 and 2780 have been filled, the sample will move into the overfill chambers 2695 and 2795, dissolve the predeposited dye and carry it to the outlets 2696 and 2796. The optical reading mechanism may then detect a fluorescence signal change and send a feedback signal, for example, to an operator or a filling device, to stop the application of pressure for supplying sample to the substrate 2610 and 2710. In other embodiments, the detector could detect the presence of an internal standard in the mastermix mixed with sample (which may be ROX), rather than spotting additional dye in the overfill chambers.

It has been observed that flowing deionized water into an empty chamber also causes a signal increase, which may be contributed by air and water having differing optical background signals and/or by the meniscus of the traveling water causing a signal change through both reflection and diffraction effects. Thus, in various exemplary embodiments, rather than using a red dye, LED beam, and fluorescence detecting mechanism in the overfill chamber, an optical sensor configured to detect the presence of liquid may be used. By way of example, a refractive index sensor may be used to detect liquid filling the overfill chamber. Because the refractive index of water (e.g., sample) differs from that of air, the light is deflected in a way that differs when the sample enters an overfill chamber and can be recognized by the detector. When the detector senses the change, a signal can be sent to stop the application of pressure and supply of sample.

Figure 37:
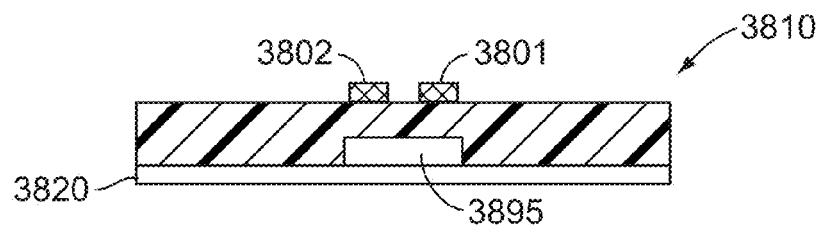
FIG. 37 is a partial cross-sectional view of a substrate that uses capacitance overfill detection in accordance with various embodiments of the present teachings.

Yet further exemplary embodiments for detection of the presence of sample in an overfill chamber include the use of a capacitance sensor or the use of an infrared sensor. Regarding the former, a capacitance sensor may be used to measure the capacitance between the film layer (e.g., an aluminum film layer) covering an overfill chamber and the opposite side of the substrate at the location of the overfill chamber. Since the dielectric constant of water is much greater than air, when sample fills the overfill chamber, the sensed capacitance may change and the capacitance sensor may send a signal indicating to stop filling (e.g., pressure application to) the substrate. FIG. 37 depicts an exemplary embodiment of using a capacitance sensor to detect the presence of sample in an overfill chamber 3895 in a substrate 3810. In FIG. 37, an electrode 3801 may be positioned on a side of the substrate 3810 opposite to the side of a film layer 3820, for example, an aluminum film layer. The electrode 3801 may be disposed on the substrate 3810 or may be part of an instrument cover or the like that clamps the substrate 3810 during filling. The aluminum film layer 3820 may be connected to a voltage supply to serve as a second electrode. In the case where the film layer is not a metal, another electrode could be positioned underneath the film layer 3820 similar electrode 3801. A voltage may be applied between the two electrodes (e.g., 3801 and the aluminum film layer 3820 in FIG. 37) and a capacitance of the chamber 3895 may be sensed. In various embodiments, the voltage may be applied as an AC field, and the capacitance may be detected as a phase shift, as well as permitting multiple readings, instead of the single change that would be registered with a DC field. An additional, optional electrode 3802 may be positioned adjacent, e.g., downstream, of the electrode 3801 and over the overfill chamber 3895 to use as a reference and a differential measurement may be made to increase the accuracy of the capacitance measurement. According to various embodiments, a conductivity detector can be used where the sample liquid is permitted to come into direct contact with the electrodes.

In various other embodiments, an infrared sensor may be used to detect sample filling of an overfill chamber. Because water and air have differing absorbance in the infrared range, infrared absorbance and/or reflection may be measured at the overfill chamber to detect the presence of sample (which contains water) entering the chamber. For example, in the case of an aluminum film layer covering the base of a substrate, infrared reflection off the aluminum layer over an overfill chamber may be detected.

Those having skill in the art will recognize various other detection mechanisms that may be used to detect the presence of the sample filling the overfill chamber, and the exemplary embodiments above should not be construed as limiting. Also, it should be understood that the various optical detection mechanisms described with reference to the embodiments of FIGS. 26 and 27 may also be applied to the exemplary embodiment of FIG. 24.

Using an optical detection mechanism, the volume of sample that may be supplied to the sample distribution networks associated with the first group of sample chambers 2680 and 2780 (the 16 chamber group) of the substrates 2610 and 2710 may range from a minimum determined by adding the total volume of the sample chambers (the 16 chambers in the case of FIGS. 26 and 27), the total volume of the venting chambers, the main fluid supply channels, the inlet channels, and the venting channels associated with those chambers, the total volume of the vent through holes (if any) associated with the venting chambers and inlet supply port feeding the first group of chambers, and half of the volume of the overfill chamber associated with the first group of chambers. The sample volume maximum may be determined in the same manner as the sample volume maximum when using the upstream venting mechanism approach, discussed above. Thus, assuming the various volume values as discussed above, the sample volume supplied to the first group of chambers 2680 and 2780 using optical detection as an over-pressurization/overfill protection mechanism may range from 27.08 μl to 29.62 μl.

Whether implementing the upstream venting mechanism approach or the optical detection approach, using an overfill chamber and channel, as described in the embodiments of FIGS. 24, 26, and 27 helps to ensure that sufficient filling of the sample chambers occurs without over-pressurization, and potential leakage, of the substrate. Further, this protection against underlining and over-pressurization can occur with a relatively large tolerance of the input sample volume. In other words, a precise amount of sample does not need to be determined and used to fill the substrate such that all of the sample chambers are filled, but over-pressurization does not occur. Rather, there is a volume range that may be used while still protecting against underfilling of the chambers and over-pressurization of the substrate.

Although various exemplary substrate embodiments described above and shown in the figures depicted partial views, schematic views, or substrates defining a 12-chamber, 16-chamber, or 24-chamber array, it should be understood that the various configurations and features of those embodiments can be applied to substrates of varying sizes and chamber arrays, including, for example, substrates defining multi-chamber arrays including various number of chambers, including, but not limited to, 12, 24, 36, 48, 96, 192, 384, 3072, 6144, or more sample chambers. In an exemplary configuration, the various substrates described above can have dimensions of, for example, about 127.0 millimeters by about 85.7 millimeters and define 384 sample chambers.

In some cases, for example when performing biological testing using a substrate defining a chamber array that differs from a conventional substrate, it may be desirable to use existing instrumentation for such conventional substrate configurations to perform biological analysis on substrates of other sizes. For example, at least some substrates in accordance with the present teachings may define 12-, 16-, or 24-chamber arrays, which have fewer chambers, and thus require fewer assays, than are available in a conventional low density array substrate (e.g., a substrate including a 96-chamber or 384-chamber array). When performing biological testing, such as, for example, real-time PCR, on the substrates with fewer chambers, a solution may be to perform testing on more than one substrate and thereby enable analysis of multiple samples during the same testing step. However, this may result in a mismatch between the number of samples presenting for analysis and the number of positions available on a substrate. Further, using a low density array substrate that does not use all of the chambers available may not be desirable since once subject to biological analysis, the substrates may not be suitable for further use. Also, in some cases, it may be desirable to subject one or more samples to differing assay panels (e.g., biological analysis) during a single processing routine (e.g., a single real time PCR assay step).

Figure 54:
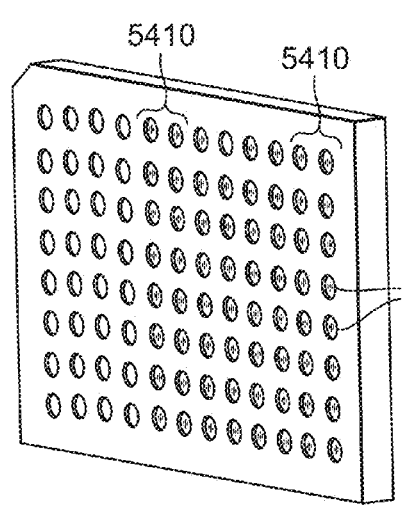
FIG. 54 is a perspective view of a holding fixture and subcards in accordance with various embodiments of the present teachings.
Figure 55:
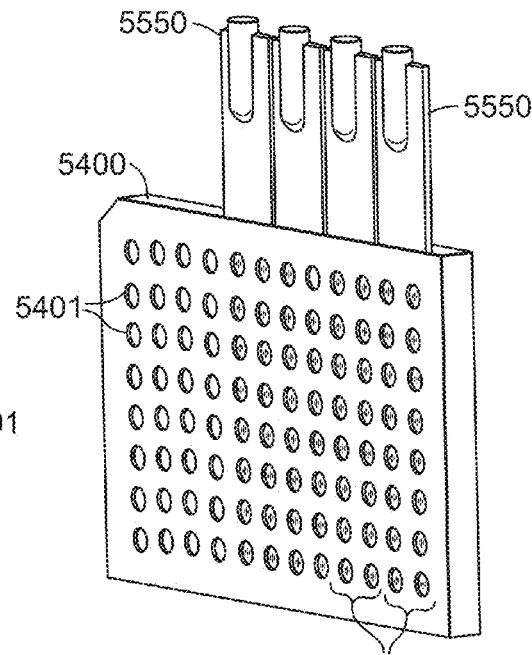
FIG. 55 is a perspective view of a holding fixture and subcards in accordance with various embodiments of the present teachings.
Figure 56:
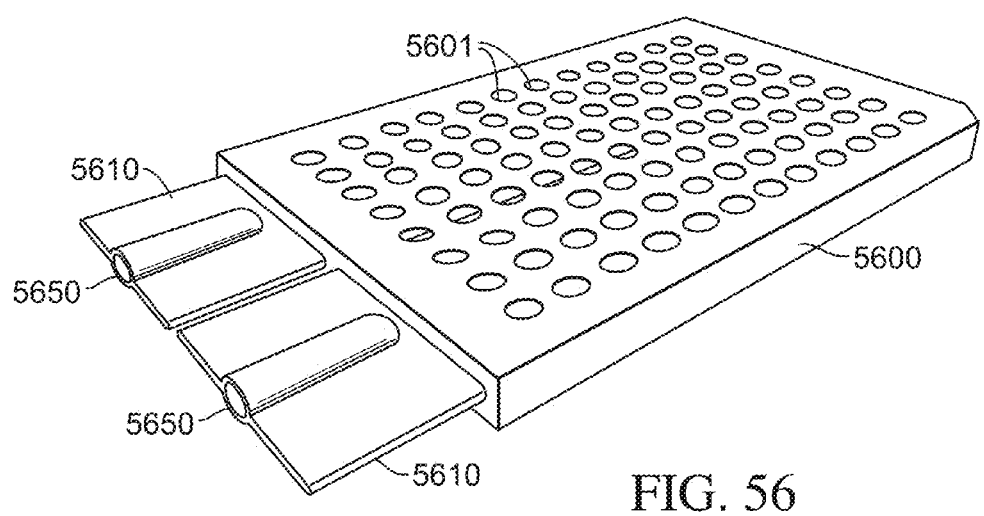
FIG. 56 is a perspective view of another holding fixture and subcards in accordance with various embodiments of the present teachings.
Figure 57:
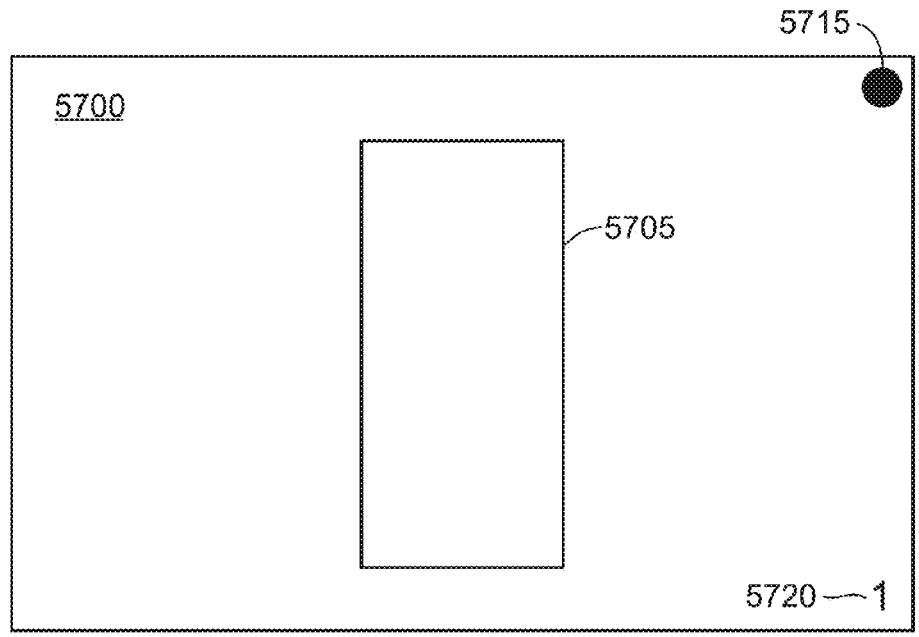
FIGS. 57-61 are perspective views of substrate carriers in accordance with various embodiments of the present teachings.
Figure 58:
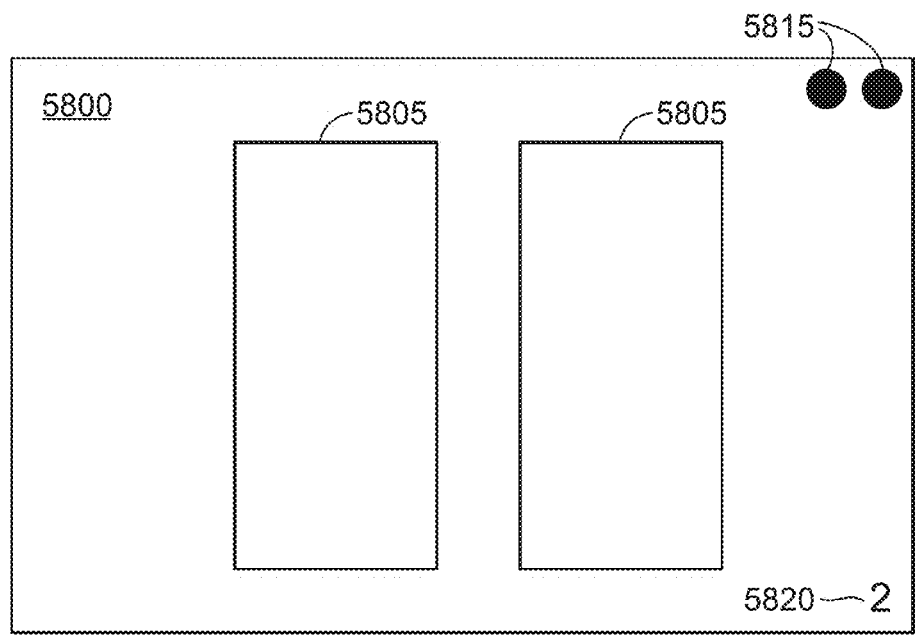

In order to achieve at least some of the desirable features above and in accordance with various embodiments of the present teachings, substrates that define a subset of chambers (e.g., "subcards") of a standard low density array substrate (e.g., 96- or 384-chamber array) may be provided that are configured to be combined and positioned into a holding fixture compatible for use with standard low density array testing instrumentation. FIGS. 54-56 show schematic perspective views of various holding fixtures that may be used to hold one or more subcards in accordance with exemplary embodiments.

The holding fixtures 5400 and 5600 of FIGS. 54-56 are in the form of a 4-sided frame with an array of openings 5401 and 5601 that correspond to locations of sample chambers on subcards. One or opposing sides of the holding fixtures 5400 and 5600 may define a slot configured to receive one or more subcards to be inserted into the fixture when performing biological testing, for example, real-time PCR. In the holding fixture of FIG. 54, 4 16-chamber array substrates (subcards) 5410 are shown inserted into the holding fixture 5400. The holding fixture 5400 is configured to hold a number of substrates that combined total a 96-chamber array. That is, the holding fixture 5400 includes an array of 96 openings 5401. FIG. 55 shows an exemplary embodiment of the use of the holding fixture 5400 to hold 4 16-chamber array subcards 5510 that include sample processing modules 5550 connected to the subcards 5510. In various exemplary embodiments, the sample processing modules 5550 may be detachable from the subcards 5510 prior to performing biological testing.

FIG. 56 depicts an exemplary embodiment of a holding fixture 5600 configured to hold subcards 5610 including 24-chamber arrays, with each subcard 5610 including 4 chambers across the substrate and 6 chambers down the substrate. The holding fixture 5600 may define slots at opposing ends to receive 4 subcards having a configuration like subcards 5610. The subcards 5610 shown in FIG. 56 include sample processing modules 5650, which may be detachable. It should be understood that the subcards without such sample processing modules also may be used.

The configurations of the subcards and holding fixtures of FIGS. 54-56 are exemplary only and not limiting. Various holding fixture and subcard configurations having differing number and arrangement of arrays may be used in accordance with the present teachings. Further, the subcards that are placed in the holding fixtures need not be of the same size and/or arrangement. For example, a subcard having a configuration like the subcards 5510 may be provided in the same holding fixture as a subcard having a configuration like the subcards 5610. Those having skill in the art would recognize that other combinations of subcards and configurations of subcards and holding fixtures may be used based on the present teachings.

In various embodiments, when performing biological testing, differing numbers of substrates maybe processed in each testing run. For example, one, two, three, four, or more cards may be processed (e.g., thermocycled) during a given biological testing run. This may be particularly true in benchtop testing of substrates.

In this situation, it is desirable to achieve substantial chamber-to-chamber thermal uniformity within and between substrates being processed. Moreover, it may be desirable to provide information to the testing instrumentation regarding the number of substrates being processed in a given run.

Figure 59:
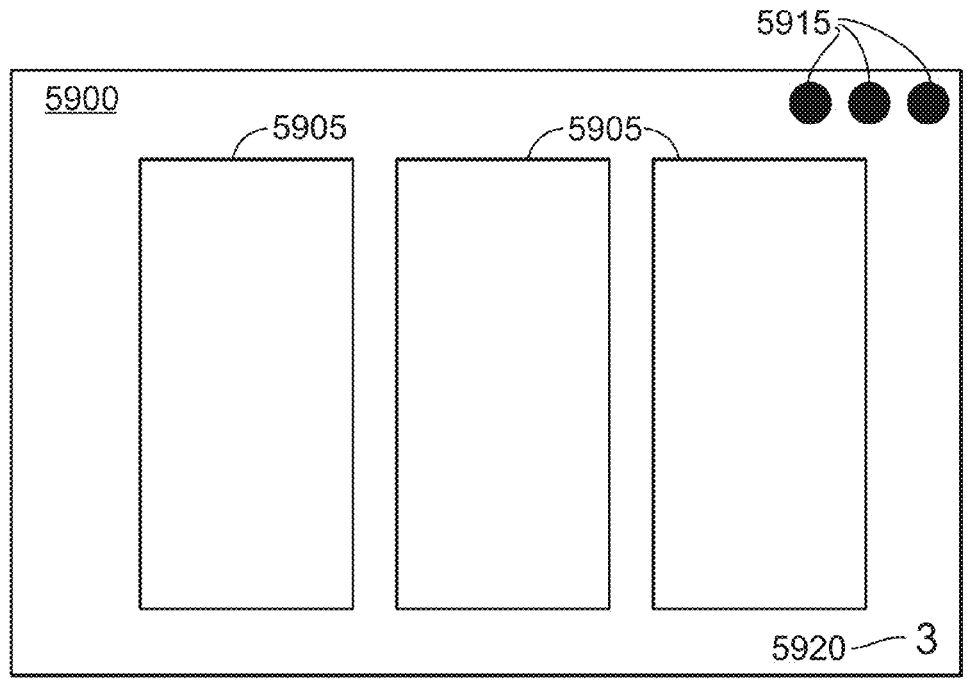
Figure 60:
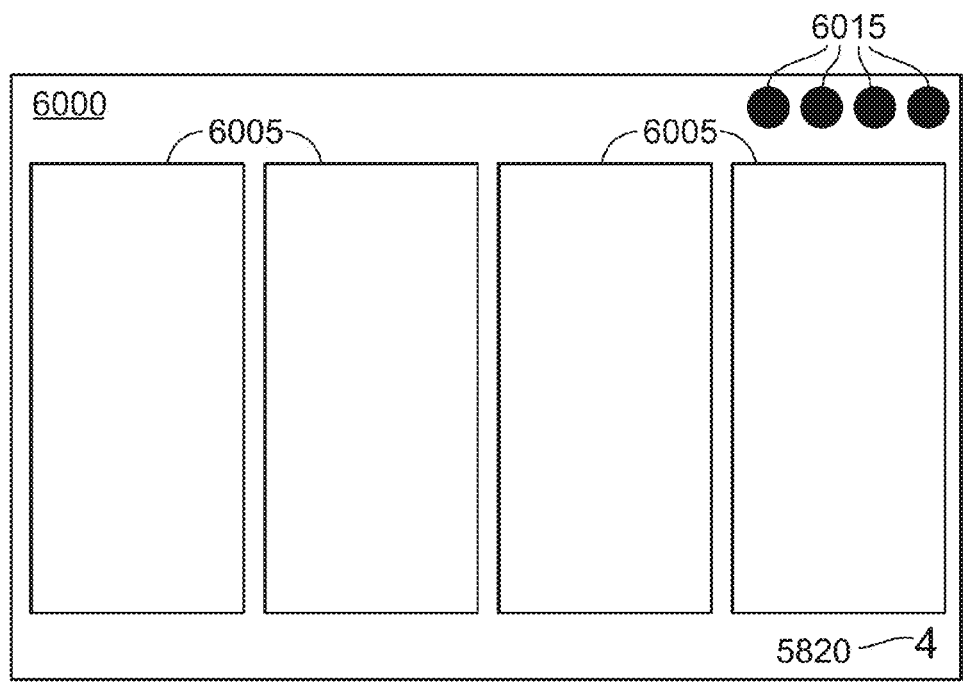

With reference to FIGS. 57-60, a set of four differing substrate (e.g., card) carriers are depicted. Each carrier is configured to hold a differing number of substrates. For example, the carrier 5700 in FIG. 57 defines a single cavity 5705 configured to hold a single substrate. The carrier 5800 in FIG. 58 defines two cavities 5805 each configured to hold a substrate. The carrier 5900 in FIG. 59 is configured to hold three substrates in three cavities 5905 defined by the carrier, and the carrier 6000 in FIG. 60 defines four cavities 6005 configured to hold four substrates.

Each of the differing carriers in FIGS. 57-60 may include indicators readable by the instrumentation used for processing to indicate how many substrates the carrier is configured to hold. By way of example, each carrier 5700, 5800, 5900, and 6000 may include one or more fluorescent scan marks 5715, 5815, 5915, and 6015 that indicate how many substrates the carrier is configured to hold (e.g., 1 scan mark for carrier 5700, 2 scan marks for 5800, 3 scan marks for 5900, and 4 scan marks for 6000). The carriers 5700, 5800, 5900, and 6000 also may include an indicator 5720, 5820, 5920, and 6020 readable by an individual (e.g., an Arabic numeral 1 through 4) to indicate how many substrates the carrier is configured to hold. Indicators other than Arabic numerals and/or fluorescent scan marks, such as, for example, bar codes and RFID identifiers, also may be appropriate identification mechanisms. Those having ordinary skill in the art would recognize numerous ways to achieve identification of the carriers, both by operators and by instrumentation.

To use the carriers of FIGS. 57-60, a user installs the appropriate number of sample-filled substrates (e.g., one to four in the exemplary embodiments of FIGS. 57-60) into a carrier, places the carrier into the testing instrumentation, and begins testing (e.g., thermocycling). The testing instrumentation reads the indicators on the carrier to determine how many substrates are being processed and may be configured to control the processing steps (such as the thermocycling temperatures, times, locations of applied heat, etc.) based on that information. This may ensure that the testing processes are compatible with the number of substrates being tested so as to promote thermal uniformity.

Figure 61:
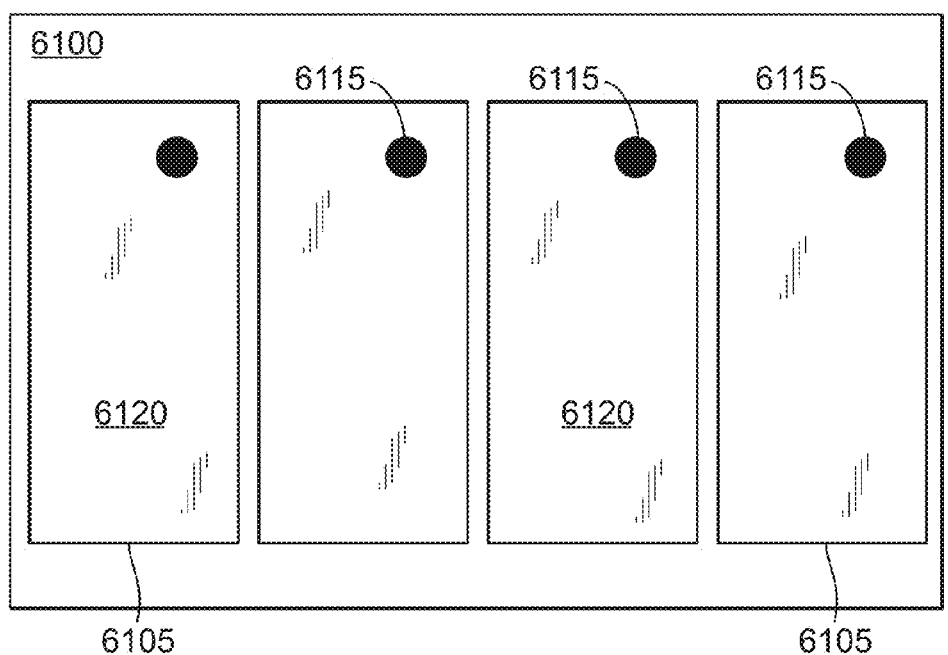

FIG. 61 depicts another exemplary embodiment of a substrate carrier that may be useful when performing biological testing on differing numbers of substrates in a given testing run. The carrier 6100 of FIG. 61 defines four cavities 6105 that are configured to receive a substrate for biological testing or a mockup card 6120. The mockup card 6120 may be removable from a cavity 6105 and replaced with a substrate for biological testing or may be placed in a cavity 6105 when the cavity 6105 is not being used to hold a substrate for biological testing. Each mockup card 6120 may be provided with an indicator 6115 readable by the instrumentation used for processing to indicate that a mockup card 6120 rather than a sample substrate is in place in a cavity. By being able to sense the number and locations of mockup cards versus sample substrates held by the carrier 6100 during a testing run, the testing processes may be adjusted (e.g., thermocycling temperatures, times, and locations of applied heat, etc.).

The present teachings provide a variety of structural arrangements, techniques, and/or methodology useful for performing biological analysis, including multiple analyte detection. It should be understood that although in some cases the embodiments described herein may focus on a particular aspect, various embodiments may be combined to form a system and/or substrate configuration useful for multiple analyte detection. By way of example only, various sealing approaches may be combined with various venting approaches. The various embodiments described herein are not intended to be mutually exclusive.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the" include plural referents unless expressly and unequivocally limited to one referent. Thus, for example, reference to "a layer" includes two or more different layers. As used herein, the term "include" and its grammatical variants are intended to be non-limiting, such that recitation of items in a list is not to the exclusion of other like items that can be substituted or added to the listed items.

Various embodiments of the teachings are described herein. The teachings are not limited to the specific embodiments described, but encompass equivalent features and methods as known to one of ordinary skill in the art. Other embodiments will be apparent to those skilled in the art from consideration of the present specification and practice of the teachings disclosed herein. It is intended that the present specification and examples be considered as exemplary only.

What is claimed is:
1. A system for distribution of a biological sample, the system comprising:
   a substrate, wherein the substrate comprises a plurality of sample chambers, a sample introduction channel for each sample chamber, and a venting channel for each sample chamber;
   a preloaded reagent contained in each sample chamber and configured for nucleic acid analysis of a biological sample that enters the substrate; and
   a sealing instrument comprising a roller provided with a plurality of sealing protrusions in the form of circumferential disks spaced from each other along a longitudinal axis of the roller such that each protrusion can align with a sample chamber and placed in contact with the substrate to seal each sample chamber so as to substantially prevent sample contained in each sample chamber from flowing out of each sample chamber,
   wherein the substrate is constructed of detection-compatible and assay-compatible materials.

2. The system of claim 1, wherein a sealing plate contacts the substrate during a reaction process in the sample chambers to seal each sample chamber.

3. The system of claim 2, further comprising a thermal block, wherein the thermal block comprises the sealing plate.

4. The system of claim 1, wherein the sealing instrument comprises one of a plate and a roller.

5. The system of claim 1, wherein the substrate comprises a film layer and wherein a portion of the film layer fills the sample introduction channels and the venting channels upon contact of the sealing instrument with the substrate.

6. The system of claim 1, wherein the sealing protrusions are configured to seal the sample introduction channels and venting channels for each sample chamber.

7. The system of claim 1, further comprising an additional sealing instrument, wherein the plurality of sealing protrusions comprises a first plurality of sealing protrusions associated with the sealing instrument and a second plurality of the sealing protrusions associated with the additional sealing instrument, the first plurality and second plurality of sealing protrusions being configured to seal differing groups of sample chambers when the sealing instrument and the additional sealing instrument are respectively placed in contact with the substrate.

8. The system of claim 7, wherein the first plurality of sealing protrusions is configured to seal the sample introduction channels for each sample chamber and the second plurality of sealing protrusions are configured to seal the venting channels for each sample chamber.

9. The system of claim 1, wherein each sealing protrusion is configured to contact a respective sample introduction channel and venting channel for each sample chamber when the sealing instrument is placed in contact with the substrate.

10. The system of claim 1, wherein the plurality of sealing protrusions are configured to respectively align with the plurality of sample chambers.

11. The system of claim 10, wherein each sample chamber is configured to receive a respective sealing protrusion such that the sealing protrusions seal the sealing chambers substantially at an inner peripheral surface defining each sample chamber.

12. The system of claim 1, wherein the sealing instrument further comprises a plurality of optical apertures configured to provide optical access to the sample chambers.

13. The system of claim 12, wherein the sealing protrusions are configured to pierce the substrate and enter the introduction and venting channels for each sample chamber.

14. The system of claim 1, wherein the sealing protrusions comprise one of pins, blades, and bumps.

15. The system of claim 1, wherein the substrate further comprises a plurality of sample supply channels, each sample supply channel being in flow communication with a differing group of sample introduction channels and corresponding sample chambers.

16. The system of claim 15, wherein the substrate further comprises a plurality of sample inlet ports, each sample inlet port being in flow communication with a differing sample supply channel.

17. The system of claim 1, wherein the at least one venting mechanism comprises a plurality of venting mechanisms respectively corresponding to the plurality of sample chambers.

18. The system of claim 1, wherein the substrate further comprises a venting chamber in flow communication with each venting channel.

19. The system of claim 1, wherein the substrate further comprises a venting chamber for each sample chamber, the venting chambers being in flow communication with the sample chambers via the venting channels, wherein the at least one venting mechanism comprises a plurality of venting mechanisms each corresponding to a respective venting chamber.

20. The system of claim 1, wherein the substrate further comprises a main venting channel in flow communication with the venting channels.

21. The system of claim 1, wherein the substrate further comprises an additional film layer, the film layers being disposed on opposing surfaces of the base.

22. The system of claim 21, wherein the additional film layer and the base together define the sample chambers, sample introduction channels, and venting channels.

23. The system of claim 1, wherein the at least one venting mechanism is configured to substantially prevent sample from passing through the at least one venting mechanism and out of the substrate.

* * * * *